US010213287B2

(12) United States Patent
Verin et al.

(10) Patent No.: US 10,213,287 B2
(45) Date of Patent: Feb. 26, 2019

(54) IMPLANTABLE SELF-CLEANING BLOOD FILTERS

(71) Applicant: VeoSource SA, Lausanne (CH)

(72) Inventors: Vitali Verin, Geneva (CH); Olivier Coquoz, Geneva (CH)

(73) Assignee: VeoSource SA, Lausanne (CH)

( * ) Notice: Subject to any disclaimer, the term of this patent is extended or adjusted under 35 U.S.C. 154(b) by 151 days.

(21) Appl. No.: 15/311,398

(22) PCT Filed: May 14, 2015

(86) PCT No.: PCT/IB2015/001206
§ 371 (c)(1),
(2) Date: Nov. 15, 2016

(87) PCT Pub. No.: WO2015/173646
PCT Pub. Date: Nov. 19, 2015

(65) Prior Publication Data
US 2017/0086959 A1  Mar. 30, 2017

Related U.S. Application Data

(60) Provisional application No. 61/994,276, filed on May 16, 2014, provisional application No. 62/029,044, filed on Jul. 25, 2014.

(51) Int. Cl.
*A61F 2/01* (2006.01)
*A61F 2/06* (2013.01)

(52) U.S. Cl.
CPC .......... *A61F 2/01* (2013.01); *A61F 2002/018* (2013.01); *A61F 2002/068* (2013.01);
(Continued)

(58) Field of Classification Search
CPC ................ A61F 2/01; A61F 2230/0043; A61F 2002/018; A61F 2250/0023;
(Continued)

(56) References Cited

U.S. PATENT DOCUMENTS

| 5,662,671 A | 9/1997 | Barbut et al. |
| 5,849,037 A | 12/1998 | Frid |

(Continued)

FOREIGN PATENT DOCUMENTS

| JP | 2010094141 | 4/2010 |
| WO | WO0053119 | 9/2000 |

(Continued)

*Primary Examiner* — Julian W Woo
(74) *Attorney, Agent, or Firm* — Christensen, Fonder, Dardi & Herbert PLLC

(57) ABSTRACT

A blood filter device having occlusion-resistant characteristics. The occlusion-resistant characteristics decrease the likelihood of the filter being blocked by thrombi. The filter device (252a, 252b) includes at least one anchor portion (42) for anchoring the filter device within one or more arteries (354a, 354b), and a filter portion (98) for filtering thrombi from the blood entering the artery. In some embodiments, an anchor portion is capped with a filter cap. In various embodiments, the filter cap is protrudes into the aorta to promote occlusion resistance. In one embodiment, the device can be modified in situ to re-establish normal blood flow through the artery in the unlikely case of thrombotic or other blockage of the filter. In some embodiments, a bypass opening or open channel defining an access port is provided to accommodate passage of surgical instruments into the artery and to enable blood flow to bypass the filter should the filter become heavily occluded.

3 Claims, 22 Drawing Sheets

(52) U.S. Cl.
CPC .............. *A61F 2230/0043* (2013.01); *A61F 2230/0069* (2013.01); *A61F 2230/0093* (2013.01); *A61F 2250/0023* (2013.01)

(58) Field of Classification Search
CPC ........ A61F 2230/0069; A61F 2002/068; A61F 2230/0093
USPC ...................................................... 623/1.36
See application file for complete search history.

(56) References Cited

U.S. PATENT DOCUMENTS

| | | | |
|---|---|---|---|
| 5,855,600 | A | 1/1999 | Alt |
| 5,938,697 | A | 8/1999 | Killion et al. |
| 6,136,022 | A | 10/2000 | Nunez et al. |
| 6,241,746 | B1 | 6/2001 | Bosma et al. |
| 6,258,115 | B1 | 7/2001 | Dubrul |
| 6,258,120 | B1 | 7/2001 | McKenzie et al. |
| 6,273,910 | B1 | 8/2001 | Limon |
| 6,312,463 | B1 | 11/2001 | Rourke et al. |
| 6,348,063 | B1 | 2/2002 | Yassour et al. |
| 6,635,070 | B2 | 10/2003 | Leeflang et al. |
| 6,652,554 | B1 | 11/2003 | Wholey et al. |
| 6,673,089 | B1 | 1/2004 | Yassour et al. |
| 6,695,858 | B1 | 2/2004 | Dubrul et al. |
| 6,712,834 | B2 | 3/2004 | Yassour et al. |
| 6,740,112 | B2 | 5/2004 | Yodfat et al. |
| 6,866,680 | B2 | 3/2005 | Yassour et al. |
| 6,929,653 | B2 * | 8/2005 | Strecter ................ A61F 2/013 128/898 |
| 7,156,858 | B2 | 1/2007 | Schuldt-Hempe et al. |
| 7,670,356 | B2 | 3/2010 | Mazzocchi et al. |
| 7,763,011 | B2 | 7/2010 | Ortiz et al. |
| 7,780,694 | B2 | 8/2010 | Palmer et al. |
| 7,857,843 | B2 | 12/2010 | Henderson |
| 7,927,346 | B2 | 4/2011 | VanCamp et al. |
| 8,062,324 | B2 | 11/2011 | Shimon et al. |
| 8,192,484 | B2 | 6/2012 | Frid |
| 8,211,158 | B2 | 7/2012 | Wolf |
| 8,221,446 | B2 | 7/2012 | Pal et al. |
| 8,252,017 | B2 | 8/2012 | Paul, Jr. et al. |
| 8,252,020 | B2 | 8/2012 | Hauser et al. |
| 8,353,943 | B2 | 1/2013 | Kuppurathanam et al. |
| 8,388,644 | B2 | 3/2013 | Parker |
| 8,430,904 | B2 | 4/2013 | Belson |
| 8,460,335 | B2 * | 6/2013 | Carpenter ............... A61F 2/013 606/200 |
| 8,506,619 | B2 | 8/2013 | Ortiz et al. |
| 8,597,342 | B2 | 12/2013 | McKinsey et al. |
| 8,679,149 | B2 * | 3/2014 | Belson .................... A61F 2/01 606/200 |
| 8,715,317 | B1 * | 5/2014 | Janardhan ................ A61F 2/01 606/200 |
| 8,728,152 | B2 | 5/2014 | Goldmann et al. |
| 8,911,504 | B2 | 12/2014 | Mathisen et al. |
| 8,940,040 | B2 * | 1/2015 | Shahriari ................. A61F 2/07 623/1.35 |
| 8,979,918 | B2 | 3/2015 | Murayama |
| 9,039,754 | B2 | 5/2015 | Nishigishi |
| 9,044,305 | B2 | 6/2015 | Grewe |
| 9,204,953 | B2 | 12/2015 | Mortarino |
| 9,326,840 | B2 | 5/2016 | Mortarino |
| 9,427,494 | B2 | 8/2016 | Persson et al. |
| 9,510,925 | B2 | 12/2016 | Hotter et al. |
| 10,076,400 | B2 * | 9/2018 | Krahbichler ............. A61F 2/013 |
| 2003/0100940 | A1 | 5/2003 | Yodfat |
| 2007/0021816 | A1 | 1/2007 | Rudin |
| 2007/0198075 | A1 | 8/2007 | Levy |
| 2009/0171451 | A1 | 7/2009 | Kuppurathanam et al. |
| 2011/0040372 | A1 | 2/2011 | Hansen et al. |
| 2012/0265289 | A1 | 10/2012 | Macatangay |
| 2013/0150882 | A1 | 6/2013 | Williams et al. |
| 2013/0211497 | A1 | 8/2013 | Charlebois et al. |
| 2014/0114340 | A1 | 4/2014 | Zhou et al. |

FOREIGN PATENT DOCUMENTS

| | | |
|---|---|---|
| WO | WO2005027751 | 3/2005 |
| WO | WO2006131930 | 12/2006 |
| WO | WO2008073964 | 6/2008 |

* cited by examiner

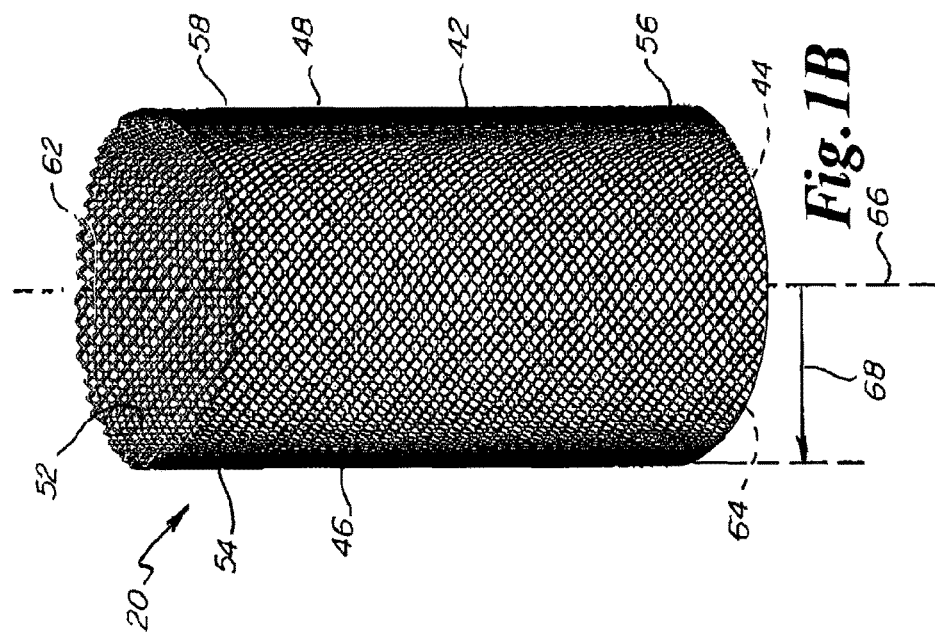
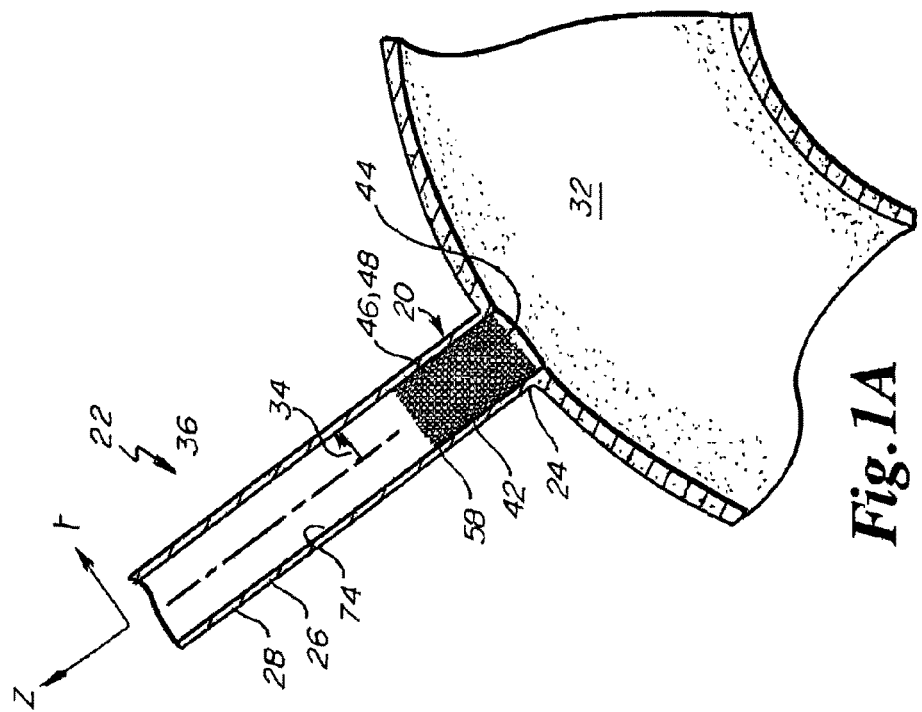
Fig. 1B
Fig. 1A

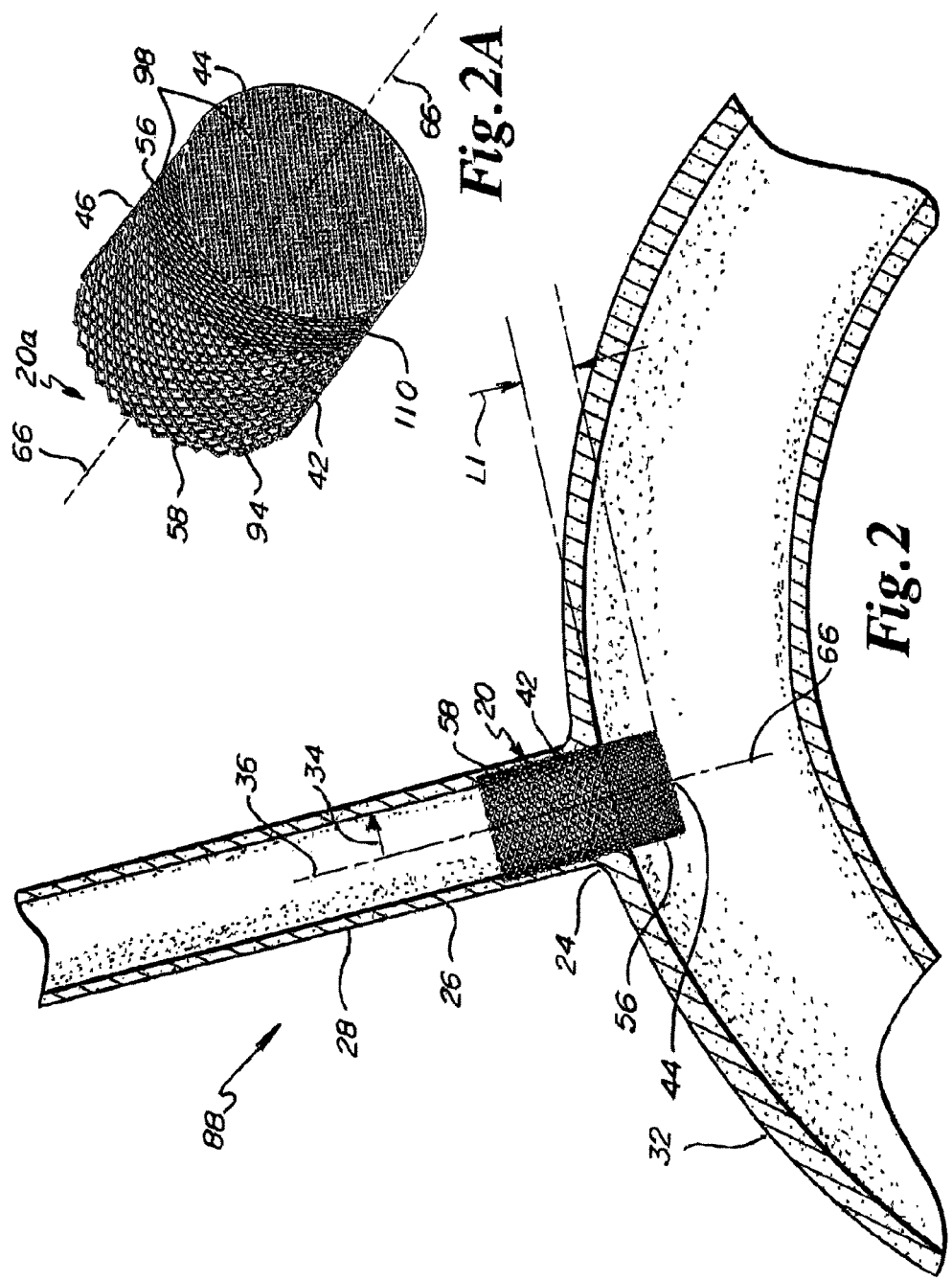

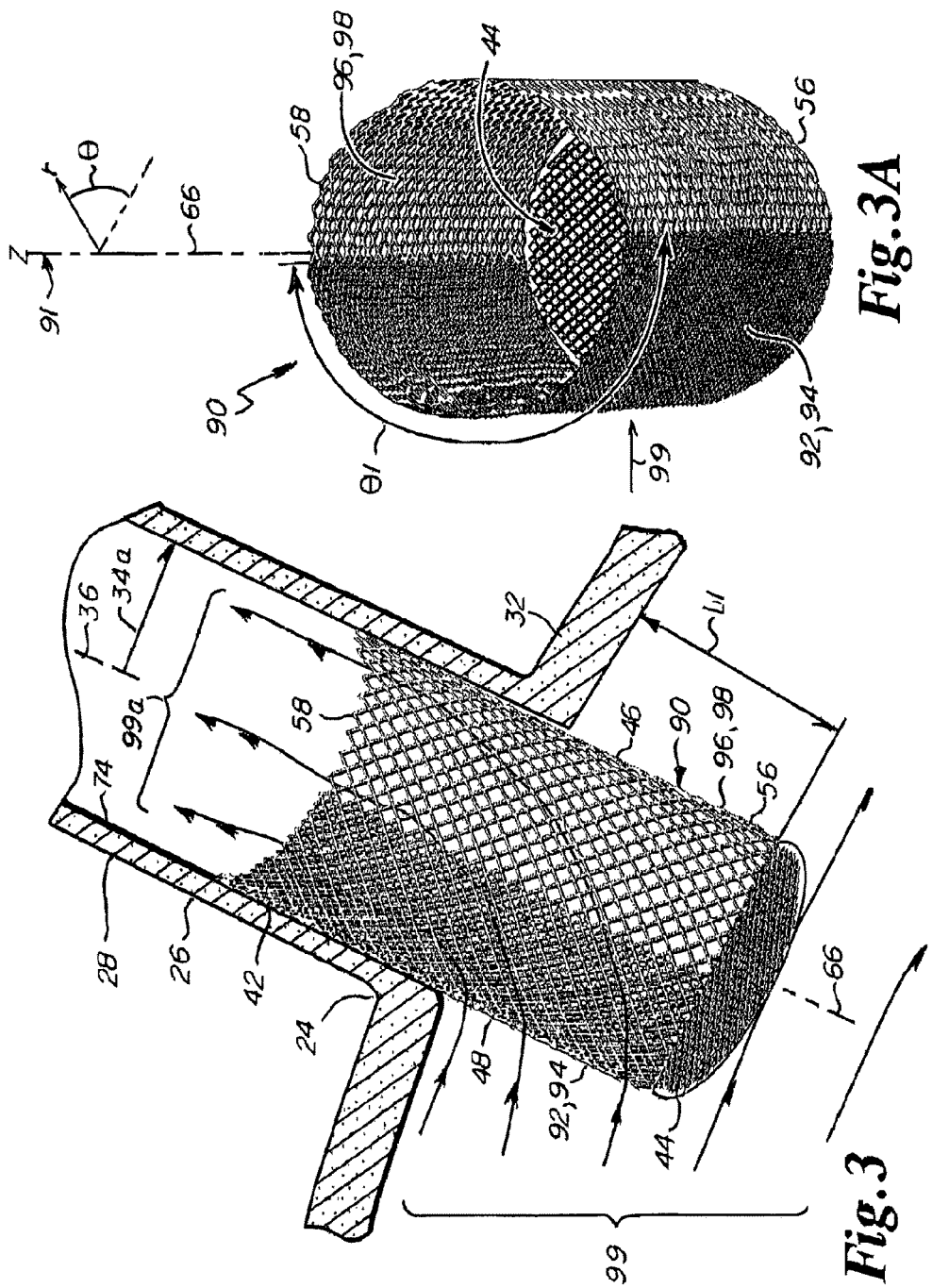

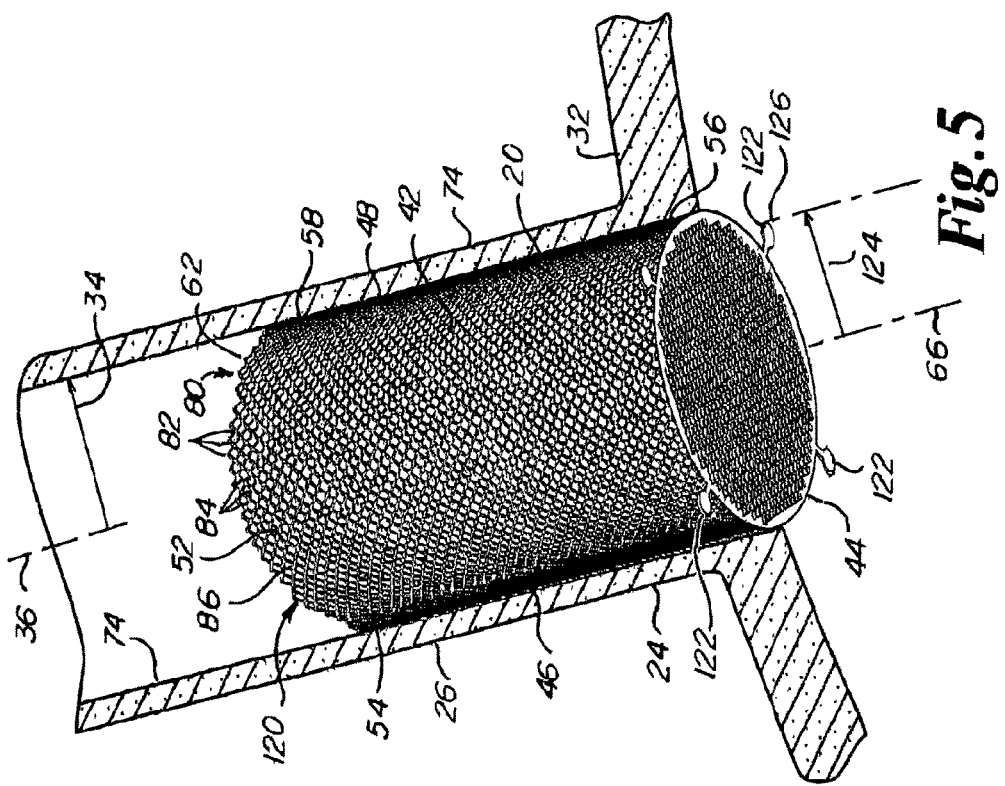
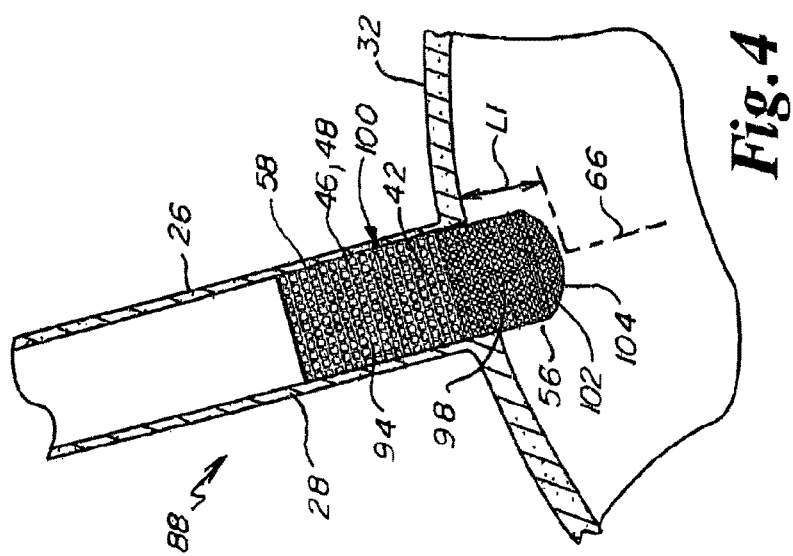

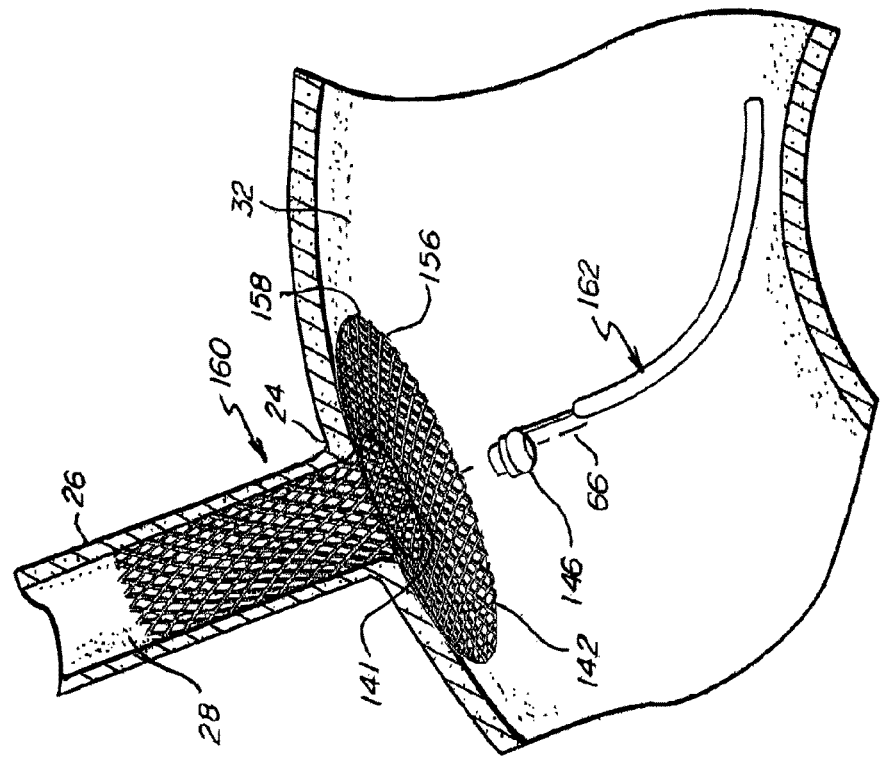
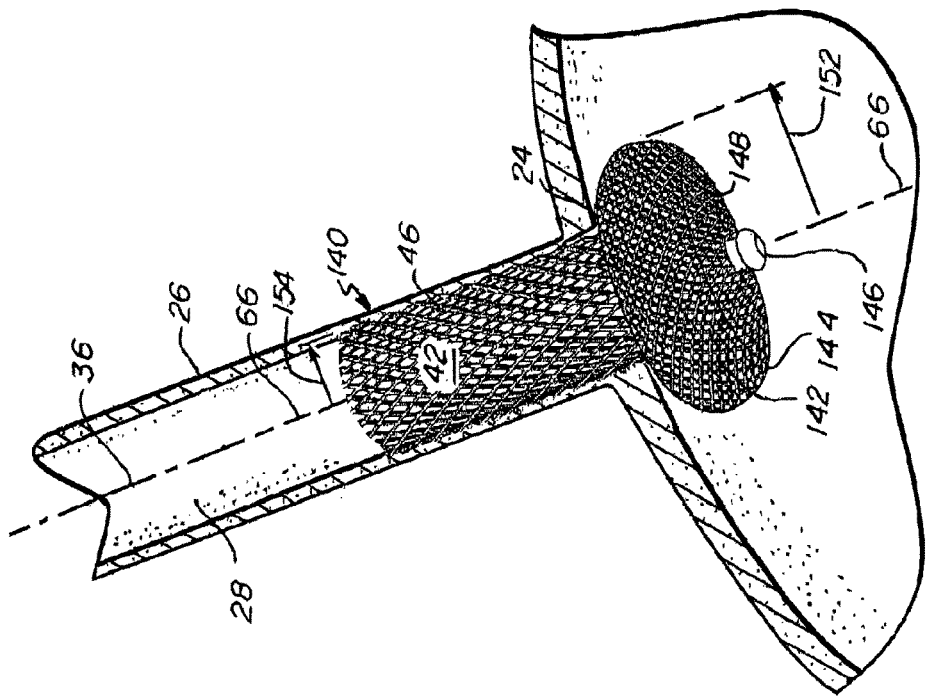

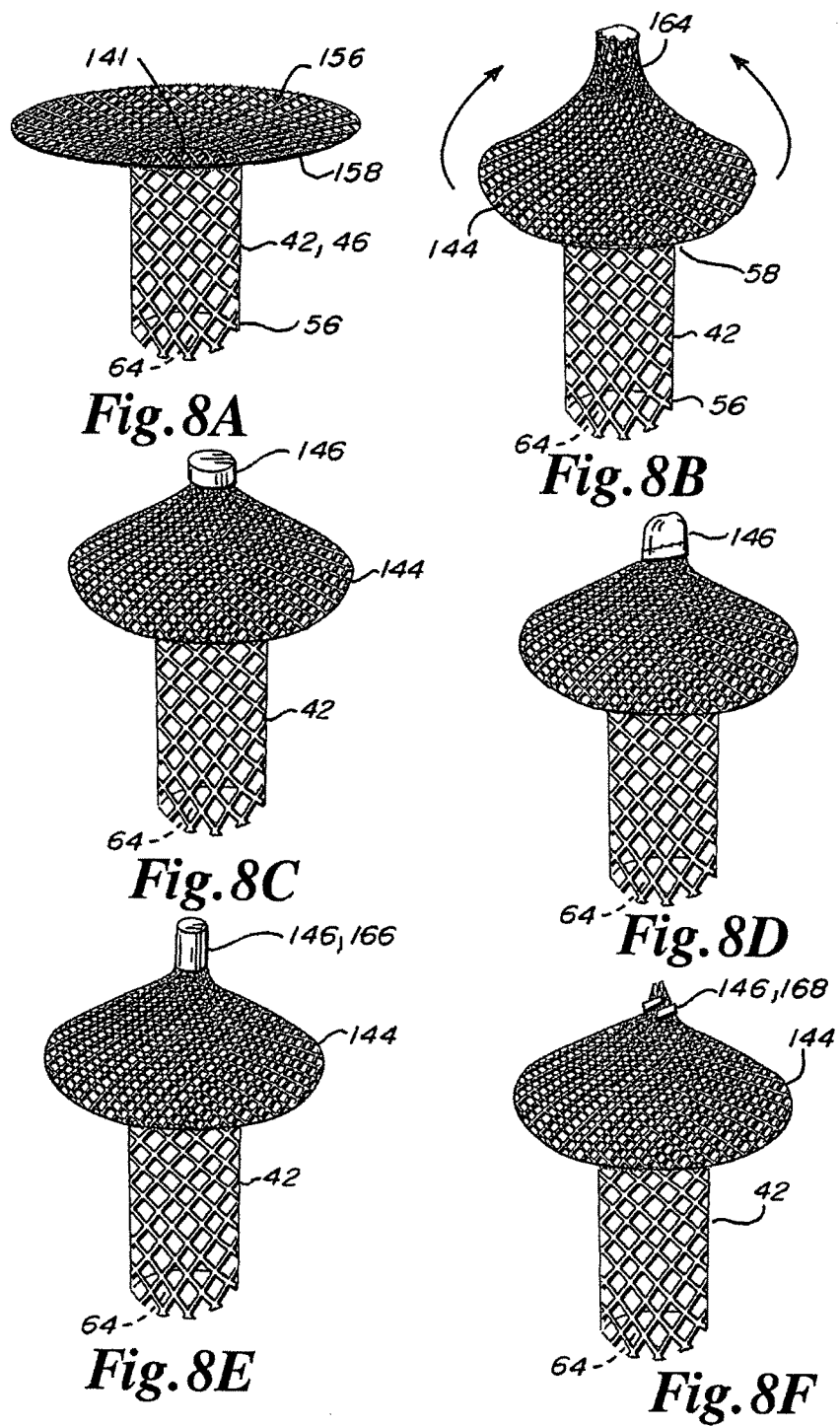

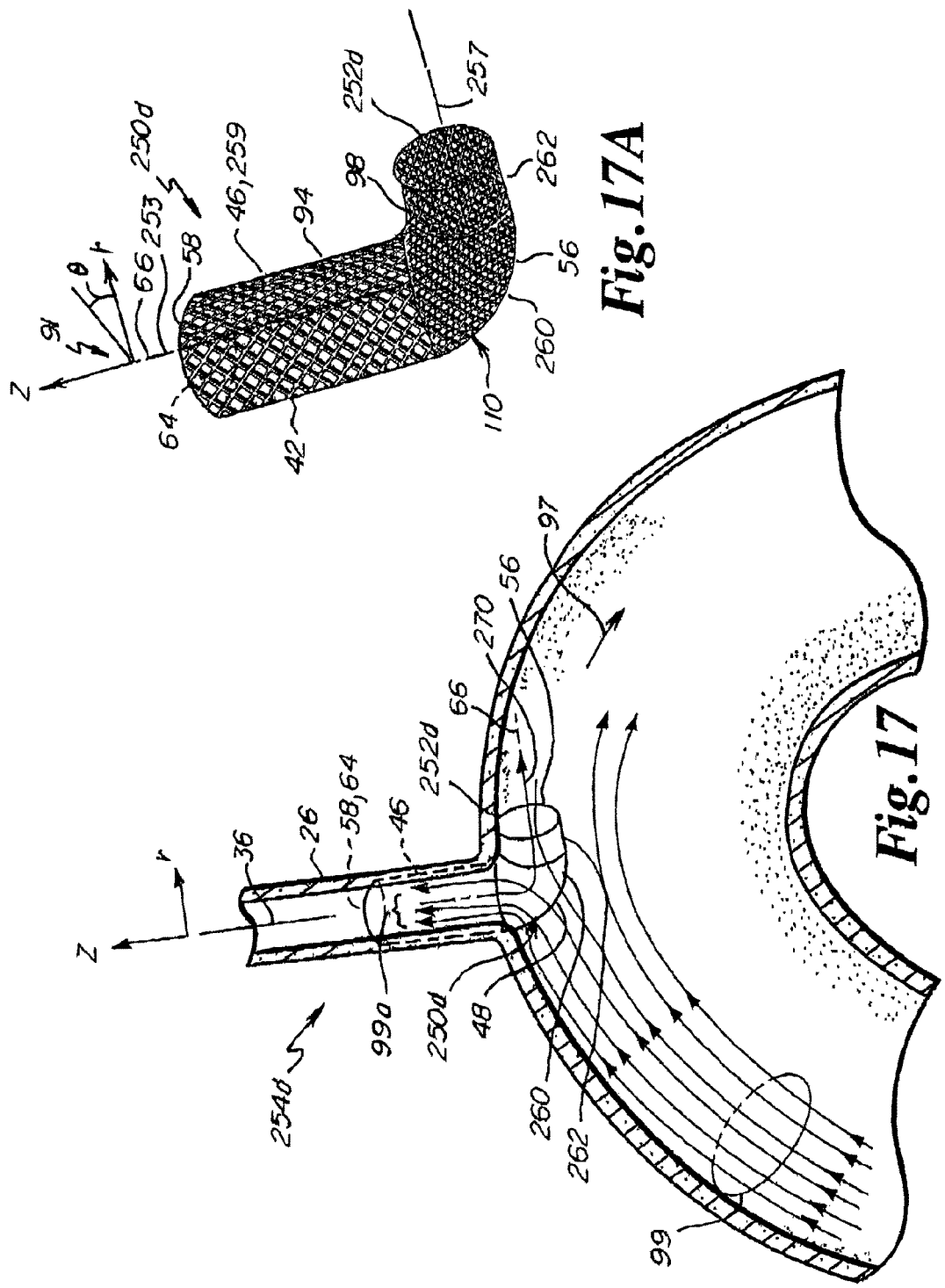

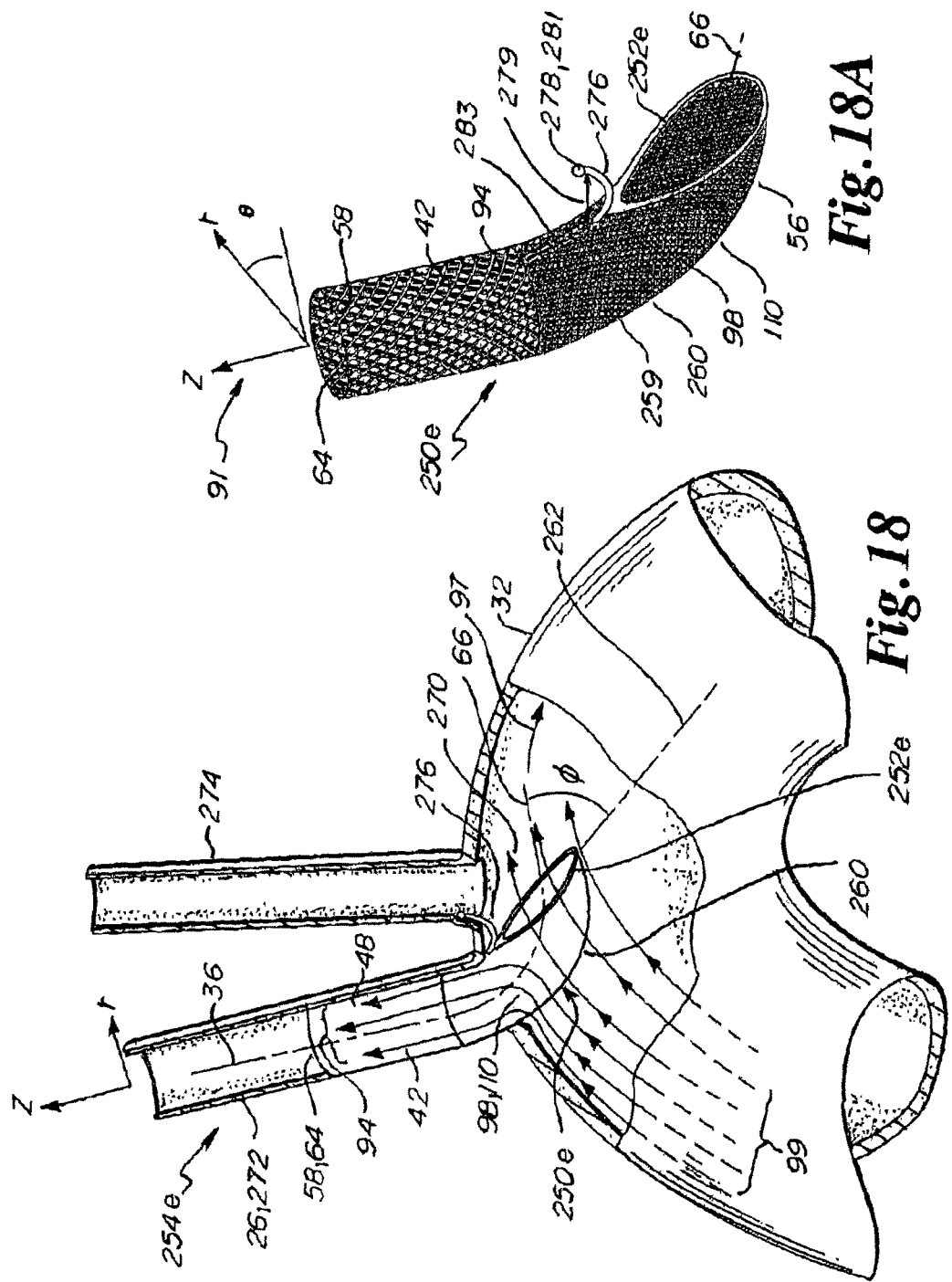

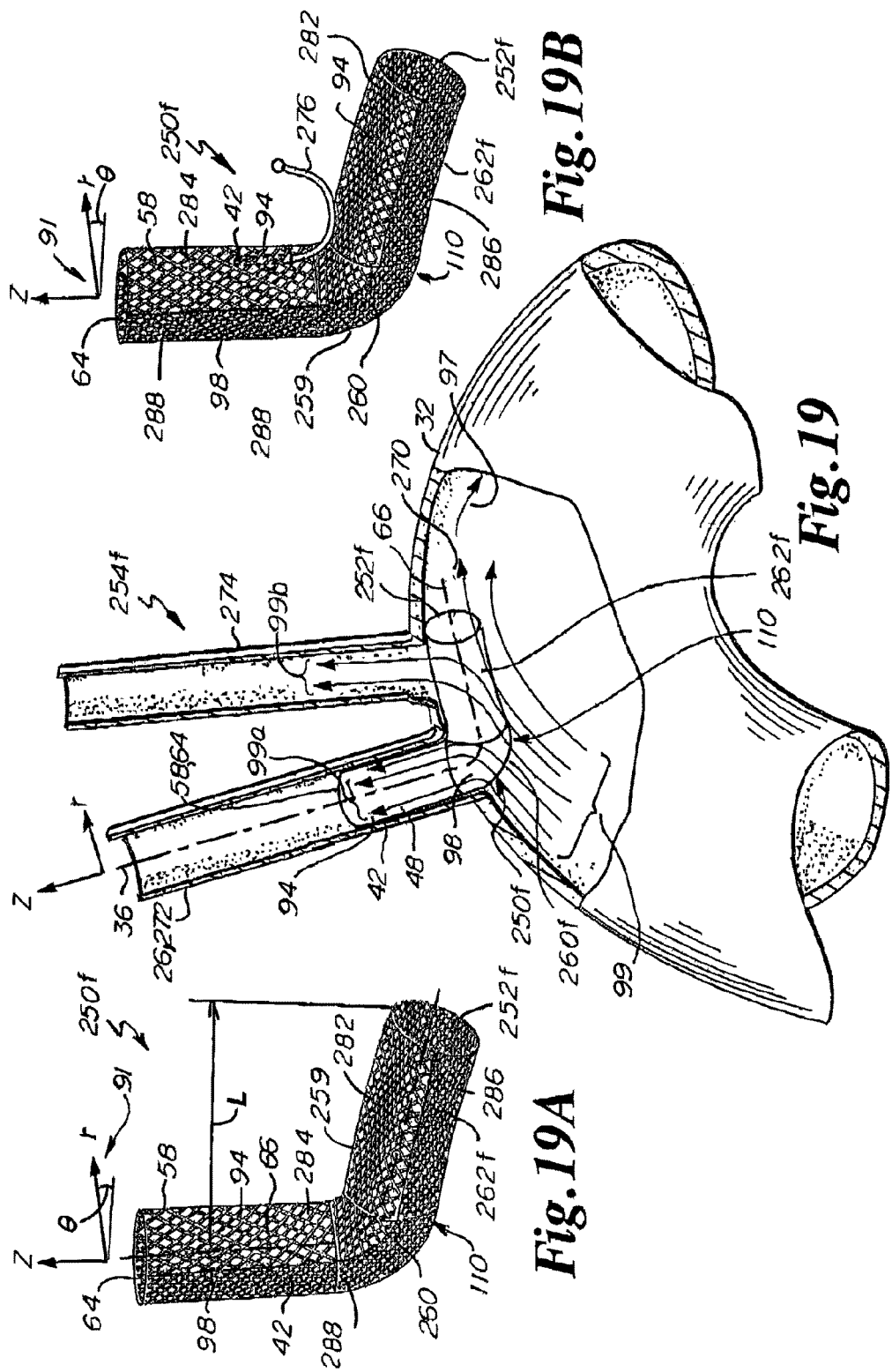

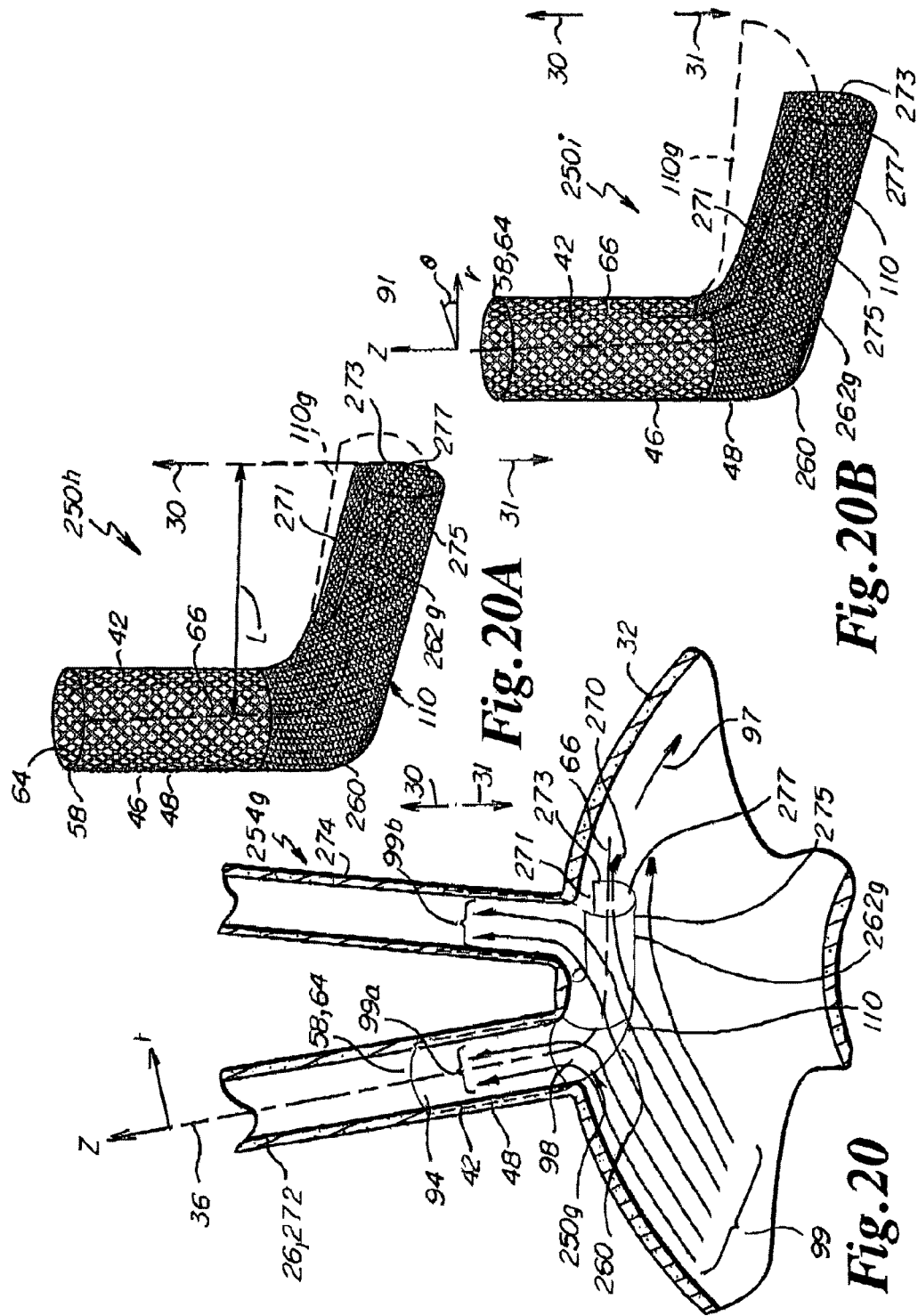

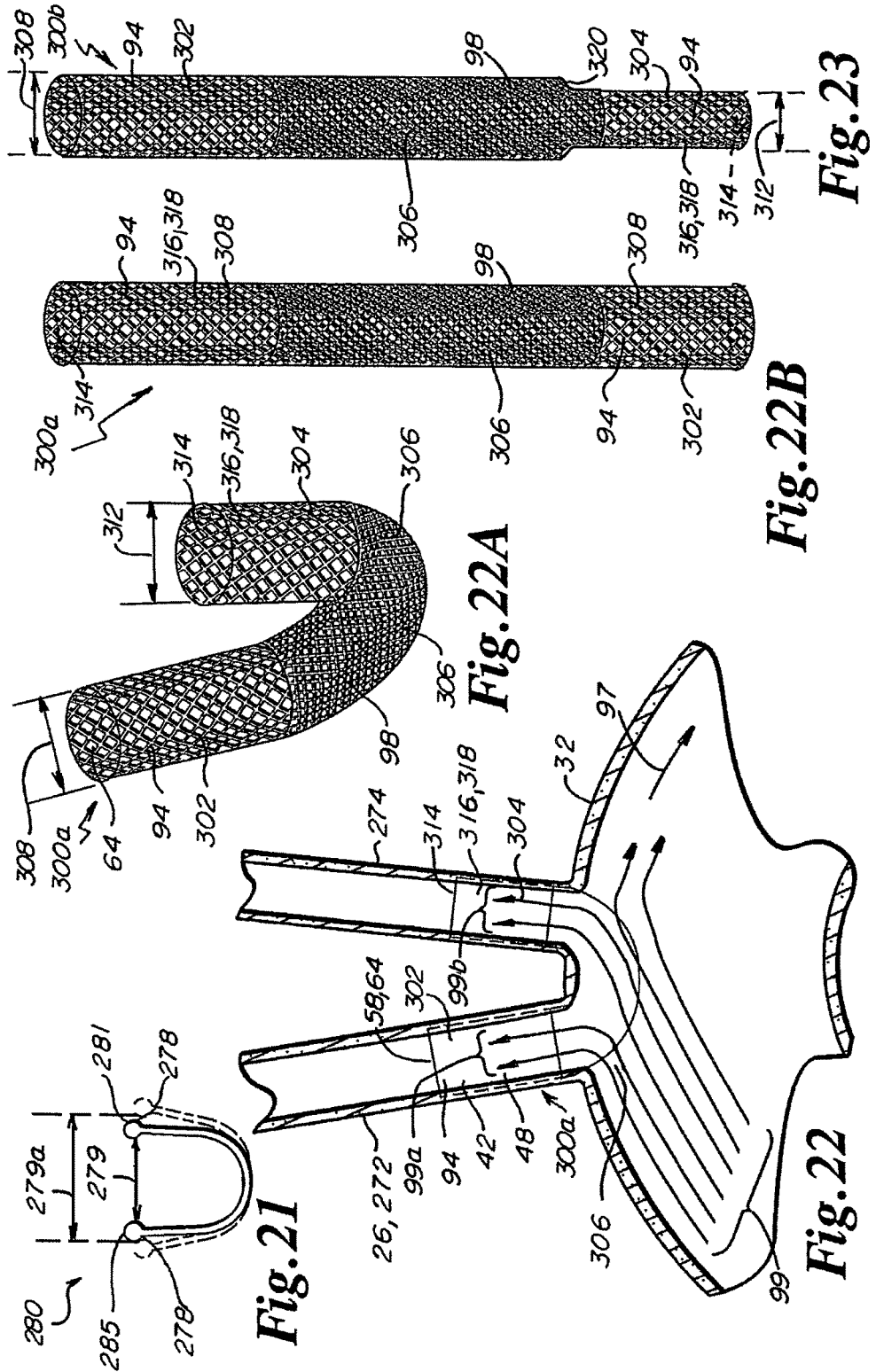

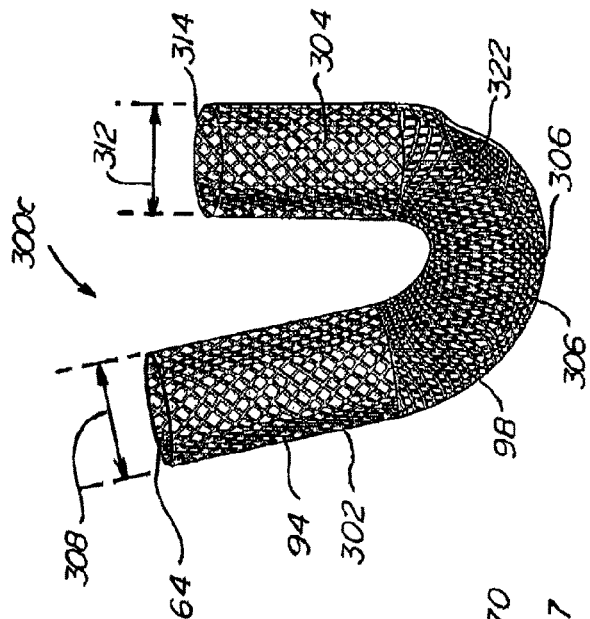
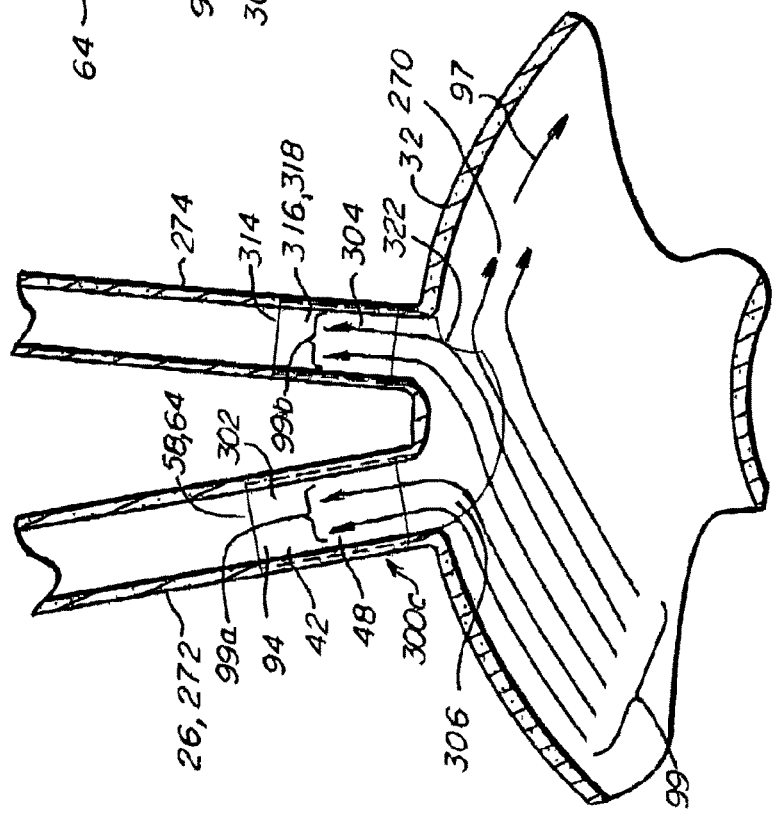
Fig. 24A
Fig. 24

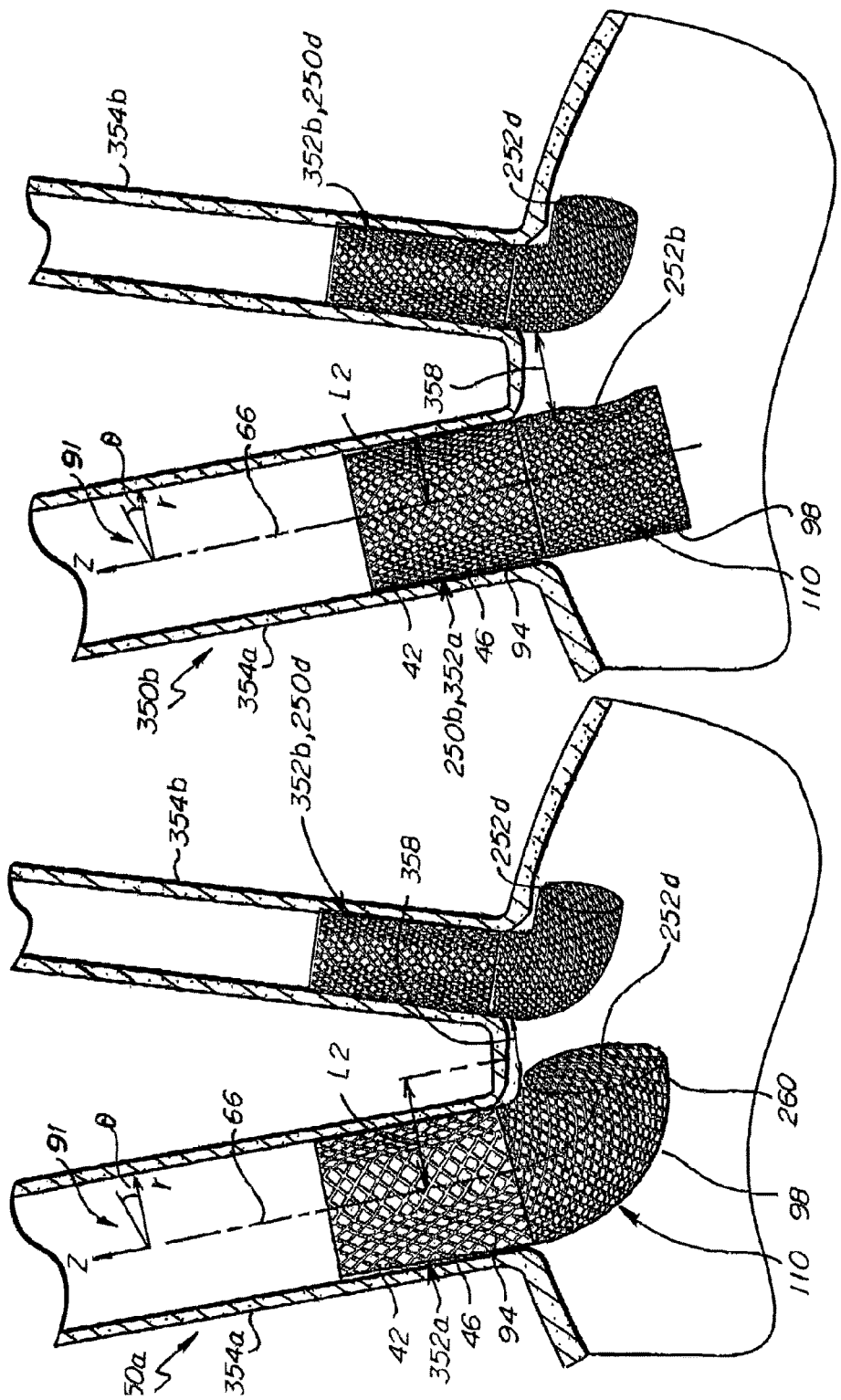

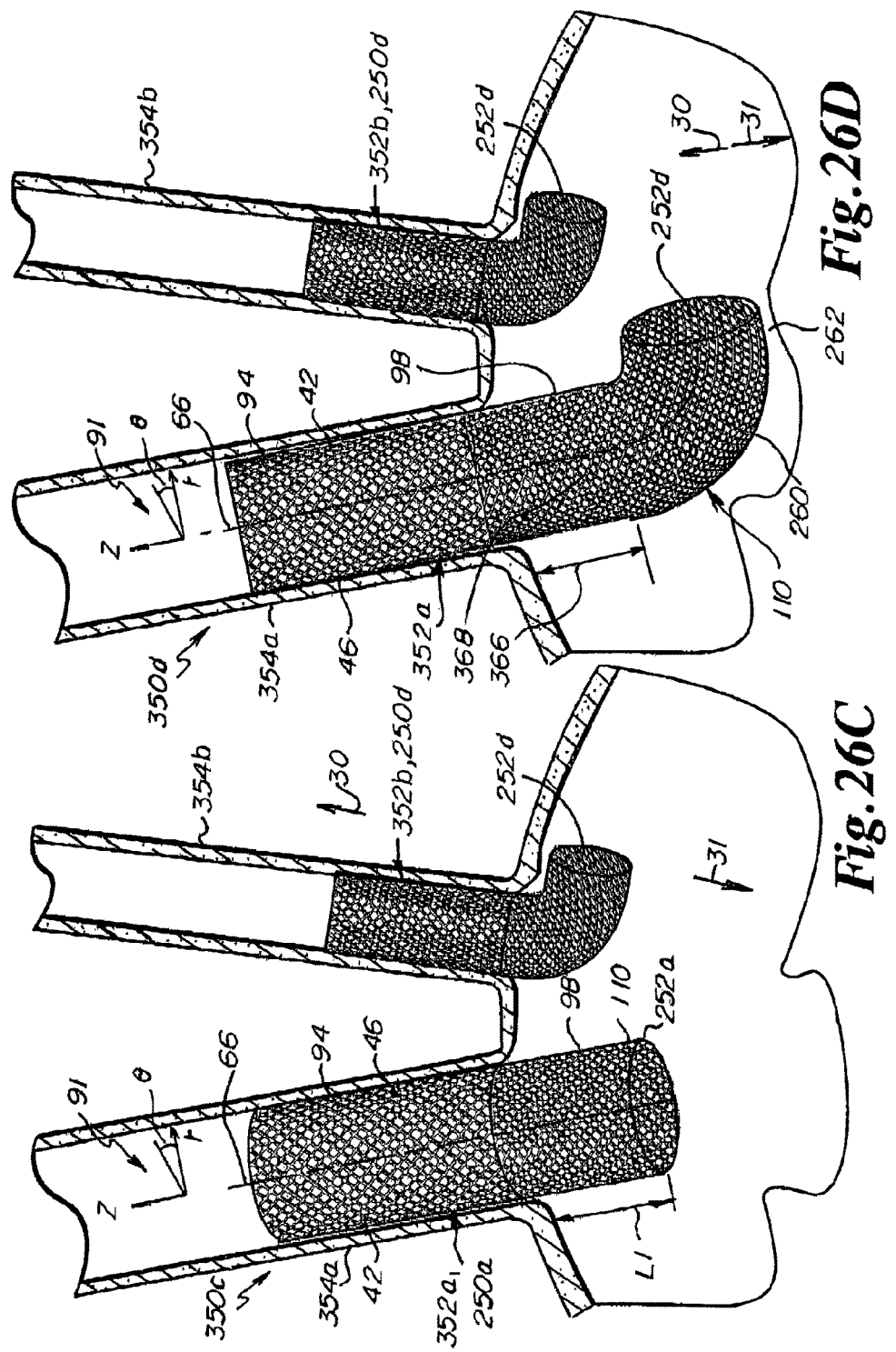

IMPLANTABLE SELF-CLEANING BLOOD FILTERS

RELATED APPLICATIONS

This patent application is a National Phase entry of PCT Application No. PCT/IB2015/001206, filed May 14, 2015, which claims the benefit of U.S. Provisional Patent Application No. 61/994,276, filed May 16, 2014, and of U.S. Provisional Patent Application No. 62/029,044, filed Jul. 25, 2014, the disclosures of which are hereby incorporated by reference in their entirety.

FIELD OF THE DISCLOSURE

The present disclosure is directed generally to implantable blood filter devices and more specifically to filter devices to protect the brain and other organs from emboli.

BACKGROUND OF THE DISCLOSURE

Various conventional devices exist to contain or control the flow of thrombic material and atheroma debris. Examples of such devices include U.S. Pat. Nos. 6,712,834 and 6,866,680 to Yassour, et al., and U.S. Pat. No. 7,670,356 to Mazzocchi et al., which disclose blood filter devices designed to capture the debris material. A concern with capture filters is that they can foul to the extent that blockage of blood flow develops, with obvious consequences. Accordingly, these devices are typically unsuitable for long term or permanent implantation.

In another approach, U.S. Pat. No. 6,258,120 to McKenzie et al., U.S. Pat. No. 8,430,904 to Belson, U.S. Pat. No. 8,062,324 to Shimon et al., and U.S. Patent Application Publication No. 2009/0254172 to Grewe are directed to aortic diverters that divert emboli away from arteries. Diverter-type devices are limited to certain artery junction structures where flow diversion is a suitable substitute for filtering, and, in many instances, do not provide a positive barrier to emboli, either by design or because of the way they are mounted within the aorta. Furthermore, these devices can foul with debris build up over time, leaving no recourse for remedying the fouling, and so are not suitable for long term or permanent implantation. Also, diverter devices that are based on anchoring in the aorta require large diameter catheters for delivery. Other diverter-type devices include U.S. Pat. No. 8,460,335 to Carpenter, are held in place by the attendant deployment means, and thus suitable only for temporary service.

A blood filter device that overcomes the aforementioned shortcomings of conventional blood filters and aortic diverters would be welcomed.

SUMMARY OF THE DISCLOSURE

In various embodiments, a blood filter device is disclosed that combines the advantages of a positive blood filter device with the diversionary advantages of aortic diverters to provide a blood filter device that is occlusion-resistant. In some embodiments, the blood filter device is suitable for either temporary filtering or permanent or long term filtering. In one embodiment, the blood filter device can be withdrawn from the artery using a percutaneous technique. In some embodiments, the device can be reconfigured or opened up in situ to re-establish normal blood flow through the artery in the unlikely case of thrombotic or other blockage of the filter.

In some embodiments, the disclosed blood filter is inserted into the ostium (take-off) of the major body artery, e.g., a branch of the aorta to filter the blood flowing into this artery from the aorta. In one embodiment, the device is designed in a way that, when inserted into the ostium of the branch of the aorta, a filter cap of the device is located in the same geometrical plane as the take-off (ostium) of the artery. In other embodiments, the filter cap protrudes into the lumen of the aorta. The projection of the filter cap into lumen of the aorta enables self-cleaning of the filter cap by the aorta blood flow that effectively purges the filtering surface of thrombi and atheroma debris and prevents the filter cap from being blocked by such emboli. This preserves the patency of the filter. In certain embodiments, the blood filter provides a physician with a capability of opening the filter in situ and with minimal invasiveness in the event that the filter cap becomes significantly blocked by thrombi and/or debris and/or other embolic material.

In various embodiments, the occlusion resistant aspects of the blood filter device is also augmented by the orientation of the filtering cap relative to the direction of the blood flow. The filter cap of the filter device is located upstream of the anchor portion, as compared with prior art devices where filter is located downstream of a stent. In addition, certain embodiments implement a convex surface that bows in the direction of the blood flow, whereas other prior art filters present a concave surface relative to blood flux.

In various embodiments, the filter device defines both a coarse porosity and a fine porosity. The coarse porosity can promote tissue ingrowth for anchoring of permanently implanted devices; the fine porosity is suitable for the filtering function.

In some embodiments, a filter device is configured to be inserted in one artery and oriented to cover an ostium of a second adjacent artery. Optionally, various embodiments are configured to be inserted into both ostia of the adjacent arteries, with a tubular filter portion being supported therebetween. Such filter devices provide filtering or diversionary protection from incursion of thrombi and atheroma debris to the adjacent arteries.

The blood filter device of various embodiments can be left in an aortic branch take-off for a short period of time (hours, days, or weeks) in case of acute interventional procedure such as percutaneous aortic valve replacement (TAVI), heart or aortic surgery, AF ablation procedure, and treatment of infectious endocarditis. For short-term uses, the device could be withdrawn using percutaneous technique at a physician's discretion after implantation. Optionally, some embodiments can be utilized as a permanent implant in patients posing a chronic risk of embolic complications such as atrial fibrillation, degenerative and autoimmune valvular disease, atheromatous disease of aorta, patent foramen ovale or recurrent stroke of unknown origin.

Various embodiments of the disclosed filter device can be put into any branch of the aorta, including brachiocephalic arteries, as well as renal, and mesenteric arteries.

Structurally, various embodiments of a blood filter for filtering blood entering an artery are disclosed, comprising a body that includes an anchor portion defining a flow outlet port at a first end of the body and including a porous wall that defines a first porosity, and a filter portion that extends from the anchor portion and includes a porous wall that defines a second porosity, the second porosity being less than the first porosity. In one embodiment, the filter portion defines a second end of the body, the second end defining a bypass aperture.

In some embodiments, the body defines a straight cylinder. Optionally, the blood filter comprises one of a flange and a plurality of protrusions extending laterally outward from the body. In some embodiments, the one of the flange and the plurality of protrusions are disposed proximate a junction between the anchor portion and the filter portion.

In other embodiments, the body defines a curved cylinder about a curved body axis. Optionally, a first tangential portion of the filter portion defines the second porosity, and a second tangential portion of the filter portion defines the first porosity. In one embodiment, the bypass aperture lies substantially on a plane, and the curved body axis intersects the plane at an acute angle. Various embodiments optionally include a centering hook structure coupled to the anchor portion that projects laterally outward from the anchor portion.

In various embodiments of the disclosure, a filter cap is coupled to the filter portion. A maximum lateral dimension of the filter cap can be less than or equal to a diameter of the body, with the filter cap being planar. For some embodiments, the filter portion defines a lateral bypass aperture. Optionally, the blood filter further comprises a shroud surrounding the lateral bypass aperture.

In various embodiments, the filter cap is bulbous. Optionally, the filter cap also includes a hub that is removable for defining an open configuration of the blood filter, the open configuration enabling blood to flow through the anchor portion unfiltered. Optionally, the filter cap defines a bypass aperture. In one embodiment, the anchor portion is concentric about a central axis, and the bypass aperture defines a normal vector having a lateral component relative to the central axis. In one embodiment, the filter cap includes a cover that covers the bypass aperture, the cover being removable for selective access to the blood filter through the bypass aperture. Optionally, the cover includes a hub. In various embodiments, the filter cap and the body are unitary. In some embodiments, the body includes a flange portion, the bulbous portion being configured to register against the flange portion. Optionally, the flange portion and the body are unitary. In certain embodiments, a stem portion extends from the bulbous portion, the stem portion being dimensioned for removable insertion into the body. Optionally, the stem portion and the bulbous portion are unitary.

In various embodiments of the disclosure, a dual anchor configuration is disclosed, wherein the body further comprises a second anchor portion defining a second flow outlet port and including a porous wall that defines a third porosity. The third porosity can be configured to be substantially the same as the first porosity. In one embodiment, the anchor portion is dimensioned for anchoring to an innominate artery and the second anchor portion is dimensioned for anchoring to a left carotid artery. Optionally, the anchor portion defines a first diameter, the second anchor portion defines a second diameter, the second diameter being less than the first diameter.

The filter portion of the dual anchor embodiments can also define a lateral bypass aperture. Optionally, the filter comprises a shroud surrounding the lateral bypass aperture. In various embodiments, the second anchor portion extends from a second end of the filter portion, the second end of the filter portion being opposed to the first end of the filter portion. In some embodiments, the filter portion is configured to define a U-shape in an implanted configuration wherein the filter portion is inferior to both the anchor portion and the second anchor portion in the implanted configuration. Optionally, all of the U-shape has the second porosity.

For various embodiments, the filter portion is dimensioned to extend from an ostium of an innominate artery to cover an ostium of a left carotid artery. The anchor portion can be concentric about a central axis, with the filter portion including an elbow-shaped portion and extending lateral to the anchor portion to define a lateral dimension referenced from the central axis, the lateral dimension being in a range of 20 mm to 60 mm inclusive; in some embodiments, in a range from 20 mm to 40 mm inclusive; in some embodiments, in a range from 20 mm to 35 mm inclusive. (Herein, a range that is said to be "inclusive" includes the endpoint values of the stated range.) In some embodiments, the filter portion defines a diameter in a range of 6 mm to 20 mm inclusive; in some embodiments, in a range from 8 mm to 18 mm inclusive; in some embodiments, in a range from 10 mm to 15 mm inclusive.

In various embodiments, the body portion comprises one of a bio-absorbable alloy and a bio-absorbable polymer. Optionally, the body portion comprises a material selected from the group consisting of stainless steel, platinum, platinum-iridium alloys, nickel-cobalt alloys, nickel-titanium alloys, magnesium based alloys, polyethylene terephthalate, polyurethane, and polylactic acid based polymers.

In some embodiments, the porous wall of the filter portion defines a porosity in the range of 50% to 98% inclusive; in some embodiments, in a range from 60% and 95% inclusive; in some embodiments, in a range from 70% and 95% inclusive; in some embodiments, in a range from 75% and 90% inclusive. In some embodiments, the porous wall of the anchor portion defines a porosity in the range of 60% to 98% inclusive; in some embodiments, in a range from 70% and 95% inclusive; in some embodiments, in a range from 75% and 95% inclusive; in some embodiments, in a range from 80% and 95% inclusive. Optionally, the porous wall of the body is a meshed structure. The porous wall of the filter portion can also be configured as a meshed structure. Optionally, the filter portion defines pore sizes in a range from 40 μm to 1000 μm inclusive; in some embodiments, in a range from 300 μm to 1000 μm inclusive; in some embodiments, in a range from 400 μm to 800 μm inclusive; in some embodiments, in a range from 400 μm to 600 μm inclusive; in some embodiments, in a range from 600 μm to 800 μm inclusive; in some embodiments, in a range from 500 μm to 700 μm inclusive.

Various embodiments of a filter device disclosed herein include a body comprising a porous wall and having a proximal end and a distal end and defining a body axis that passes through the proximal end and the distal end. A filter cap is operatively coupled to the proximal end of the body, the filter cap being either planar or convex relative to the body axis in a direction that extends away from the body. The body can optionally define a radial dimension that is larger than a nominal dimension of an artery designated for implantation. In one embodiment, the body includes an anchor portion that comprises a shape memory material.

In some embodiments, the proximal end of the porous wall is configured to filter blood passing therethrough. By configuring the proximal end as a filter, an increased margin of tolerance is realized for placement of the device. That is, absolute registration of the filter cap at all points on the circumference of the ostium is not required to achieve the full effect of filtering and/or diversion.

In various embodiments, the filter cap includes a bulbous portion and can also include a hub portion. In one embodiment, removal of the hub portion configures the filter device in an open configuration whereby the filter cap is open to enable blood flow through the body unfiltered. In another embodiment, the filter cap is detachable from the body to configure the filter device in an open configuration whereby the filter cap is open to enable blood flow through the body unfiltered. The hub portion can include a disc portion that is seated within the bulbous portion. In some embodiments, the bulbous portion is resilient. In one embodiment, the hub portion is replaceable.

In various embodiments of the disclosure, a blood filter is disclosed comprising a body that includes: an anchor portion including a first end that defines a flow outlet port, the flow outlet port being normal to a body axis, the anchor portion including a first porous wall; and a filter portion that extends from the anchor portion, the filter portion including a second porous wall and defining a lateral bypass aperture proximate a second end of the body. Optionally, the filter portion includes an elbow portion the second end of the body, the elbow portion defining the lateral bypass aperture. Optionally, the filter portion includes an extension portion that extends laterally from the elbow portion, the extension portion defining the lateral bypass aperture. Optionally, the first porous wall and second porous wall are of substantially equal porosity; alternatively, the first porous wall defines a first porosity, the second porous wall defines a second porosity, the first porosity being greater than the second porosity. In one embodiment, the first porosity defines a first average pore size, and the second porosity defines a second average pore size, the second average pore size being less than the first average pore size.

In various embodiments of the disclosure, a blood filtering system is disclosed, comprising a plurality of filter devices, each including a body. Each body includes an anchor portion defining a flow outlet port at a first end of the body, the outlet port being normal to a first axis, the anchor portion including a porous wall. A filter portion extends from the anchor portion, the filter portion including a porous wall and defining a bypass aperture at a second end of the body, the bypass aperture being normal to a second axis, the second axis defining a non-zero angle with respect to the first axis. In some embodiments, the non-zero angle of each of the plurality of filter devices is in a range from 60° and 120° inclusive. In certain embodiments, the non-zero angle of each of the plurality of filter devices is substantially 90°. Optionally, the filter portion of each of the plurality of filter devices includes an elbow-shaped portion that depends from the anchor portion, the elbow-shaped portion defining the bypass aperture. Optionally, each of the plurality of filter devices includes an elbow-shaped portion that depends from the anchor portion and an extension portion that extends from the elbow-shaped portion, the extension portion defining the bypass aperture. For various embodiments, the bypass aperture is centered on the second axis at a distance in a range of 20 mm to 60 mm inclusive from the first axis. For some embodiments, the bypass aperture is centered on the second axis at a distance in a range of 6 mm to 10 mm inclusive from the first axis. Optionally, the porous wall of the anchor portion of each of the plurality of filter devices defines a first average pore size, and the porous wall of the filter portion of each of the plurality of filter devices defines a second average pore size, the second average pore size being less than the first average pore size.

In various embodiments, a slot is defined on a superior face of the filter portion, the filter portion thereby defining a channel opening at a lateral end of the filter portion. The slot extends through the elbow-shaped portion and into the anchor portion.

In another embodiment of the disclosure, a method for filtering blood flowing into an artery is presented. The method can comprise one or more of the following:
   providing a filter device having an body and a filter cap, the body comprising an anchor portion having a porous wall, a proximal end, and a distal end, the body defining a body axis that passes through the proximal end and the distal end, the filter cap being operatively coupled to the proximal end of the body, the filter cap being either planar or convex relative to the body axis in an upstream direction;
   disposing the filter device in the artery so that the filter cap is upstream of the anchor portion;
   positioning the filter cap in a geometrical plane defined by an ostium of an artery;
   positioning the filter cap in an upstream direction from a geometrical plane defined by an ostium of an artery, such that a wall portion of the proximal end of the body filters blood passing therethrough;
   removing the hub portion to open the filter cap, for example by unscrewing the hub from the filter cap;

The filter cap provided in the step of providing a filter device can comprise a meshed structure. In one embodiment, the meshed structure is a flat mesh.

BRIEF DESCRIPTION OF THE DRAWINGS

FIG. 1A is an enlarged, schematic view of the filter device of FIG. 1 in an implanted configuration in an embodiment of the disclosure;

FIG. 1B is a perspective, distal end view of the filter device of FIG. 1A in isolation;

FIG. 2 is a schematic view of a filter device in an implanted configuration in an embodiment of the disclosure;

FIG. 2A is a perspective view of a filter device having a porosity that varies axially in an embodiment of the disclosure;

FIG. 3 is a sectional view of a filter device in an implanted configuration, the filter device having a porosity that varies tangentially in an embodiment of the disclosure;

FIG. 3A is a perspective, distal end view of the filter device of FIG. 3 in isolation;

FIG. 4 is a schematic view of a filter device having a convex filter cap in an implanted configuration in an embodiment of the disclosure;

FIG. 5 is a perspective view of a filter device having lateral protrusions in an implanted configuration in an embodiment of the disclosure;

FIG. 6 is a perspective view of a filter device having a bulbous filter cap in an implanted configuration in an embodiment of the disclosure;

FIG. 7 is a perspective view of the filter of FIG. 6 in an open configuration;

FIGS. 8A through 8F are perspective views of a fabrication of filter devices having bulbous filter caps in embodiments of the disclosure;

FIG. 17 is a cutaway perspective view of a filter device in an implanted configuration the filter device defining a curved cylinder with a lateral bypass aperture in an embodiment of the disclosure;

FIG. 17A is a perspective view of the implanted filter device of FIG. 17 in isolation;

FIG. 18 is a cutaway perspective view of a filter device in an implanted configuration, the filter device defining a curved cylinder with a lateral bypass aperture in an embodiment of the disclosure;

FIG. 18A is a perspective view of the implanted filter device of FIG. 18 in isolation;

FIG. 19 is a cutaway perspective view of a filter device in an implanted configuration, the implanted filter device defining a curved cylinder that defines a lateral bypass aperture and having a porosity that varies tangentially in an embodiment of the disclosure;

FIG. 19A is a perspective view of the implanted filter device of FIG. 19 in isolation;

FIG. 19B is a perspective view of the filter device of FIG. 19 with optional centering hook in an embodiment of the disclosure;

FIG. 20 is a cutaway perspective view of a filter device in an implanted configuration, the filter device defining a curved cylinder with a slot and channel in an embodiment of the disclosure;

FIGS. 20A and 20B depict the filter device of FIG. 20 with differing slot lengths in embodiments of the disclosure;

FIG. 21 is a perspective view of a detached centering hook in an embodiment of the disclosure;

FIG. 22 is a sectional view of a dual anchor filter device in an implanted configuration in an embodiment of the disclosure;

FIG. 22A is a perspective view of the implanted dual anchor filter device of FIG. 22 in isolation;

FIG. 22B is a perspective view of the dual anchor filter device of FIG. 22A in a fully expanded configuration prior to implantation in an embodiment of the disclosure;

FIG. 23 is a perspective view of a fully expanded dual anchor filter device having anchor portions of different diameters in an embodiment of the disclosure;

FIG. 24 is a sectional view of a dual anchor filter device with a lateral bypass aperture in an implanted configuration in an embodiment of the disclosure;

FIG. 24A is a perspective view of the dual anchor filter device of FIG. 24 in the implanted configuration in isolation;

FIGS. 26A through 26D is a sectional view of alternative double filter arrangements in embodiments of the disclosure.

DETAILED DESCRIPTION OF THE DRAWINGS

Figure 1:
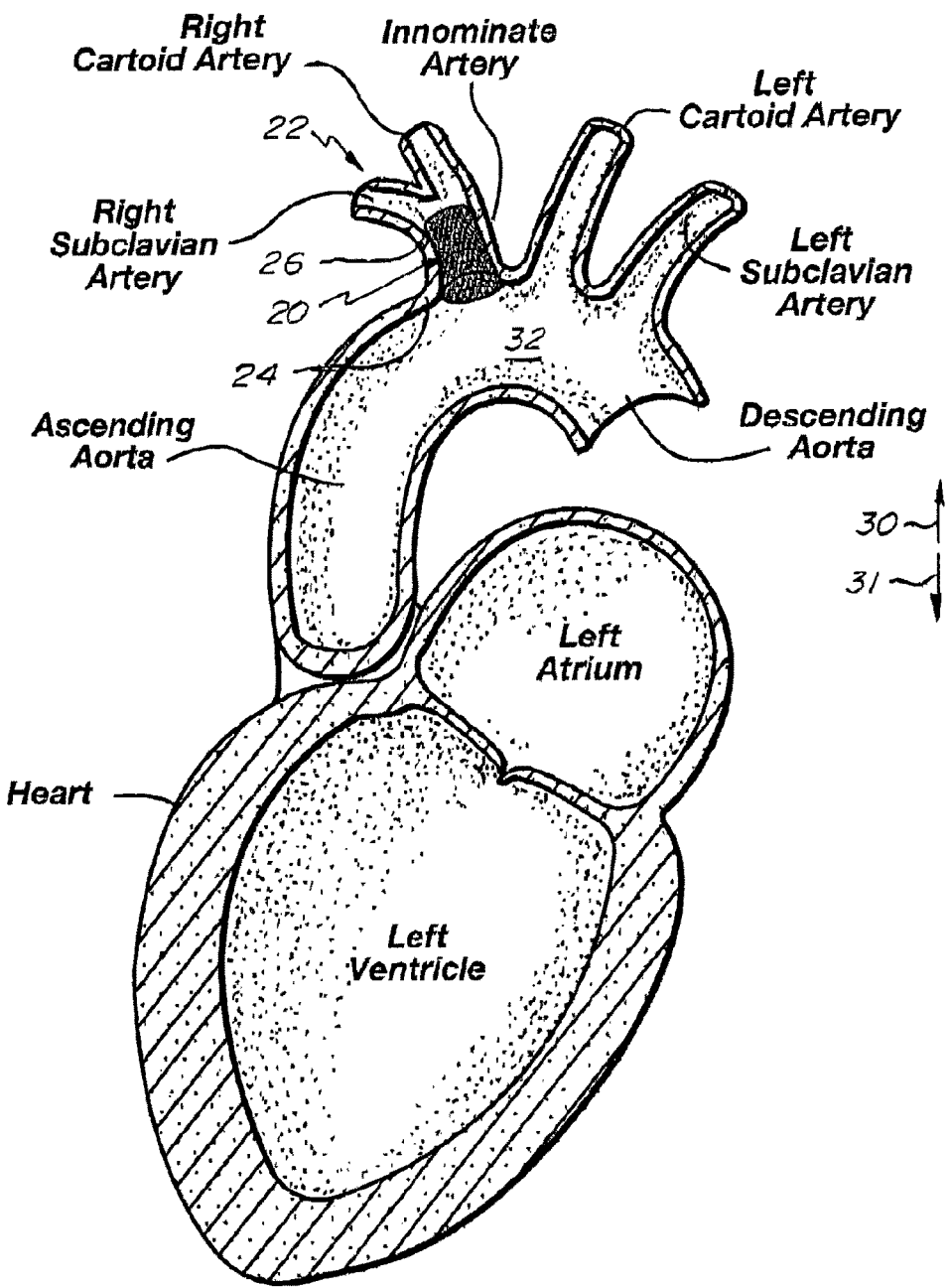
FIG. 1 is a frontal cutaway view of a human heart with a filter device implanted in an embodiment of the disclosure.
Figures 1C, 1D:
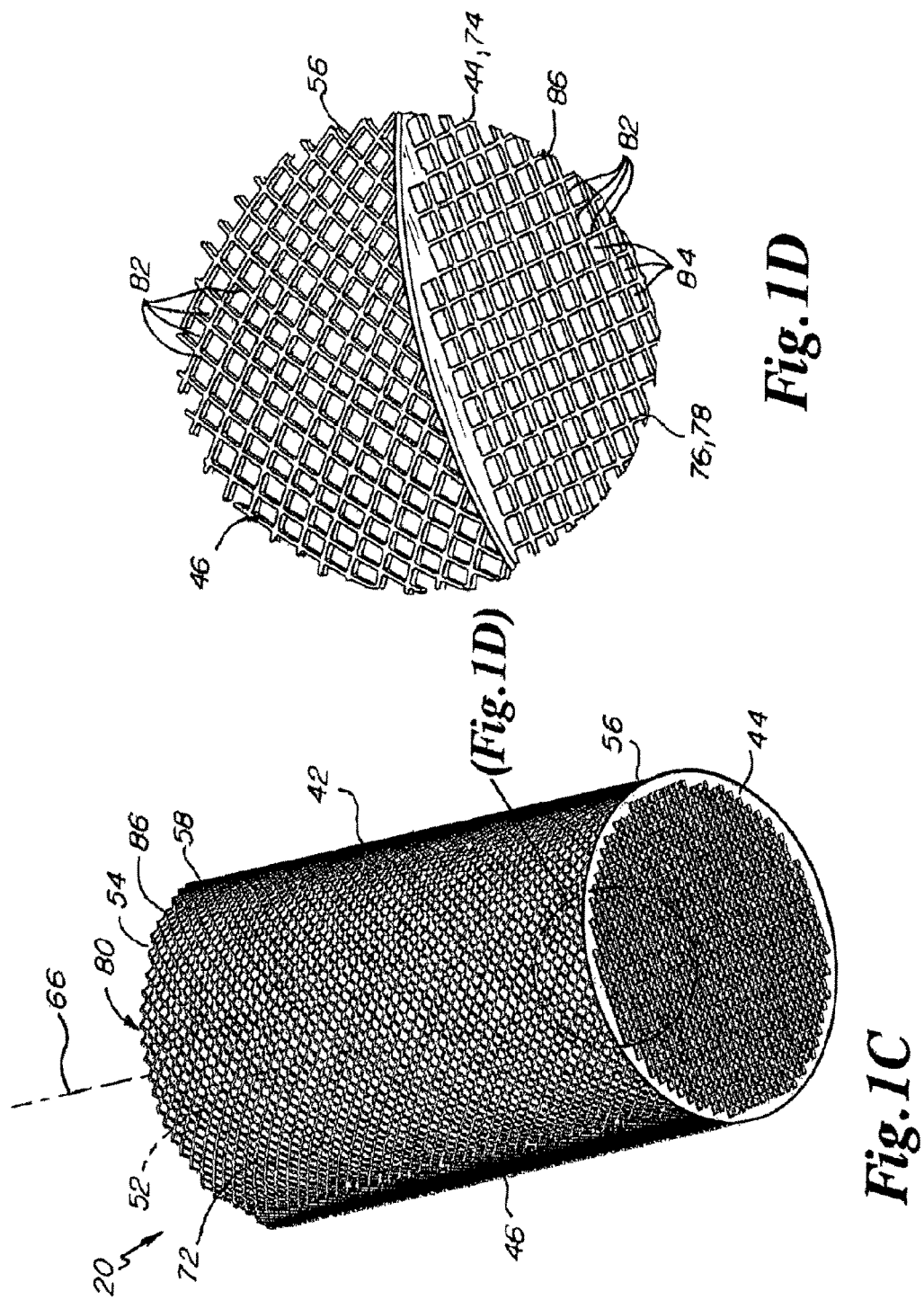
FIG. 1C is a is a perspective, proximal end view of the filter device of FIG. 1A in isolation.
FIG. 1D is an enlarged, partial view of FIG. 1B in an embodiment of the disclosure.

Referring to FIGS. 1 through 1D, a filter device 20 is depicted in an implanted configuration 22 and in isolation in an embodiment of the disclosure. The filter device 20 is depicted as being implanted in the ostium 24 (take-off) of an artery 26, and more specifically into a branch 28 of an aortic arch 32 to filter the blood flowing into the artery 26 from the aortic arch 32. The artery 26 can be characterized as having an effective flow radius 34 relative to a central flow axis 36. The FIG. 1 depiction also presents, without limitation, various candidate arteries for implantation of the filter device 20, including the innominate artery (and attendant right carotid and right subclavian arteries), the left carotid artery, and the left subclavian artery. The FIG. 1 depiction also identifies a superior direction 30 and an inferior direction 31 of the anatomy.

The filter device 20 includes a body 46 and a filter cap or element 44. In one embodiment, the body 46 includes a porous wall 48 having an inner surface 52, an outer surface 54, a proximal end 56 and a distal end 58, the distal end 58 defining an opening 62 that serves as a flow outlet port 64. (Herein, "proximal" and "distal" are relative terms that refer generally to the direction of blood flows, with proximal being generally upstream from distal.) In various embodiments, the flow outlet port 64 is open, i.e., does not include a filtering medium that transverses the body axis 66. In one embodiment, the proximal end 56 of the body 46 is capped by the filter cap 44. The body 46 defines a body axis 66 that passes through the proximal and distal ends 56 and 58 of the body 46. The outer surface 54 defines a maximum outer radial dimension 68 relative to the body axis 66. In one embodiment, the body 46 is effectively a stent, comprising a meshed structure 72 that can be substantially cylindrical in shape, as depicted. In various embodiments, the body is dimensioned to provide an interference fit between an arterial wall 74 and the body 46 when in an expanded state to anchor the filter device 20 in the implanted position. Optionally, the body 46 can be balloon expandable or self-expanding.

The filter cap 44 can comprise a substantially planar disc 74 that covers the proximal end 56 of the body 46. In one embodiment, the filter cap 44 is unitary with the proximal 56 end of the body 46. Herein, a cap that is "unitary" with the body is integrally formed with the body, without need for a separate connection step to secure the cap to the body. Alternatively, the filter cap 44 can be formed as a separate component that is then joined to the body, for example using mechanical connections or with an adhesive or by a fusion or welding process. In various embodiments, the filter cap 44 comprises a meshed structure 76.

The meshed structures 72, 76 of the body 46 and the filter cap 44, when utilized, can be a flat mesh 78, as depicted in FIG. 1D. The flat mesh 78 can be comprised of a web 80 of cross-members 82 formed of a substantially sheet-like structure 86 and that define a plurality of openings 84 in a matrix arrangement. The flat sheet structure can be rolled into the cylindrical shape either before or after the formation of the openings 84. Alternatively, instead of a flat sheet, the openings 84 can be formed in a hollow cylinder to provide a uniform body thickness (i.e., no overlap). The plurality of openings 84 can be rectangular in shape, as depicted in FIG. 1D, each opening 84 being surrounded and defined by adjacent cross-members 82 of the web 80, and such that the cross-members 82 intersect at substantially right angles. Other geometries for the openings 84 and cross-members 82 are also contemplated, including but not limited to parallelograms (i.e., where cross-members intersect at non-right angles) or circular apertures formed in the sheet-like structures 86. The openings 84 of the flat mesh 78 can be formed by techniques available to the artisan, such as laser machining, electro-discharge machining (EDM), or mold injections techniques. Alternatively, the meshed structures 86 can comprise a woven mesh (not depicted), wherein the cross-members 82 comprise interwoven strands.

The meshed structures 86 can be characterized by mesh sizing parameters that can include the number of cross-members 82 per lineal length, a projected width of the cross-members (defined as the width of the cross-member as projected in a direction normal to the meshed structures), and/or an open fraction (defined as the open area of the meshed structure per unit area of meshed structure). A non-limiting example of the mesh sizing parameters suitable for the anchor portion 42 of some embodiments of the present disclosure include pore sizes in a range from 500 μm to 5000 μm inclusive; in some embodiments, in a range from 500 μm to 3000 μm inclusive; in some embodiments, in a range from 800 μm to 2000 μm inclusive; in some embodiments, in a range from 800 μm to 1500 μm inclusive; in some embodiments, in a range from 1000 μm to 1500 μm inclusive. A non-limiting example of the mesh sizing parameters suitable for the filtering portion 110 of some embodiments of the present disclosure include pore sizes in a range from 40 μm to 1000 μm inclusive; in some embodiments, in a range from 300 μm to 1000 μm inclusive; in some embodiments, in a range from 400 μm to 800 μm inclusive; in some embodiments, in a range from 400 μm to 600 μm inclusive; in some embodiments, in a range from 600 μm to 800 μm inclusive; in some embodiments, in a range from 500 μm to 700 μm inclusive. In some embodiments, the open fraction of the anchor portion 42 and/or the filter portion 110 is in a range from 50% and 95% inclusive; in some embodiments, in a range from 60% and 90% inclusive; in some embodiments, in a range from 70% and 90% inclusive; in some embodiments, in a range from 75% and 85% inclusive. In embodiments employing cross-members 82 of substantially uniform width, a non-limiting example of the projected width of the cross-members 82 is between 40 μm to 1000 μm inclusive; in some embodiments, in a range from 300 μm to 1000 μm inclusive; in some embodiments, in a range from 400 μm to 800 μm inclusive; in some embodiments, in a range from 400 μm to 600 μm inclusive; in some embodiments, in a range from 600 μm to 800 μm inclusive; in some embodiments, in a range from 500 μm to 700 μm inclusive. For embodiments implementing woven strand meshed structures, the projected width of the cross-members is taken as the diameter of the woven strands.

The porous wall 48 and/or filter cap 44 can be characterized as having a "porosity." Herein, "porosity" is defined as the ratio of the void volume to the total volume of a representative sample of the medium. For meshed structures 86, the total volume of a unit area of mesh is defined by the overall thickness of the unit area of the meshed structure 86 multiplied by that unit area. The void volume is the volume complementary to the volume of the cross-members 82 per unit area of meshed structure 86 (i.e., the volume not occupied by the cross-members 82 of the meshed structure 86 per unit area). In addition to mesh structures, "porosity" also describes open cell structures, which can also be utilized for the porous wall 48 and/or various filter caps.

The anchor portion 42 and/or filter cap 44 can include one or several of a number of materials available to the artisan, including metals (e.g., stainless steel, platinum, platinum-iridium alloys, nickel-cobalt alloys, nickel-titanium alloys (e.g., NITINOL), and bio-absorbable alloys such as magnesium based alloys) and various polymers (e.g., polyethylene terephthalate (PET), polyurethane, and bio-absorbable polymers such as polylactic acid based polymers).

In use, in various embodiments, the filter device 20 is inserted into the ostium 24 (take-off) of the artery 26, and more specifically into the branch 28 of the aortic arch 32 to filter the blood flowing into the artery 26 from the aortic arch 32, as depicted in FIG. 1A. In one embodiment, the filter device 20 is designed in a way that, when inserted into the ostium 24 of the branch 28 of the aortic arch 32, the filter cap 44 is located in the same geometrical plane as the take-off 24 of the artery 26.

In various embodiments, the body 46 includes an anchor portion 42. The anchor portion 42 is so-named because it is configured to anchor the body 46 to the artery 26. In some embodiments, the anchor portion 42 is the same length as the body 46; that is, the entire body 46 can be configured as an anchor portion 42. In various embodiments, the anchor portion 42 comprises an elastic material such as cobalt-chromium-nickel alloys (e.g., ELGILOY), platinum-iridium alloys or nickel-titanium alloys. In this case the device could be seated in the artery using the self-expanding force of the elastic material. In other embodiments, the anchor portion 42 can be comprised of a material such as stainless steel or cobalt-chromium alloys and can be deployed using the plastic deformation of those materials. In this case the device could be delivered into the artery using expansion balloon (like a balloon expandable stent). In some embodiments, the anchor portion 42 is comprised of a material that is pliable but having substantial "shape memory" (i.e., having a tendency to return to its original shape after deformation). Materials having these characteristics include certain alloys such as nickel-titanium. In other embodiments, the anchor portion 42 can be comprised of a material that is pliable but has little or no shape memory. Materials having these characteristics include polymers generally as well as malleable metals generally.

The body 46 can be tailored so that, in an implanted (expanded) configuration, the diameter of the body 46 (i.e., twice the outer radial dimension 68) is suited for implantation in a particular artery. For example: Anchor portions 42 tailored for innominate arteries may have diameters in one of the following ranges: 9 to 14 mm inclusive; 10 mm to 14 mm inclusive; 11 mm to 13 mm inclusive. Anchor portions 42 tailored for subclavian arteries may have diameters in one of the following ranges: 6 to 12 mm inclusive; 7 mm to 11 mm inclusive; 8 mm to 10 mm inclusive. Anchor portions 42 tailored for carotid arteries may have diameters in one of the following ranges: 5 mm to 10 mm inclusive; 5 mm to 9 mm inclusive; 6 mm to 8 mm inclusive.

Functionally, the method of implantation of the filter device 20 can depend on the mechanical properties of the materials of which the device is composed as well as the shape memory characteristics of the anchor portion 42. For anchor portions 42 that are self-expanding or having substantial shape memory characteristics, the filter device 20 can be folded or rolled to a configuration of reduced diameter adequate for routing to the implantation site. Once in position at the implantation site, the anchor portion 42 is released. Because of the substantial elasticity or shape memory, the anchor portion 42 returns substantially to the same dimensions. For embodiments where the anchor portion 42 is oversized relative to the effective radius 34 of the artery 26, the anchor portion 42 expands or unfolds to contact the arterial wall 74, creating an interference fit that fixes the filter device 20 in place. In this type of delivery, the filter device initially is situated in a compressed form inside a delivery catheter and liberated during implantation by a withdrawal movement of the catheter relative to device.

For anchor portions 42 having little or no shape memory, the anchor portion 42 can be initially formed as being undersized relative to the effective radius 34 of the artery 26 at the implantation site. Once in position, the anchor portion 42 can be expanded, for example by way of a balloon catheter. By initially and momentarily over-expanding the anchor portion 42 to exceed the nominal dimension 34 of the artery 26 with the balloon catheter, the porous wall 48 of the anchor portion 42 is placed in interference with the arterial wall 74, fixing the filter device 20 in place. In this type of filter device, the balloon-based delivery system passes through the filter device 20, e.g., through one of the pores of the filter cap 44.

For a period of time after implantation, the filter device 20 can be readily removed from the implantation site using standard minimal invasive interventional techniques. Accordingly, the filter device 20 is suitable for temporary use. However, over time, tissue ingrowth provides further fixation of the cross-members of the porous material or mesh to the arterial wall 74, further securing the filter device 20 at the implantation site. Thus, the filer device 20 is suitable for permanent implantation.

Referring to FIG. 2, an implanted configuration 88 of the filter device 20 is depicted in an embodiment of the disclosure. In this embodiment, the filter device 20 is inserted into the ostium 24 of the branch 28 of the aortic arch 32 with the proximal end 56 and the filter cap 44 extending into the lumen of the aortic arch 32 at an immersion length L1 measured parallel to the body axis 66.

Referring to FIG. 2A, an alternative filter device 20a wherein the body 46 includes pore sizes and/or porosity that varies over the length of the anchor portion 42 is depicted in an embodiment of the disclosure. That is, the body portion 46 is characterized as having the anchor portion 42 as well as a filter portion 110. In the depicted embodiment, filter device 20a defines a first porosity 94 having a first average pore size at the distal end 58 of the body 46, while a second porosity 98 having a second average pore size is defined at the proximal end 56 of the body 46. In one embodiment, the second porosity 98 can be the same or nearly the same as the porosity or average pore size of the filter cap 44, with the first average pore sizes and porosity 94 at the distal end 58 of the body 46 being substantially greater.

Functionally, the smaller pore sizes and lower porosity at the proximal end 56 provide filtering functionality, while the larger pore sizes and higher porosity at the distal end 58 can promote tissue ingrowth to provide better anchoring for permanent implantation. Conversely, the distal end 58 of the body 46 can be of a tightly woven mesh or of a non-porous construction to inhibit tissue ingrowth, which is more suitable for temporary implantation.

Referring to FIGS. 3 and 3A, a filter device 90 is depicted in the implanted configuration 88 and in isolation in an embodiment of the disclosure. The filter device 90 includes many of the same components and aspects as the filter device 20, which are indicated with same-numbered numerical references in FIGS. 3 and 3A and/or in the following discussion thereof. A difference between the filter devices 20 and 20a and filter device 90 is that, in a standard cylindrical (r-θ-z) coordinate system 91, the porosity of the porous wall 48 varies in a tangential dimension θ about the body axis 66. As depicted, and as with the filter devices 20 and 20a, the porous wall 48 can comprise the meshed structure 72, but with mesh characteristics that vary in the tangential dimension θ. In one embodiment, an upstream face of the body 46 that faces the blood flow defines smaller pores (i.e., lower porosity) than the surface facing away from the blood flow.

In one embodiment, a first tangential portion 92 of the porous wall 48 of the body 46 defines a first porosity 94, and a second tangential portion 96 of the porous wall 48 defines a second porosity 98 (FIG. 3A), the first tangential portion 92 defining an angle θ1 about the body axis 66 and the first porosity 94 being less than the second porosity 98. In various embodiments, a non-limiting example of the angle θ1 is in the range of 60° to 270° inclusive. In one embodiment, the angle θ1 is in the range of 180° to 270° inclusive.

In operation, the filter device 90 can be oriented in a blood flow 99 (depicted as streamlines in FIG. 3) so that the first tangential portion 92 is upstream of the second tangential portion 96. The blood flow 99 is depicted as a blood cross flow having a flow vector component that is normal to the body axis 66. In one embodiment, the first tangential portion 92 of the porous wall 48 is centered tangentially about the direction of the blood flow 99 as the blood flow 99 approaches the filter device 90. In one embodiment, the immersion length L1 is sufficiently long so that a portion 99a of the blood flow 99 that enters the artery 26 first passes through the porous wall 48 of the body 46.

Functionally, the first tangential portion 92 of the filter device 90 acts as the primary filter for filtering the blood flow 99 that enters the artery 26. Debris that does not pass through the first tangential portion 92 is deflected around the filter device 90 and carried away from the artery. If, over time, the first tangential portion 92 becomes occluded to the point that not enough blood flow 99 can enter the artery 26, blood can still flow into the artery via the second tangential portion 96; the first tangential portion 92 still functions to deflect debris away from the ostium 24. The second tangential portion 96 is of higher porosity 98 to mitigate against occlusion while still providing a sufficient barrier against debris entering the filter device 90.

While varying the porosity of the porous wall 48 in the tangential dimension 9 is depicted for a straight cylinder body in FIGS. 3 and 3A, the general concept of having an upstream face of a filter body possess smaller pore sizes and/or lower porosity than on a downstream face can be implemented with any of the embodiments disclosed herein.

Referring to FIG. 4, a filter device 100 is depicted in an embodiment of the disclosure and implanted in substantially the same orientation as the implanted configuration 88 of FIG. 2. The filter device 100 includes many of the same components and aspects as the filter device 20, which are indicated with same-numbered numerical references in FIG. 4 and/or in the following discussion thereof. A difference between the filter devices 20 and 20a and filter device 100 is that a filter cap 102 of the filter device 100 of FIG. 4 presents a convex surface 104 that bows away from the proximal end 56 of the body 42 and further into the aortic arch 32 along the body axis 66.

It is noted that, in FIG. 4, the second porosity 98 (smaller mesh) of the proximal end 56 extends a ways into the artery 26. That is, the portion of the body 46 that defines the second porosity 98 is actually greater than the immersion length L1. The purpose of this arrangement is to better assure that all of the blood entering the artery 26 passes through the (finer) second porosity 98, while still providing ample length of the anchoring portion 42 to provide the desired tissue ingrowth. This arrangement can be implement for any of the various embodiments disclosed herein that include axial variation of the porosity of the body 46.

For the FIGS. 2, 3, and 4 configurations, the proximal end 56 of the body 46 extends into the lumen of the aortic arch 32. Accordingly, in addition to the anchor portion 42, the body 46 can include a filter portion 110 configured to function as a filter, i.e., having the same filtering characteristics as the filter caps 44, 102, effectively increasing filtration area. The filter flow-through area is thereby increased relative to the implanted configuration 22 of FIG. 1A, which reduces the risk of filter occlusion with emboli. The extension into the lumen of the aortic arch 32 further enables a higher degree of cross flow across the filter cap 44, 102, enhancing the self-cleaning aspect of the filter device 20, 100. The extension of the body 46 into the lumen of the aortic arch 32 further provides an advantage of protecting the filter cap 44, 102 from tissue ingrowth. The convex surface 104 of the filter cap 102 of FIG. 4 further increases the flow-through area of the filter device 100 and further enhances the cross-flow aspect, thereby further enhancing the self-cleaning attribute of the filter device.

Referring to FIG. 5, a barbed filter device 120 is depicted in an embodiment of the disclosure. The barbed filter device 120 can include many of the same aspects and characteristics as the filter device 20, as indicated with same-numbered numerical references in FIG. 5 and/or in the following discussion thereof. The barbed filter device 120 is equipped with lateral protrusions or barbs 122 or similar structures that extend radially beyond the body 46. The lateral protrusions 122 can extend from the filter cap 44 (as depicted) or can extend from the body 46 at or near the proximal end 56. In one embodiment, a dimension 124 from the body axis 66 to a radial extremity 126 of the protrusions 122 is greater than the effective radius 34 of the arterial wall 74.

Functionally, the lateral protrusions 122 interfere with the arterial wall 74 or ostium 24 when implanted. In the embodiment of FIG. 5, the interference of the protrusions with the ostium 24 effectively registers the filter cap 44 in the geometrical plane of the ostium 24. In other embodiments, protrusions 122 are located distal to the filter cap 44 (i.e., extend laterally from the body 46) to interfere with the arterial wall 74 when the barbed filter device 120 is pressed into the artery 26. Thus, the barbed filter device 120 is secured by a mechanism other than (or in addition to) interference between the body 46 and the arterial wall 74, and can be positioned precisely in the ostium 24 before being implanted using techniques described earlier to provide expansion of the porous wall 48 of the body 46.

Referring to FIGS. 6 and 7, a bulbous filter device 140 is depicted in an embodiment of the disclosure. The bulbous filter device 140 includes many of the same components and aspects as the above disclosed filter devices 20 and 100, which are indicated with same-numbered numerical references in FIGS. 6 and 7 and/or in the following discussion thereof. In the depicted embodiment, the body 46 defines a flow inlet port 141 at the proximal end 56, best seen in FIG. 7. The bulbous filter device 140 includes a bulbous filter cap 142 that extends from the flow inlet port 141 of the proximal end 56 having a convex outer surface 144 that covers the flow inlet port 141 of the body 46. A hub 146 is positioned on a proximal face 148 of the bulbous filter cap 142. The bulbous filter cap 142 further defines an outer lateral dimension 152 (e.g., diameter having a radius) normal to the body axis 66. Herein, a characteristic of a "bulbous" filter element is that the lateral dimension 152 is greater than a maximum radial dimension 154 of the body 46. The bulbous filter device 140 combines therefore advantages of the barbed filter device 120 with the filter devices 20 and 100 by extending into the lumen of aortic arch 32.

In one embodiment, the bulbous filter cap 142 is formed from a flared portion 156 that extends radially outward from the body axis to define an outer perimeter 158. Without the hub 146, the bulbous filter cap 142 defines an open configuration 160, as can be seen in FIG. 7, enabling unfiltered flow through the flow inlet and flow outlet ports 141 and 64 of the body 46. In one embodiment, the flared portion 156 is made of an elastic material or a material having shape memory that is formed or set in the open configuration, (for example by a thermosetting process) such that, absent the hub 146, the bulbous filter cap 142 will open up and be substantially restored to the flared configuration 160 of FIG. 7.

Functionally, the bulbous filter cap 142 also provides increased flow-through area relative to the filter devices 20, 100 and 120, further enhancing the self-cleaning capability of the bulbous filter device 140. The hub 146 can be utilized to percutaneously grab and maneuver the bulbous filter device 140, for example with a purpose built snare 162. Also, the hub 146 can be used for removal of the bulbous filter device 140 from the artery 26. Such removal could be done at operator discretion several days or weeks after implantation in case of short term need for embolic protection. The operator in this case can catch the hub 146 with the purpose built snare 162 and remove the bulbous filter device 140 from the artery by traction. It is also contemplated to implement a hub or similar structure in any of the filter devices (e.g., 20, 100, 120), whether bulbous or not, to facilitate removal.

In cases where the bulbous filter device 140 is left for a long period of time in the ostium 24 of the artery 26 and is affixed thereto by ingrown tissue, the removal of the entire device 140 can be impossible using minimally invasive surgical techniques. For such long term or permanent installations, and as a precautionary measure, the hub 146 can be removed in certain embodiments to open up the bulbous filter cap 142 into the open configuration 160 should the bulbous filter cap 142 somehow become obstructed. Restoration to the original open configuration 160 is provided by the elastic forces or the shape memory material.

Referring to FIGS. 8A through 8F, assembly of bulbous filter device 140 is depicted in embodiments of the disclosure. In assembly, and prior to implantation, the outer perimeter 158 of the flared portion 156 (FIG. 8A) is gathered together at a bunched neck 164 (FIG. 8B) that can be tied together by the hub 146 to form the bulbous filter cap 142. Various ways to join the outer perimeter 158 at the hub 146 include: screwing the hub 146 onto the bunched neck 164 (FIG. 8C); crimping the hub 146 onto the bunched neck 164 (FIG. 8D); fusing the bunched neck together (a fused portion 166 forming the hub 146) (FIG. 8E); stapling the bunched neck 146 together (a staple 168 serving as the hub 146) (FIG. 8F). For these embodiments, removal of the hub 146 to restore unfiltered flow can be accomplished, for example, by: unscrewing the hub 146; cutting through the bunched neck proximate the hub 146; cutting through or otherwise removing the staple that serves as the hub 146.

Figure 9:
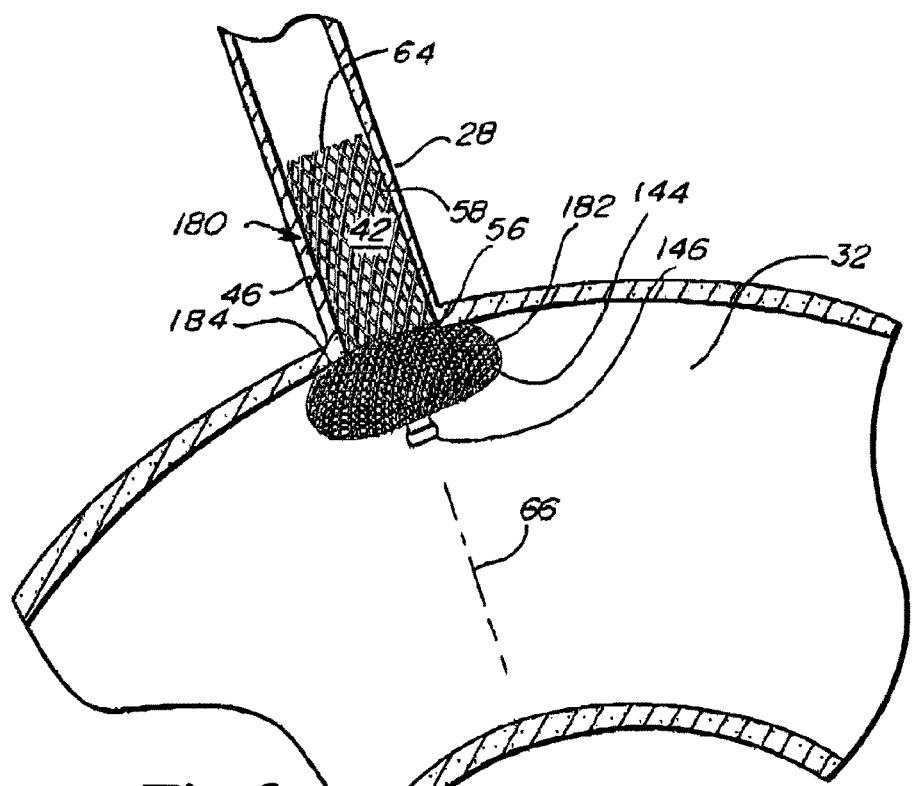
FIG. 9 is a perspective view of a detachable bulbous filter cap in an embodiment of the disclosure.

Referring to FIG. 9, a bulbous filter device 180 having a detachable bulbous filter cap 182 is depicted in an embodiment of the disclosure. The bulbous filter device 180 is a variation of the bulbous filter device 140 of FIGS. 6 and 7, and includes many of the same components and aspects, which are indicated with same-numbered numerical references in FIG. 9 and/or in the following discussion thereof. In one embodiment, the detachable bulbous filter cap 182 is pre-formed in the bulbous geometry rather than being gathered in a bunched neck at the hub 146. The detachable bulbous cap 182 can be mounted to a flange 184 that extends radially outward from the proximal end 56 of the body 46. In this embodiment, the hub 146 can be an optional accessory, utilized to grab and maneuver the bulbous filter device with the purpose built snare 162 and to remove the detachable bulbous filter cap 182 from the flange 184. In some embodiments, the junction between the detachable bulbous cap 182 and the flange 184 can be deliberately weakened relative to the remaining structure of the bulbous filter device 180, so that the detachable bulbous cap 182 will separate or tear away from the flange 184 upon exertion of a sufficient pulling force on the hub 146 in the event that the detachable bulbous filter cap 182 becomes occluded.

Figure 10:
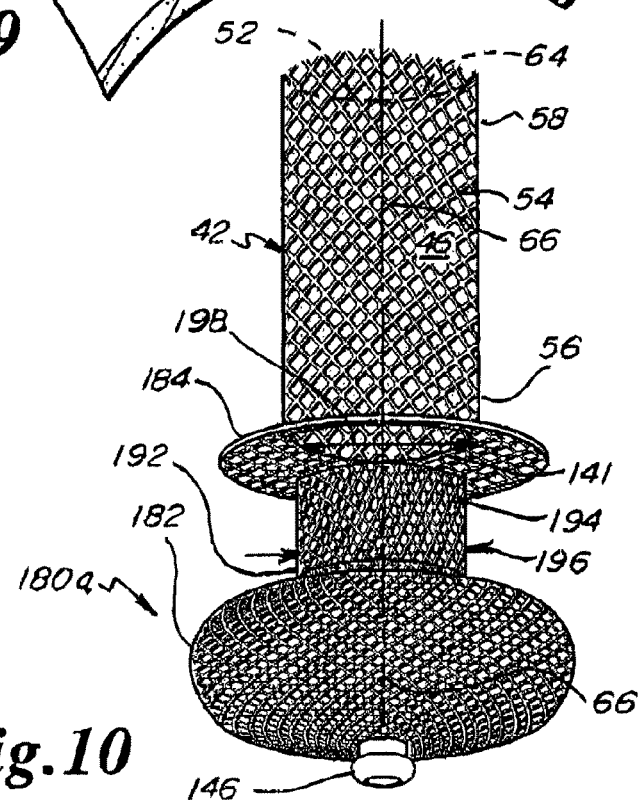
FIG. 10 is a perspective, exploded view of a detachable, replaceable bulbous filter cap having a stem portion in an embodiment of the disclosure.

Referring to FIG. 10, a detachable bulbous filter device 180a is depicted in an embodiment of the disclosure. The detachable bulbous filter device 180a is a variation of the bulbous filter device 180, and as such includes many of the same aspects and components as the detachable bulbous filter device 180, which are indicated with same-numbered numerical references in FIG. 10 and/or in the following discussion thereof. The detachable bulbous filter device 180a includes a stem portion 192 that extends distal to the bulbous filter cap 182. The stem portion 192 has an outer wall 194 dimensioned to fit within the anchor portion 42 (e.g., to have a smaller outer diameter 196 than an inner diameter 198 of the inlet port 141 of the body 46). The stem portion 192 can also comprise a meshed structure. In some embodiments, the stem portion 192 comprises a self-expanding material.

Functionally, the outer diameter 196 of the stem portion 192 contacts the inner surface 52 of the anchor portion 42. The contact provides sufficient interlocking resistance to hold the bulbous filter cap 182 within the anchor portion 42, while enabling the detachable bulbous filter cap 182 to be removed from the anchor portion 42 for replacement. For embodiments implementing the self-expanding material for the stem portion 192, the interlock between the stem portion 192 and the anchor portion 42 can be further enhanced. It is noted, however, that in operation, blood flow through the assembly (bottom to top in FIG. 10) will tend secure the stem portion 192 within the anchor portion 42; accordingly, the interlock between the stem portion 192 and the anchor portion 42 can be light for easier removal.

While the meshed structure of the stem portion 192, when utilized, may experience some ingrowth of tissue over time, the stem portion 192 is separated from the arterial wall 74 by the body 46 of the anchor portion 42, which can substantially reduce the amount of ingrowth, to the point that the stem portion 192 can be removed from the anchor portion 42 even in a permanent installation.

In replacement, the stem portion 192 of the detachable bulbous filter cap 182 can be readily slid into the body 46 of the anchor portion 42. In some embodiments, the stem portion 192 comprises a self-expanding material so that the stem portion 192, initially undersized, grows into seating contact with the inner surface 52 of the body 46 being inserted in the body 46.

Figure 11:
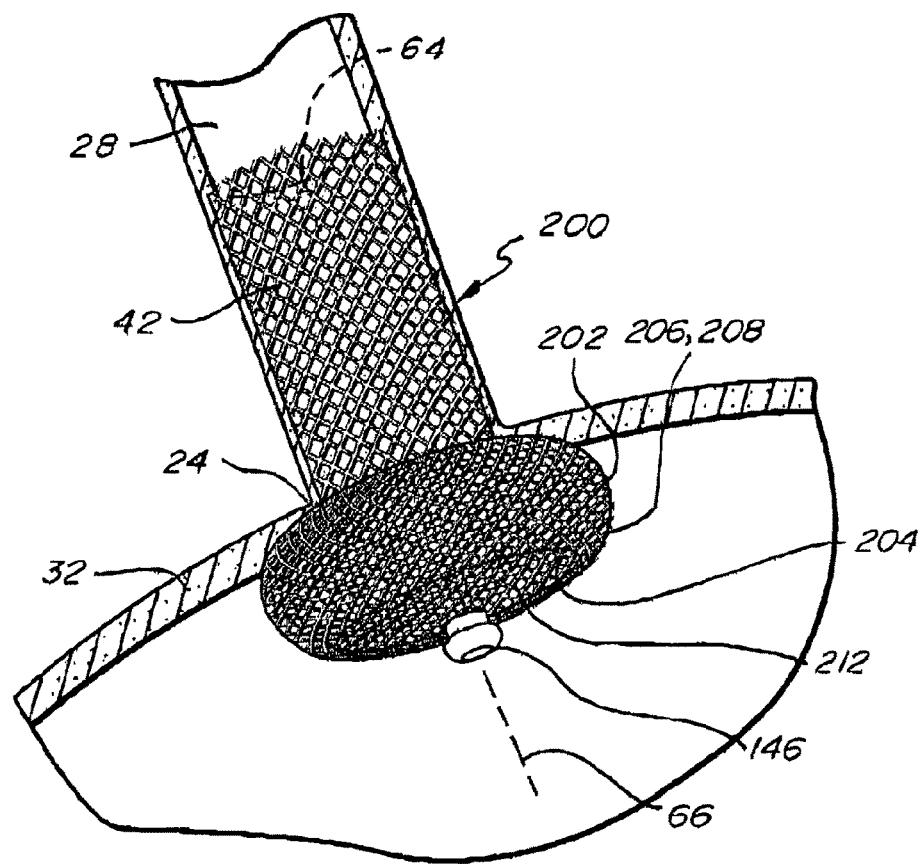
FIG. 11 is a perspective view of a bulbous filter device having a removable hub with a disc portion in an embodiment of the disclosure.

Referring to FIG. 11, another bulbous filter device 200 is depicted in an embodiment of the disclosure. The bulbous filter device 200 is a variation of the bulbous filter device 140 of FIG. 6, and includes many of the same components and aspects, which are indicated with same-numbered numerical references in FIG. 11 and/or in the following discussion thereof. In this embodiment, a bulbous filter cap 202 defines a proximal opening 204 on a proximal face thereof. A peripheral portion 208 of the bulbous filter cap 202 is adjacent the proximal opening 204. The hub 146 includes a disc portion 212 that is disposed over or within the proximal opening 204 of the bulbous filter cap 202, the disc portion 212 being in overlapping contact with and being joined to the peripheral portion 208.

In this embodiment, the bulbous filter cap 202 can comprise an elastic or a shape memory material that assumes a flared shape akin to FIG. 7, such that the bulbous geometry of the bulbous filter cap 202 is maintained by the joinder of the disc portion 212 and the flared portion 156 (FIG. 7). In some embodiments, the junction between the bulbous filter cap 202 and the disc portion 212 of the hub 146 are deliberately weakened relative to the remaining structure of the bulbous filter device 200, so that the disc portion 212 will separate or tear away from the bulbous filter cap 202 upon exertion of a sufficient pulling force on the hub 146 in the event that the bulbous filter cap 202 becomes occluded.

In various embodiments, upon removal of the hub 146 and disc portion 122, the bulbous filter cap 140 assumes an open configuration akin to the open configuration 160 of FIG. 7. Joinder of the disc portion 212 to the bulbous filter cap 202 for the open configuration alternative can be accomplished in several ways, including but not limited to: adhesive disposed between the disc portion 212 and the peripheral portion 208 of the bulbous filter cap 202; fusion or welding.

The tear away aspect of the bulbous filters 182, 202 can be accomplished in several ways, including but not limited to: appropriate amounts and selection of adhesive at the junctions; appropriate levels of fusion or welding, provided, for example, by discrete point tack welding; frangible structure at or adjacent the junctions; and electrolytic erosion. An example of electrolytic erosion is presented, for example, at U.S. Pat. No. 7,862,602 to Licata et al.

Figure 12:
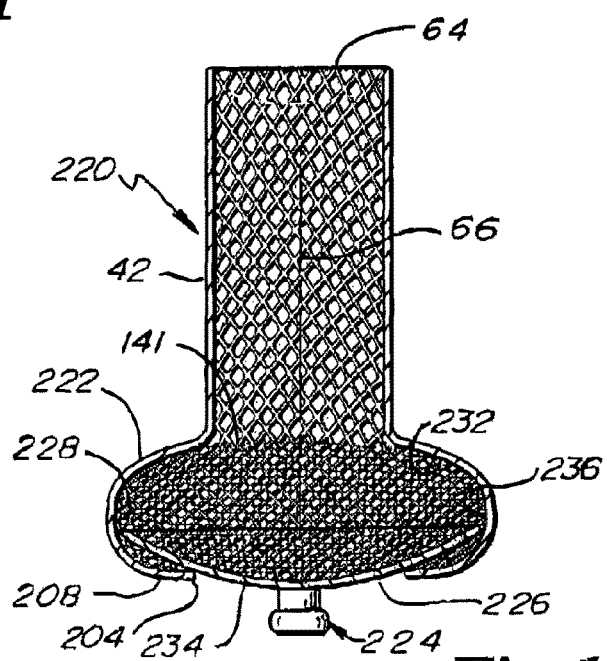
FIG. 12 is a sectional view of a bulbous filter device having a removable, replaceable hub having a disc portion in an embodiment of the disclosure.

Referring to FIG. 12, a sectional view a bulbous filter device 220 having a resilient bulbous filter cap 222 and a replaceable disk 226 with hub 224 is depicted in an embodiment of the disclosure. The bulbous filter device 220 includes many of the same aspects and characteristics as the bulbous filter device 200, as indicated with same-numbered numerical references in FIG. 12 and/or in the following discussion thereof. The bulbous filter device 220 takes on the same general appearance as the bulbous filter device 200 of FIG. 11. However, unlike the disc portion 212 of the bulbous filter device 200, the disk 226 does not function to maintain the bulbous geometry of the bulbous filter cap 222 by joinder to an otherwise flared portion; rather, the bulbous filter cap 222, is pre-formed to be resilient in the bulbous geometry, so as to maintain the bulbous geometry sans the disc portion 226.

The disc portion 226 includes an outer perimeter 228 that seats on an inner surface 232 of the bulbous filter cap 222. In one embodiment, the disc portion 226 defines a convex profile 234 that is bowed towards the proximal opening 204. The diameter of the disc portion 226 can be dimensioned to provide a close fit between the outer perimeter 228 and the inner surface 232, at or near a lateral extremity 236 of the inner surface 232 of the bulbous filter cap 222.

In operation, all blood that flows through proximal opening 204 or the peripheral portion 208 of the bulbous filter cap 222 then flows through the filtering structure of the disc portion 226 by virtue of the close fit between the outer perimeter 228 and the inner surface 232 at or near the lateral extremity 236. The dynamic response of the disc portion 226 to the blood flow therethrough can also slightly flatten the convex profile 234, causing the outer perimeter 228 to extend slightly radially outward, thereby further enhancing the seating between the disc portion 226 and the inner surface 232 of the bulbous filter cap 222. In various embodiments, the disc portion 226 comprises a self-expanding material, further augmenting the seating between the disc portion 226 and the inner surface 232 due to the elastic expansion force of the self-expanding material.

Figure 13:
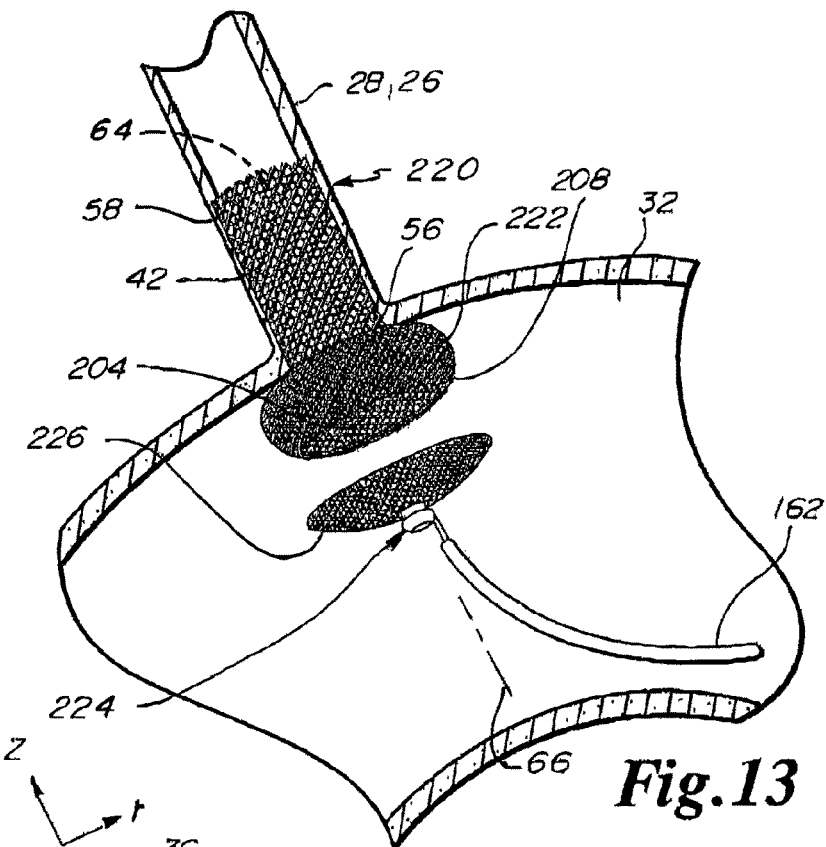
FIG. 13 depicts the bulbous filter device of FIG. 12 in an implanted configuration with the removable, replaceable hub and disc removed.

Referring to FIG. 13, the bulbous filter device 220 is depicted with the replaceable disk 226 removed from the bulbous filter cap 22 with the purpose built snare 162. The resilient property of the bulbous filter cap 224 facilitates replacement of the disc portion 226, should the disc portion 226 become occluded. To remove the disc portion 226, the hub 224 is snared and a pulling force exerted in a direction parallel to the body axis 66, as depicted in FIG. 13. The pulling force causes the disk 226 to contract and/or the proximal opening 204 to expand as the disc portion 226 is pulled through the proximal opening 204. The resiliency of the bulbous filter cap 222 causes the proximal opening 204 to return substantially to the pre-stressed dimension.

In replacement, a new disc portion 226 is folded to a dimension that clears the proximal opening 204 and fed through the proximal opening 204 and left to unfold within the bulbous filter cap 222. The hub 224 can be used for gripping, orienting, and maneuvering the filter disc portion 226.

For the various bulbous filter devices 140, 180, 180a, 200, and 220, the respective bulbous cap 144, 182, 202, and 222 is of larger radial dimension than the body of the anchor portion 42. Accordingly, the respective bulbous filter device can act to register the bulbous filter device at the mouth of the ostium 24 (e.g., as presented for bulbous filter device 140 at FIG. 6). In other embodiments, the body 46 protrudes into the aortic arch 32 (e.g., as depicted for bulbous filter device 180 at FIG. 9), so that the proximal portion 56 of the body 46 acts as a filter, as discussed attendant to FIGS. 2, 3, and 4 above.

Referring to FIGS. 14 through 20, filter devices 250 that include bypass apertures 252 are depicted in implanted configurations 254 in embodiments of the disclosure. The filter devices 250, bypass apertures 252, and implanted configurations 254 are herein referred to collectively or generically by the numerical references 250, 252, and 254 respectively, and individually with a letter suffix (e.g., filter device 250a, bypass aperture 252a, and implanted configuration 254a). The implanted device depictions of FIGS. 14 through 20 showing flow through the aortic arch 32 portray only the outline of the filter devices 250 (i.e., without depicting meshed walls) for illustrative clarity; representative and non-limiting porous wall structures are illustrated in the various isolated device depictions related to FIGS. 14 through 20.

Figure 14:
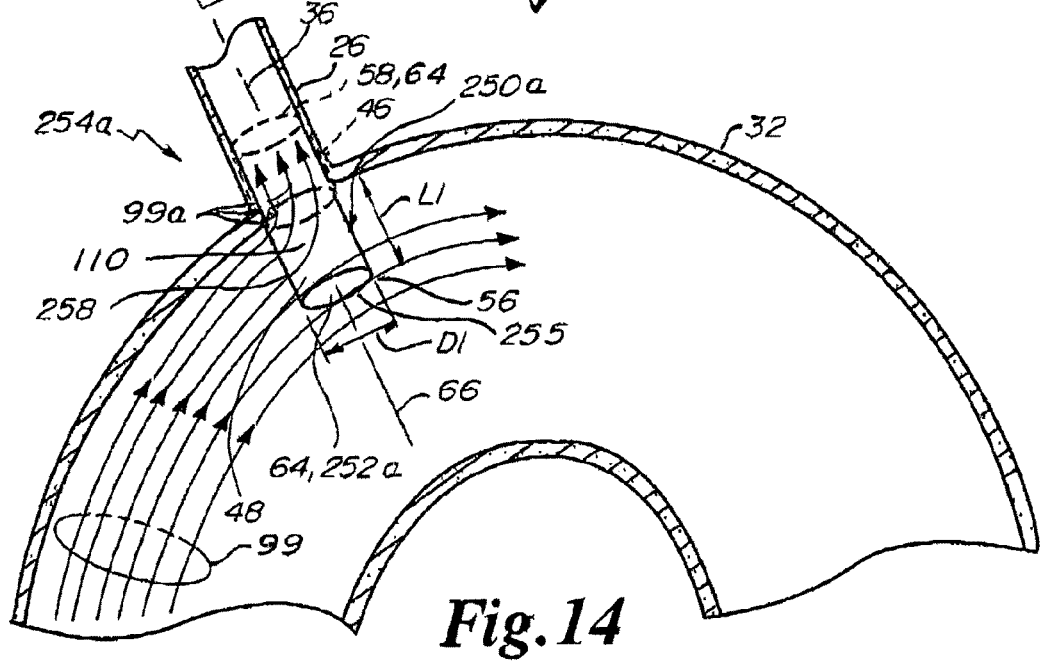
FIG. 14 is a cutaway perspective view of a straight cylinder filter device in an implanted configuration with a bypass aperture at a proximal end in an embodiment of the disclosure.

In one embodiment, as illustrated in FIG. 14, a filter device 250a can include many of the same components and aspects as the filter devices 20, 20a, and 90, which are indicated with same-numbered numerical references in FIG. 14 and/or in the following discussion thereof. A difference between the filter devices 20, 20a, and 90 and the filter device 250a is that filter device 250a does not include a filter cap at the proximal portion 56; rather, the filter portion 110 at the proximal portion 56 of the body 46 defines an opening 255 that is left open to define the bypass aperture 252a. The filter portion 110 extends over the immersion length L1 of the filter device 250a. As disclosed above, the pores of the anchor portion 42 and the filter portion 110 can define first and second porosities 94 and 98, respectively, the second porosity 98 including pores of smaller size and/or defining a lower porosity than the first porosity 94 of anchor portion 42. In one embodiment, the first porosity 94 of anchor portion 42 extends circumferentially around the anchor portion 42, and the second porosity 98 of the filter portion 110 extends circumferentially around the filter portion 110. Alternatively, the porosities of the porous wall 48 can vary tangentially as depicted and discussed attendant to filter device 90 (FIG. 3), with the coarser first porosity 94 being oriented to face in the downstream direction 97 of the aortic arch 32. In one embodiment, the filter device 250a is cylindrical, defining an inner diameter D1, and the immersion length L1 into to the aortic arch 32 is at least as long as the diameter D1.

In implantation and operation, the immersion length L1 for the implanted configuration 254a is of sufficient length so that the portion 99a of the blood flow 99 that enters the artery 26 first passes through the porous wall 48 of the body 46. In the implanted configuration, an upstream portion 258 of the porous wall 48 that faces upstream into the blood flow 99 performs the majority of the filtering. In the event that the upstream portion 258 becomes occluded, the blood flow 99 courses around the occlusions and enters the filter device 250a closer to the lateral sides of the filter device 250a. Because none of the streamlines of the blood flow 99 enter the bypass aperture 252a, none of the blood entering the filter device 250a is unfiltered. This is true even when the filter device 250a becomes partially occluded.

In another embodiment, as illustrated in an implanted configuration 254b in FIG. 15, a filter device 250b can include many of the same components and aspects as the filter device 100 of FIG. 4, which are indicated with same-numbered numerical references in FIG. 15 and/or in the following discussion thereof. As disclosed above, the pores of the anchor portion 42 and the filter portion 110 can define first and second porosities 94 and 98, respectively, the second porosity 98 including pores of smaller size and/or defining a lower porosity than the first porosity 94 of anchor portion 42. In one embodiment, the first porosity 94 of anchor portion 42 extends circumferentially around the anchor portion 42, and the second porosity 98 of the filter portion 110 extends circumferentially around the filter portion 110. A difference between the filter device 100 and the filter device 250b is that filter device 250b includes a bypass aperture 252b formed on the porous wall 48 near the proximal end 56. The bypass aperture 252b is typically oriented to face away from the blood flow 99, i.e., in a downstream direction 97.

Herein, "lateral" bypass apertures are so named because they face at least partially in a direction normal to an axis of the anchor portion. In some embodiments (e.g., FIG. 17, discussed infra), the lateral aperture is formed by curving the body 46 so that an open end of the body is so-oriented. In some embodiments, the lateral aperture is formed on the side of the body 46 (e.g., FIG. 15, discussed infra).

In an embodiment as illustrated in an implanted configuration 254c in FIG. 16, a filter device 250c can include many of the same components and aspects as the bulbous filter device 140 of FIG. 6, which are indicated with same-numbered numerical references in FIG. 16 and/or in the following discussion thereof. As disclosed above, the pores of the anchor portion 42 and the bulbous filter cap 142 can define first and second porosities 94 and 98, respectively, the second porosity 98 including pores of smaller size and/or defining a lower porosity than the first porosity 94 of anchor portion 42. In one embodiment, the first porosity 94 of anchor portion 42 extends circumferentially around the anchor portion 42, and the second porosity 98 of the filter portion 110 extends circumferentially around the filter portion 110. A difference between the bulbous filter device 140 and the filter device 250c is that filter device 250c includes a lateral bypass aperture 252c formed on the bulbous filter cap 142 near the proximal end 56. The lateral bypass aperture 252c is typically oriented to face away from the blood flow 99.

In the embodiment illustrated in implanted configuration 254d in FIG. 17 (depicted in isolation in FIG. 17A), a filter device 250d includes many of the same components and aspects as the filter device 20, which are indicated with same-numbered numerical references in FIG. 17 and/or in the following discussion thereof. In the depicted embodiment, the first porosity 94 of anchor portion 42 extends circumferentially around the anchor portion 42, and the second porosity 98 of the filter portion 110 extends circumferentially around the filter portion 110 (FIG. 17A). The body 46 of the filter device 250d defines a curved cylinder 259 about a curved body axis 66. The filter portion 110 of the curved cylinder 259 of the filter device 250d includes an elbow portion 260 defined near the proximal end 56, the elbow portion 260 defining a lateral bypass aperture 252d. In the depicted embodiment, the bypass aperture 252d intersects the body axis 66 at a substantially right angle. In one embodiment, the curved cylinder 259 includes an extension portion 262 that extends in the radial direction r of the cylindrical coordinate system 91. The bypass aperture 252d is typically oriented to face away from the blood flow 99.

A characteristic of the filter device 250d, and of embodiments generally that define a curved body axis 66, the flow outlet port 64 is normal to a first axis 253, and the lateral bypass aperture 252d is normal to a second axis 257, the axes 253 and 257 being concentric with the curved body axis 66. The first axis 253 is not parallel to the second axis 257; that is, the second axis defines a non-zero angle with respect to the first axis. The depiction of FIG. 17A presents the first and second axes 253 and 257 as being substantially normal to each other. For various embodiments, the filter device 250d defines an angle that is in a range of 60° to 120° inclusive; in some embodiments, in a range of 70° to 110° inclusive; in some embodiments, in a range of 80° to 100° inclusive.

In the embodiment illustrated in implanted configuration 254e in FIG. 18, a filter device 250e can include many of the same components and aspects as the filter device 20, which are indicated with same-numbered numerical references in FIG. 18 and/or in the following discussion thereof. The filter portion 110 of the filter device 250e defines a curved cylinder 259 that, at least in the implanted configuration, includes or expands into an arcuate or elbow-shaped portion 260 defined near the proximal end 56, with the body axis 66 being curved through the elbow-shaped portion 260. As disclosed above, the pores of the anchor portion 42 and the filter portion 110 can define first and second porosities 94 and 98, respectively, the second porosity 98 including pores of smaller size (finer porosity or mesh) and/or defining a lower porosity than the first porosity 94 of anchor portion 42. The elbow-shaped portion 260 defines a bypass aperture 252e. In the depicted embodiment, the bypass aperture 252e lies substantially on a plane 262 that intersects the curved body axis 66 at an acute angle ϕ. The bypass aperture 252e is typically oriented to face away from the blood flow 99. By this arrangement, coverage of both the ostia of a first artery 272 and an adjacent artery 274 is provided.

For the embodiment illustrated in implanted configuration 254f in FIG. 19, filter device 250f includes many of the same components and aspects as the filter device 250d of FIGS. 17 and 17A, which are indicated with same-numbered numerical references in FIG. 19 and/or in the following discussion thereof. Like the filter device 250d, device 250f defines the curved cylinder 259 and the filter portion 110 includes the elbow-shaped portion 260 near the proximal end 56, and a bypass aperture 252f that intersects the body axis 66 at a substantially right angle. The bypass aperture 252f is typically oriented to face away from the blood flow 99.

For the filter device 250f, an elongated extension portion 262f of the filter portion 110 has sufficient lateral dimension L to extend laterally (i.e., in the radial direction r of the r-θ-z coordinate 91) from the elbow-shaped portion 260 over the ostium of an adjacent artery 274 (e.g., the ostium of the left carotid artery and, in some embodiments, also the left subclavian artery of FIG. 1) when the filter device 250f is implanted in a first artery 272 (e.g., the innominate artery of FIG. 1). In one embodiment, the elongated extension portion 262f is dimensioned to have a larger diameter than the anchor portion 42 to augment full coverage of the ostium of the adjacent artery, thereby compensating for directional alignment uncertainty. In some embodiments, the elongated extension portion 262f can be resilient and pre-formed to define an elliptical cross-section (not depicted) with the major axis of the ellipse being oversized to augment full coverage of the ostium of the adjacent artery. In some embodiments, the extension portion 262f can be resilient and define a circular cross-section, but, under the stresses imposed on the elongated extension portion 262f in the implanted configuration 254f, assumes an elliptical cross-section.

Referring to FIGS. 19A and 19B, the filter device 250f is depicted in embodiments of the disclosure. The depicted embodiments of FIGS. 19A and 19B are the same, except the FIG. 19B embodiment includes a centering hook 276. In these embodiments, the porosities of the porous wall 48 are configured to vary tangentially, akin to filter device 90 depicted and discussed attendant to FIG. 3. The filter device 250f is configured so that a superior face 282 and a downstream-oriented face 284 of the body 46 defines the (coarser) first porosity 94, the downstream-oriented face 284 being axially adjacent to the superior face 282 along the curved body axis 66. The filter device 250f is further configured so that an inferior face 286 and an upstream-oriented face 288 of the body 46 includes the (finer) second porosity 98, the upstream-oriented face 288 being axially adjacent to the inferior face 286 along the curved body axis 66.

Functionally, having the finer second porosity 98 on the inferior and upstream-oriented faces 286 and 288 provides filtration of the blood flow 99a entering the implanted first artery 272 (e.g., the innominate artery), as well as a blood flow 99b entering the adjacent artery 274 (e.g., the left carotid artery). The coarser first porosity 94 on the superior and downstream-oriented faces 282 and 284 enhances tissue ingrowth into the filter device 250f over time for better anchoring. Also, having the coarser first porosity 94 cover ostium of the adjacent artery 274 partially mitigates the double filtering of the entering blood stream and attendant restriction in blood flow.

By orienting the bypass apertures 252b-252f to face away from the blood flow 99, an outflux 270 of blood through the bypass apertures 252b-252f is maintained under normal operating conditions. That is, blood flow 99 that enters the filter devices 250b-250f (i.e., through the porous wall 48, the bulbous filter cap 142, or the elbow-shaped portion 260) that is not drawn into the artery 26 will pass through the bypass apertures 252b-252f of filter devices 250b-250f. Accordingly, any debris that is deflected by the filter devices 250b-250f will bypass the bypass apertures 252b-252f and not be drawn into the filter devices 250b-250f. The outflux 270 can be maintained (albeit at less intensity) even if the filter device 250b-250f becomes partially occluded. Thus, despite the presence of unfiltered bypass apertures 252, blood flow 99a entering the artery 26, blood flow 99a entering the artery 26 still passes through a filter medium in normal operation, and even when the filter device 250 is in a partially occluded state.

In the unlikely event that the filter device 250b-250f becomes so heavily occluded as to interrupt normal operation, blood can still flow into resident artery. In such a scenario, some of the blood flowing past the heavily occluded filter portion 110 would be drawn into the bypass apertures 252b-252f to enter the artery.

In various embodiments, the bypass apertures 252 are sized to define access ports dimensioned to permit surgical instruments to pass through the filter device 250 for servicing of the artery 26, without need for destroying or otherwise compromising the filter device 250. The bypass apertures 252 can also allow transradial access to thoracic aorta when the filter device is implanted, for example, in the ostium of innominate artery or left subclavian artery. The bypass aperture 252 can also permit blood flow therethrough in the unlikely event that the filter device 250 becomes heavily occluded.

For the embodiment illustrated in implanted configuration 254g in FIG. 20, filter device 250g includes many of the same components and aspects as the filter device 250f of FIGS. 19, 19A, and 19B, which are indicated with same-numbered numerical references in FIG. 20 and/or in the following discussion thereof. Like the filter device 250f, device 250g defines the curved cylinder 259, and the filter portion 110 includes the elbow-shaped portion 260 near the proximal end 56, with an elongated extension portion 262g of the filter portion 110 having sufficient lateral dimension L to extend laterally from the elbow-shaped portion 260 over the ostium of the adjacent artery 274 when the filter device 250g is implanted in a first artery 272.

The filter device 250g defines a slot 271 that extends along the elongated extension portion 262g and faces in the superior direction 30. As such, in the depicted embodiment, a downstream or lateral end 273 of the elongated extension portion 262g does not define a tube and aperture, but rather a channel 275 and channel opening 277. The channel opening 277 is typically oriented to face away from the blood flow 99. Depending on the length of the slot 271, the filter device 250g can also incorporate the optional centering hook 276 of the filtering device 250f.

In the implanted configuration 254g, the channel 275 passes over the ostium of the adjacent artery 274. In one embodiment, the channel 275 contacts the wall of the aortic arch 32, and the slot 271 and channel 275 provide an opening on the elongated extension portion 262g that aligns over the ostium of the adjacent artery 274. Also, akin to the elongated extension portion 262f, the elongated extension portion 262g can be resilient and pre-formed to outline a generally elliptical cross-section, or can assume the elliptical cross-section under the stresses of the implanted configuration 254g.

Functionally, for filter devices 250f and 250g, the dimensioning the elongated extension portion 262, 262g to cover the ostium of the adjacent artery 274 provides an additional degree of filtration and protection of the adjacent artery 274. In some embodiments, the lateral dimension L is long enough to cover more than one adjacent artery 274. For example, the lateral dimension L can be sized so that the filter device 250f, 250g, when mounted in the innominate artery, extends to cover both the left carotid artery and the left subclavian artery of FIG. 1. Blood can still flow through the porous walls of the elongated extension portion 262 to enter the adjacent artery 274, while emboli that could otherwise swirl into the adjacent artery 274 would be generally blocked by the porous walls of the elongated extension portion 262, 262g. Furthermore, the slot 271 and channel 275 of the filter device 250g entirely eliminates any double filtering of the blood flow 99b entering the adjacent artery 274. "Double filtering" occurs when a blood flow must pass through the filter portion 110 twice, which imposes an unnecessary and generally undesirable restriction to blood flow. The slot 271 eliminates the porous wall 48 that would otherwise be immediately adjacent the ostium of the adjacent artery 274, so there is no double filtering of the blood flow 99b.

As discussed attendant to FIGS. 20A and 20B below, the slot 271 and channel 275 of filter device 250g further enable the elongated extension portion 262g to spread or flare out at the channel opening 277, effectively enlarging the width of the elongated extension portion 262g to augment full coverage of the ostium of the adjacent artery 274, thereby compensating for directional alignment uncertainty.

Referring to FIGS. 20A and 20B, filter devices 250h and 250i are depicted, respectively, in embodiments of the disclosure. The filter devices 250h, 250i are embodiments of the filter device 250g, and as such include all of the components and aspects as the filter device 250g, which are indicated with same-numbered numerical references in FIGS. 20A and 20B and/or in the following discussion thereof. Also, the filter devices 250h, 250i can include some components and attributes identified for the filter device 250f of FIGS. 19, 19A, and 19B, which are also identified with same-numbered numerical references in FIGS. 20A and 20B and/or in the following discussion thereof.

For filter device 250h, the slot 271 extends over a portion of the elongated extension portion 262g. For the filter device 250i, the slot 271 extends over the entire length of the elongated extension portion 262g, through the elbow-shaped portion 260, and into the anchor portion 42 of the body 46. Generally, for a given stiffness of the porous wall 48, the longer the slot 271, the wider the elongated extension portion 262g can be spread or fanned out at the channel opening 277, such that the filter portion 110 defines a fanned filter portion 110g. The fanned filter portion 110g is depicted in dashed lines in FIGS. 20A and 20B. In relative terms, the shorter slot of FIG. 20A provides a channel opening 277 having less fanning (narrower spread) with a larger opening dimension in the superior direction 30; the longer slot of FIG. 20B provides a channel opening with greater fanning (wider spread) with a smaller opening dimension in the superior direction 30.

Accordingly, for a given stiffness of the porous wall 48, the channel opening 277 can be tailored to a desired depth in the implanted configuration 254g by dimensioning of the slot 271. In one embodiment, the fanning of the filter portion 110 can eliminate or nearly eliminate any definition of an open channel 277, such as depicted in FIG. 20B. In such an embodiment, the fanned filter portion 110g is akin to a flap that effectively lays over the ostium of the adjacent artery 274. For these embodiments, the porous wall 48 can be configured with sufficient flexibility to enable the fanned filter portion 110g to be lifted away for access to both the adjacent artery 274 and the first artery 272.

In various embodiments, the fanned filter portion 110g defines a maximum width dimension that is in a range of 6 mm to 20 mm inclusive; in some embodiments, a range of 6 mm to 15 mm inclusive; in some embodiments, a range of 7 mm to 12 mm inclusive; in some embodiments, a range of 7 mm to 10 mm inclusive.

As with the filter device 250f, discussed attendant to FIG. 19A, the porosities of the porous wall 48 of the filter devices 250h and 250i can be configured to vary tangentially. Alternatively, the porosities of the porous wall 48 can be configured to vary axially along the curved body axis 66, such as with filtering device 250d of FIG. 17A with the first porosity 94 of anchor portion 42 extends circumferentially around the anchor portion 42, and the second porosity 98 of the filter portion 110 extends circumferentially around the filter portion 110.

Referring to FIG. 18A and again to FIG. 18, the filter device 250e is presented with an optional centering hook 276 in an embodiment of the disclosure. The FIG. 18 depiction (as well as the FIGS. 19 and 20 depictions) presents the first artery 272 as an innominate artery, and also presents the adjacent artery 274 as the left carotid artery extending from the aortic arch 32. The filter device 250e can optionally include the centering hook 276 extending laterally outward (i.e., in a direction away from the curved body axis 66) from the outer surface 54 of the porous wall 48 of the filter device 250e (FIG. 18A).

The centering hook 276 can be dimensioned to bridge the ostia of the first artery 272 and the adjacent artery 274, and to extend into the first artery 272 and the adjacent artery 274, as depicted in FIG. 18. In various embodiments, the centering hook 276 is fabricated from a resilient material so that it is held in place in part by restorative elastic forces incurred during implantation. That is, the centering hook 276 can be dimensioned to define a span 279 that is undersized (FIG. 18A), so that inserting the centering hook 276 in place between the adjacent ostia of the arteries 272 and 274 causes the span 279 to expand after insertion. The span 279 is defined as the distance between a free end 281 and a shank portion 283 of the centering hook 276 in a direction perpendicular to the portion of the body axis 66 that passes through the anchor portion 42 of the filter device 250e. The expansion of the span 279 generates a restorative force that holds or pinches the filter device 250e between the centering hook 276 and the ostium. Optionally, or in addition, the centering hook 276 can be attached to the porous wall 48 by various means available to the artisan, including fusion to the porous wall 48, or by integral formation with the wall 48. In one embodiment, the centering hook 276 can be integrally formed as an extension of one of the cross-members of a meshed structure (e.g., one of the cross-members 82 of meshed structure 86 of FIG. 1D).

The centering hook 276 can also include a spherical or otherwise radiused barb 278. The radiused barb 276 presents dulled (i.e., not sharp) features, as opposed to traditional barbs that are designed to tenaciously set into a target. In comparison to traditional barbs, the radiused barb 278 is less prone to tearing the tissue both during the approach and at target. The radiused barb 278 is also less prone to tearing the filter device 250d during approach and implantation.

Functionally, the centering hook 276 can help maintain the angular orientation (θ orientation of the cylindrical coordinate system 91) of the filter device 250e, which further aids in aligning and maintaining alignment of the bypass aperture 252e in an orientation that faces away from the blood flow 99. The radiused barb 278 can also promote the permanency of the installation, as tissue grows over the radiused barb 278 over time; because the radiused barb is not sharp, such tissue growth can occur without the radiused barb 278 cutting through the growth tissue.

In some embodiments, the centering hook 276 further induces the curvature of the elbow-shaped portion 260 when the filter device 250e is in the implanted configuration 254e. That is, prior to implantation, the filter device 250e may assume a straight configuration, or at least a straighter (less arcuate or less pronounced elbow shape) configuration than in the implanted configuration 254e. The centering hook 276 can be joined to the filter device 250e such that, when hooked to the ostium of the adjacent artery 274, the elbow-shaped portion 260 becomes fully defined. In this manner, the filter device 250d can provide a lower profile during the approach. Alternatively, or in addition, the elbow portion 260 can be permanently formed by, for example, a thermosetting process or by use of a shape-memory materials.

Referring to FIG. 21, a detached centering hook 280 is depicted in an embodiment of the disclosure. The detached centering hook 280 is not connected to the filter device 250e; instead the centering hook 280 is installed separately as a clip. In one embodiment, the centering hook 280 includes the radiused barbs 278 on both the free end 281 and an opposed free end 285. In this embodiment, the span 279 is taken as the distance between the free end 281 and the opposed free end 285. The FIG. 21 depiction also represents both the span 279 and an expanded span 279a in phantom that generates the restorative force that holds or pinches the wall 48 of the filter device 250e between the centering hook 280 and the ostium. In various embodiments, the detached centering hook 280 can be utilized as a retrofit to previously implanted filter devices 250. The detached centering hook 280 provides the same retention and alignment functionality as the centering hook 276, discussed above.

While the centering hooks 276, 280 are described in association with the filter devices 250e, it is understood that centering hooks 276, 280 can be implemented with a variety of the filter devices 250 of the present disclosure. For example, the centering hook 276 (or optionally detached centering hook 280) can be implemented with the filter device 250f to aid in aligning and maintaining alignment of the elongated extension portions 262f, 262g to cover the ostium of the adjacent artery 274. The centering hook 276, 280 further aids in maintaining the bypass aperture 252f or channel opening 277 oriented in the downstream direction 97.

Referring to FIGS. 22, 22A, and 22B, a dual anchor filter device 300a is depicted in an embodiment of the disclosure. A variety of dual anchor filter devices 300 are disclosed herein, referred to collectively or generically by the numerical reference 300 and individually with a letter suffix (e.g., filter device 300a). The dual anchor filter device 300a includes a first anchor portion 302 and a second anchor portion 304 disposed on opposing ends of a filter portion 306. The first anchor portion 302 defines a first outer diameter 308 and includes many of the same components and aspects as, for example, the filter devices 20, which are indicated with same-numbered numerical references in FIGS. 22, 22A, and 22B and/or in the following discussion thereof. The second anchor portion 304 is of similar construction to the first anchor portion 302, defining a second outer diameter 312, a second flow outlet port 314, and including a porous wall 316 that defines a porosity 318. In one embodiment, the porosity 318 is substantially the same as the first porosity 94 of the first anchor portion 302.

In some embodiments, the first anchor portion 302 is dimensioned for anchoring to the first artery 272 and the second anchor portion 304 is dimensioned for anchoring to the adjacent artery 274. It is noted that, while the adjacent artery 274 may be generally of a different diameter than the first artery 272, the first and second outer diameters 308 and 312 can be of the same dimension and still function to reliably anchor the respective anchor portions 302 and 304.

Referring to FIG. 23, a dual anchor filter device 300b is depicted in an embodiment of the disclosure. The dual anchor filter device 300b includes many of the same components and aspects as the dual anchor filter device 300a, which are indicated with same-numbered numerical references in FIG. 23 and/or in the following discussion thereof. The dual anchor filter device 300b is characterized as having first and second diameters 308 and 312 that are of different dimension, with the second diameter 312 being less than the first diameter 308.

In the depicted embodiment, a transition 320 between the first and second diameters 308 and 312 is defined on a part of the porous wall 48 having the second porosity 98. This enables the (finer) second porosity to extend partially into the ostium of the resident artery 274 for better assurance of filtering all of the blood that enters the artery 274.

In this embodiment, the first and second diameters 308 and 312 can be configured for a more tailored anchoring. fit of the first artery 272 and the adjacent artery 274, respectively. Ranges of representative diameters for various arteries is discussed above attendant to FIGS. 1A through 1D. Accordingly, for various embodiments of the dual anchor filter devices 300 tailored for anchoring in the innominate and the left carotid arteries may define a ratio of the first diameter 308 to the second diameter 312 in one of the following non-limiting ranges: 1 to 3 inclusive; 1.4 to 2 inclusive; 1.6 to 1.8 inclusive. A dual anchor filter device for anchoring in the left carotid and left subclavian arteries may define a ratio of the first diameter 308 to the second diameter 312 in one of the following non-limiting ranges: 0.3 to 1 inclusive; 0.5 to 1; 0.9 to 0.7 inclusive. Note that the former range clusters have ratios greater than or equal to unity while the latter range clusters have ratios less than or equal to unity, reflecting the diameters of upstream and downstream arteries for the two configurations.

Referring to FIGS. 24 and 24A, a dual anchor filter device 300c is depicted in an embodiment of the disclosure. The dual anchor filter device 300c includes the same components and aspects as the dual anchor filter device 300a, which are indicated with same-numbered numerical references in FIGS. 24 and 24A and/or in the following discussion thereof. In addition, the dual anchor filter device 300c includes a lateral bypass aperture 322 formed in the filter portion 306. In one embodiment, the lateral bypass aperture 322 is disposed proximate the second anchor portion 304 and oriented to face in the downstream direction 97 within the aortic arch 32.

Figure 25A:
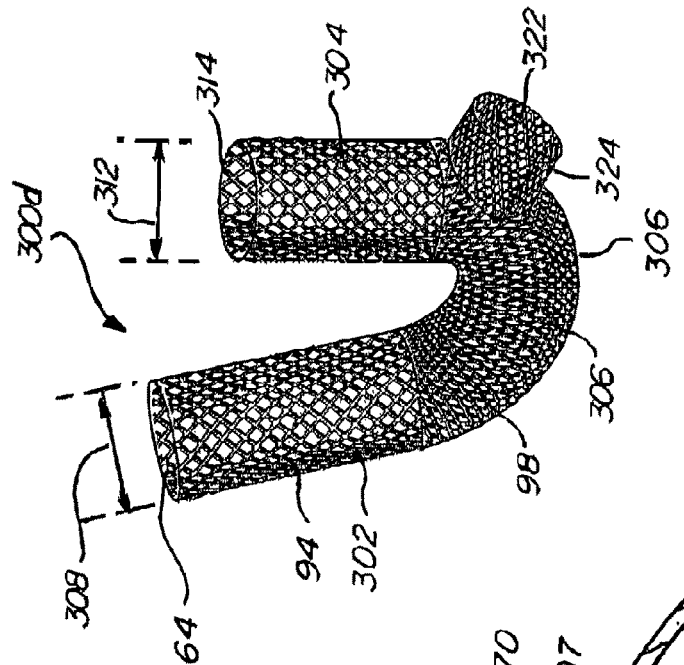
FIG. 25A is a perspective view of the dual anchor filter device of FIG. 25 in the implanted configuration in isolation.
Figure 25:
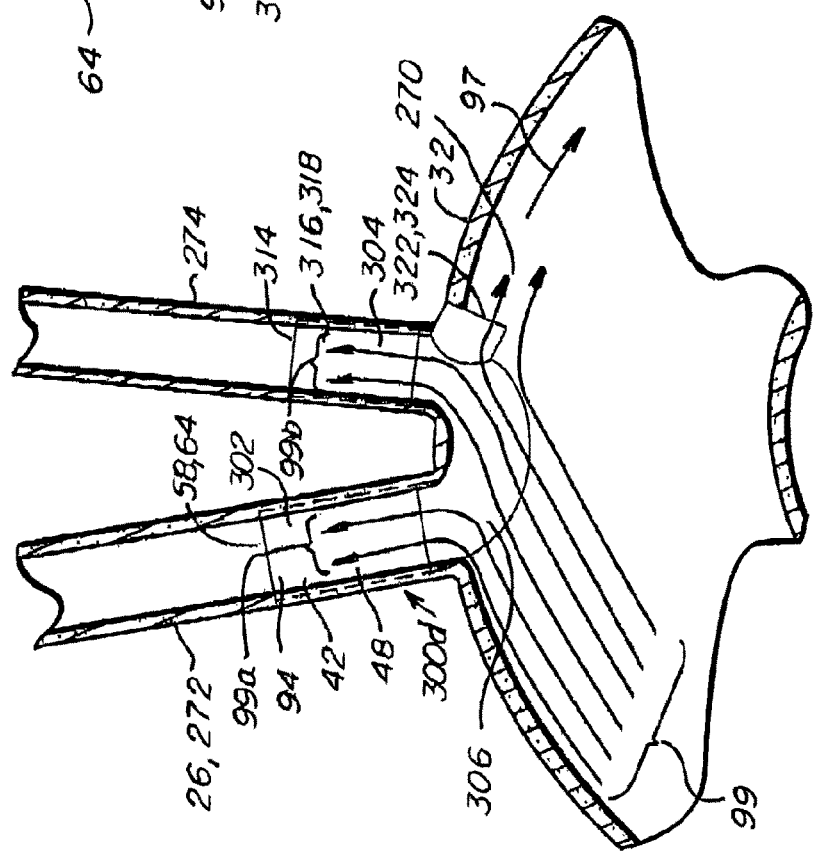
FIG. 25 is a sectional view of a dual anchor filter device with a shrouded bypass aperture in an implanted configuration in an embodiment of the disclosure.

Referring to FIGS. 25 and 25A, a dual anchor filter device 300d is depicted in an embodiment of the disclosure. The dual anchor filter device 300d includes the same components and aspects as the dual anchor filter device 300c, which are indicated with same-numbered numerical references FIGS. 25 and 25A and/or in the following discussion thereof. In addition, the filter portion 302 of the dual anchor filter device 300d includes a shroud 324 formed on the filter portion 306 and protruding radially outward (i.e., in a direction away from the body axis 66), the shroud 324 surrounding the lateral bypass aperture 322.

Functionally, the dual anchor filter devices 300 provide full filtering of the two arteries 272 and 274 (e.g., the innominate artery and the left carotid artery). The dual anchors also fix the orientation of the filter devices 300. The higher porosities 94, 318 (e.g., larger pore sizes) of the anchoring portions 302, 304 facilitate tissue ingrowth into the anchor portions 302 and 304, while the lower porosity 98 (e.g., small pore sizes) of the filter portion 306 facilitate thorough filtering of the blood entering both arteries. The bypass aperture 322, being oriented to face away from the blood flow, operates akin to the bypass apertures 252 described attendant to FIGS. 16 through 20. The shroud 324 offers an added level of prevention against recirculating emboli entering the filter.

Figure 26:
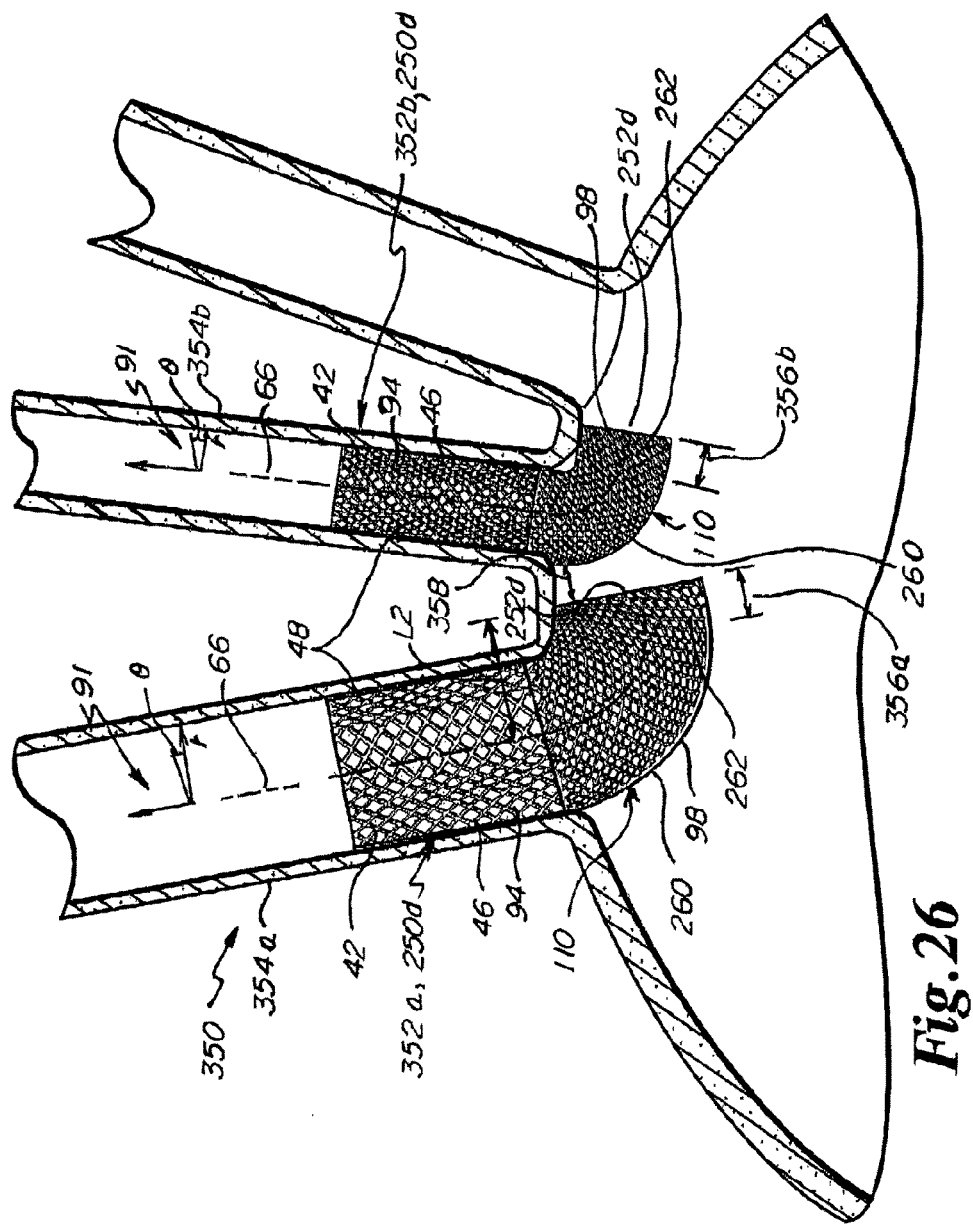
FIG. 26 is a sectional view of a double filter arrangement in an embodiment of the disclosure.
Figure 1:
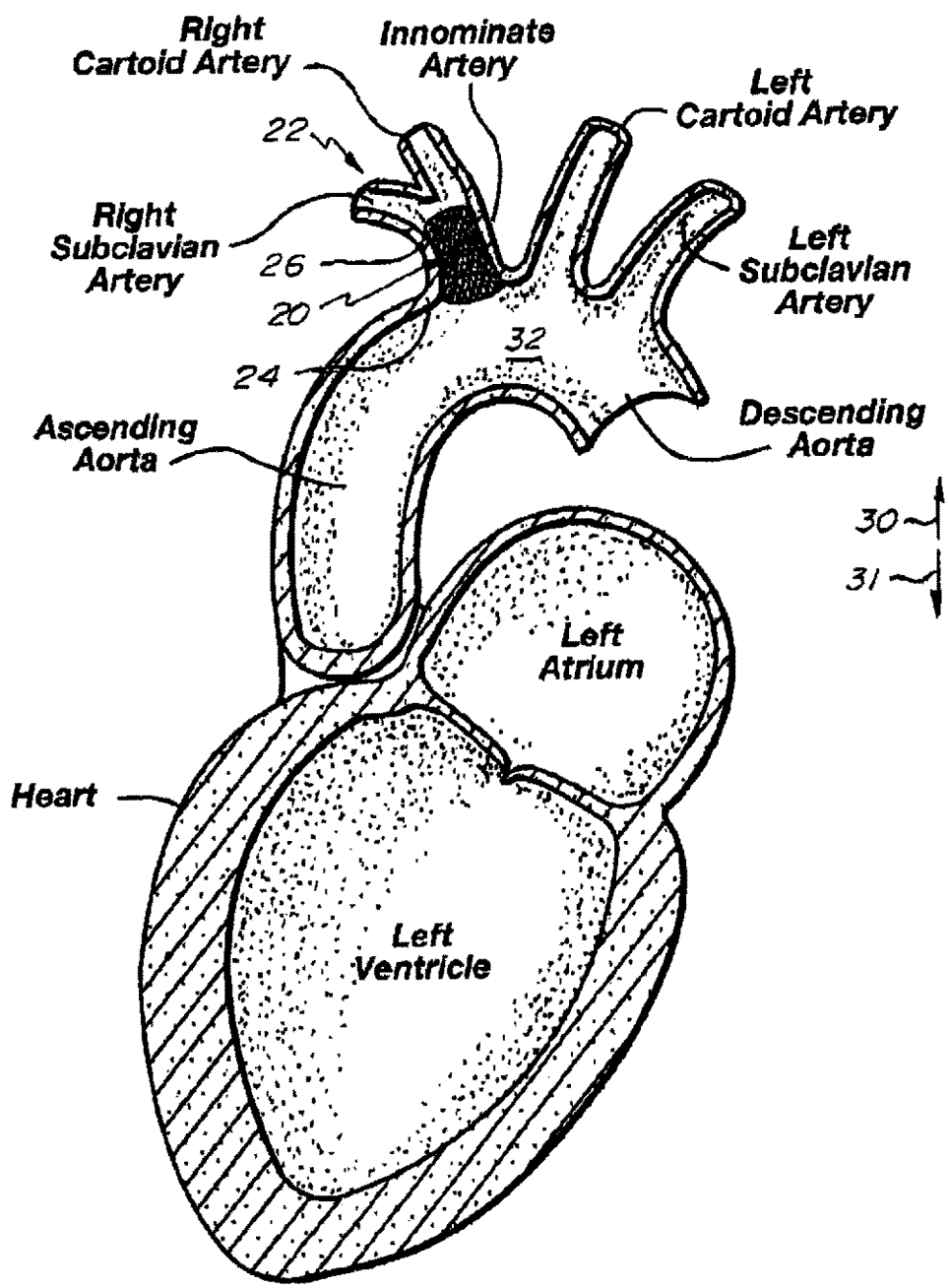
Figure 9:
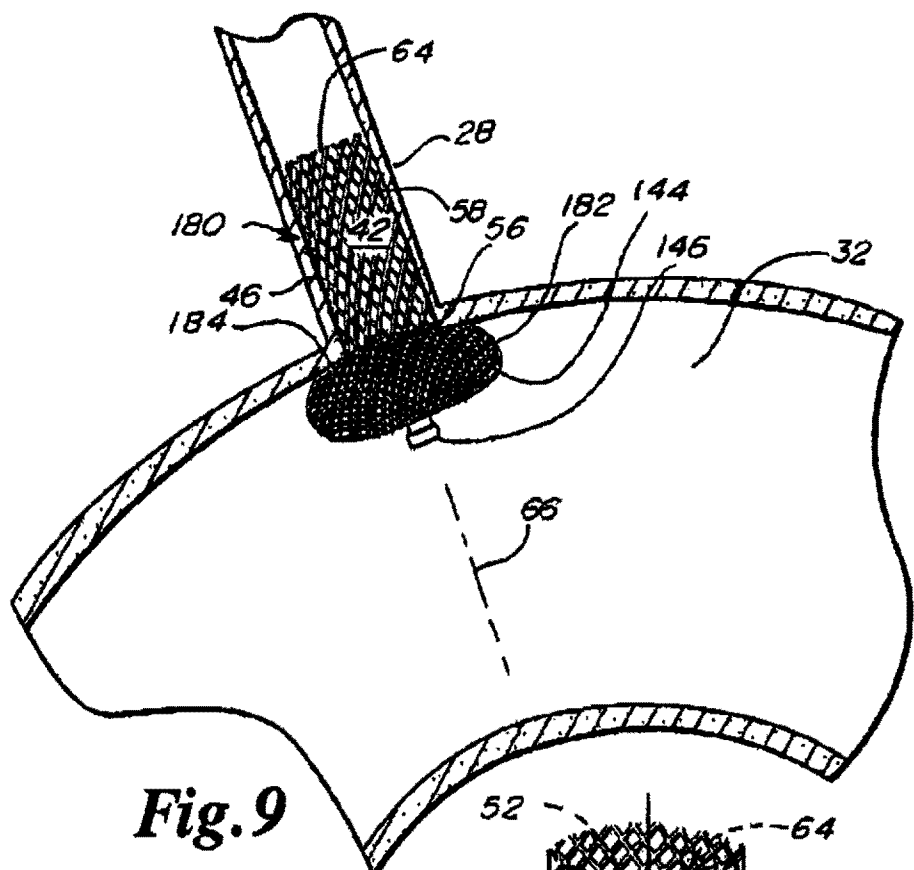
Figure 10:
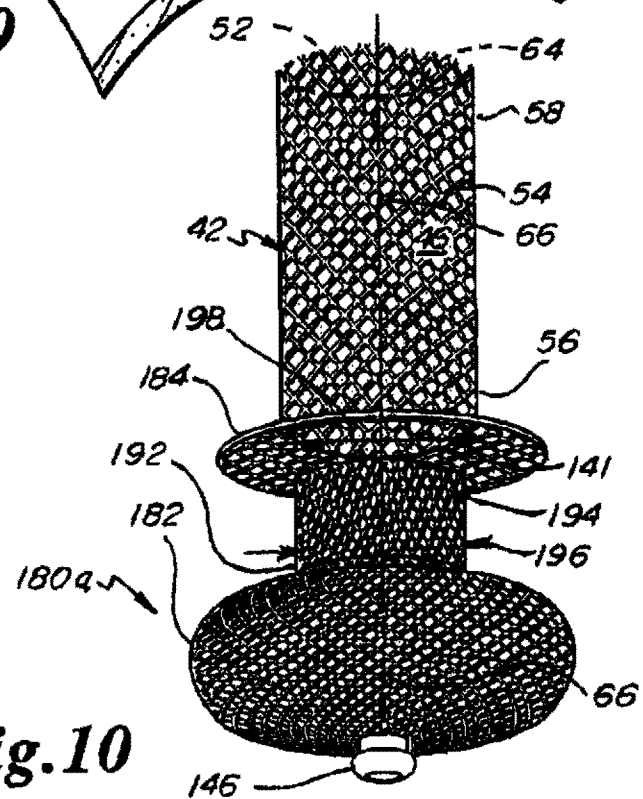
Figure 11:
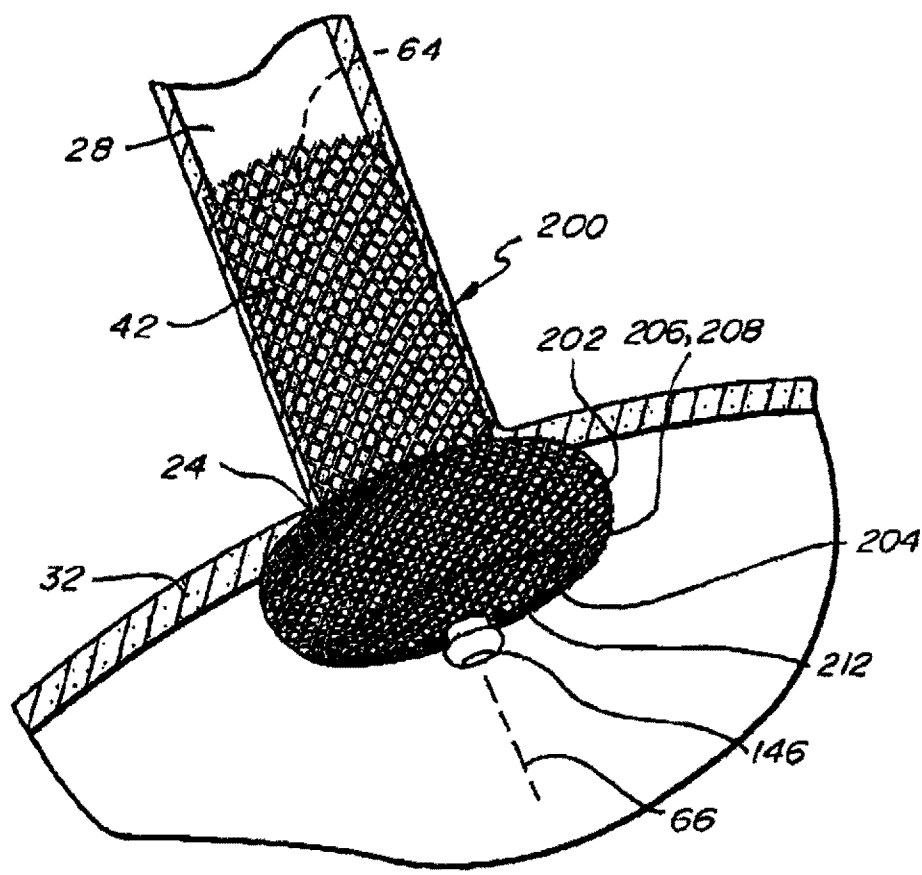
Figure 12:
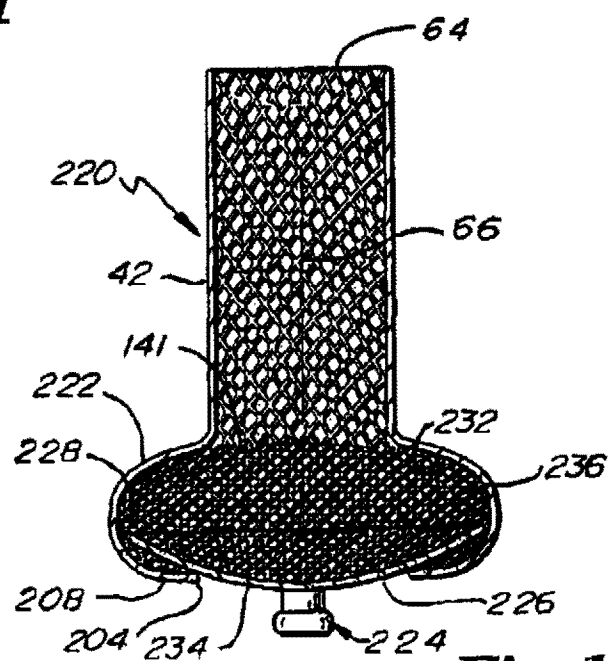
Figure 13:
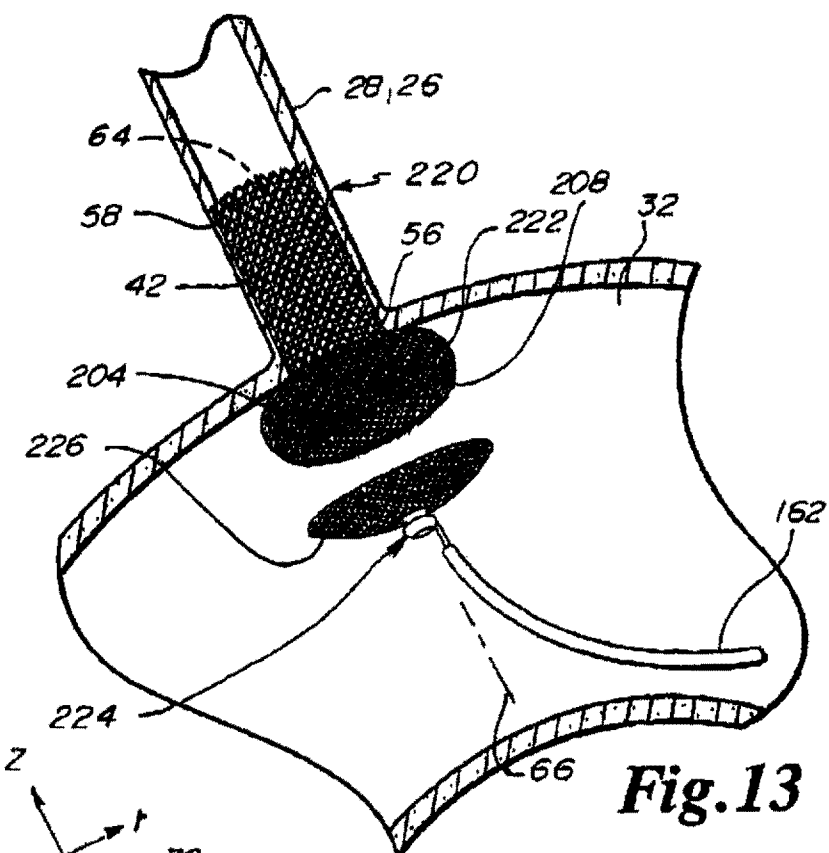
Figure 14:
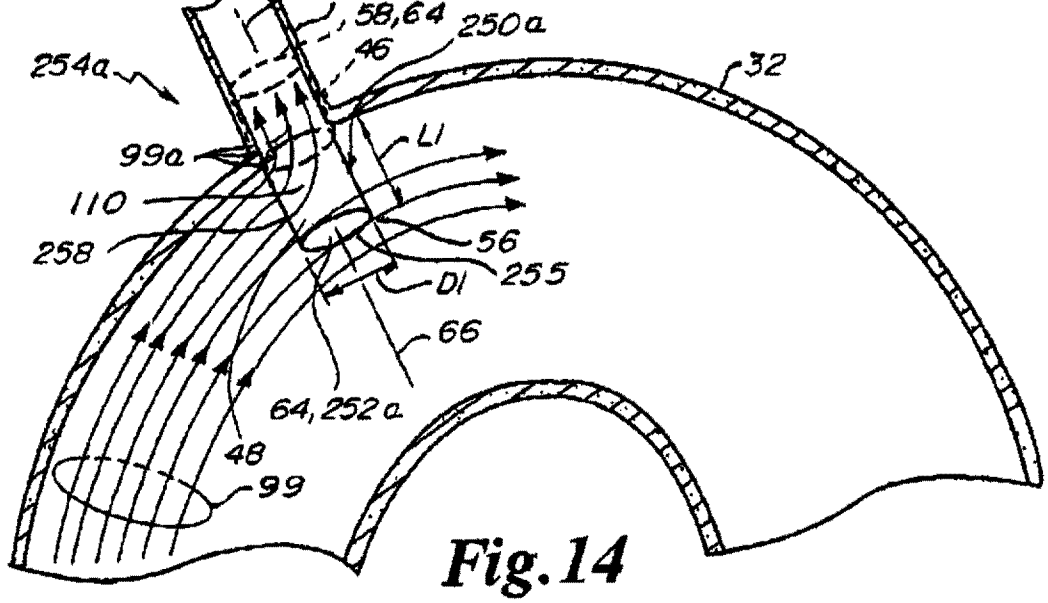
Figure 15:
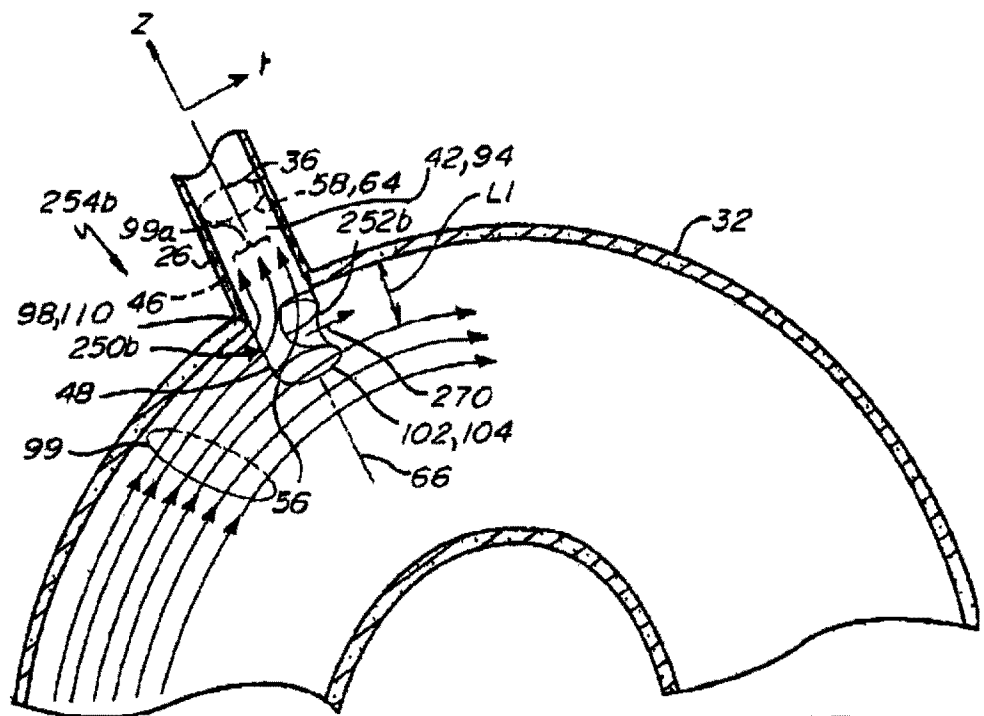
Figure 16:
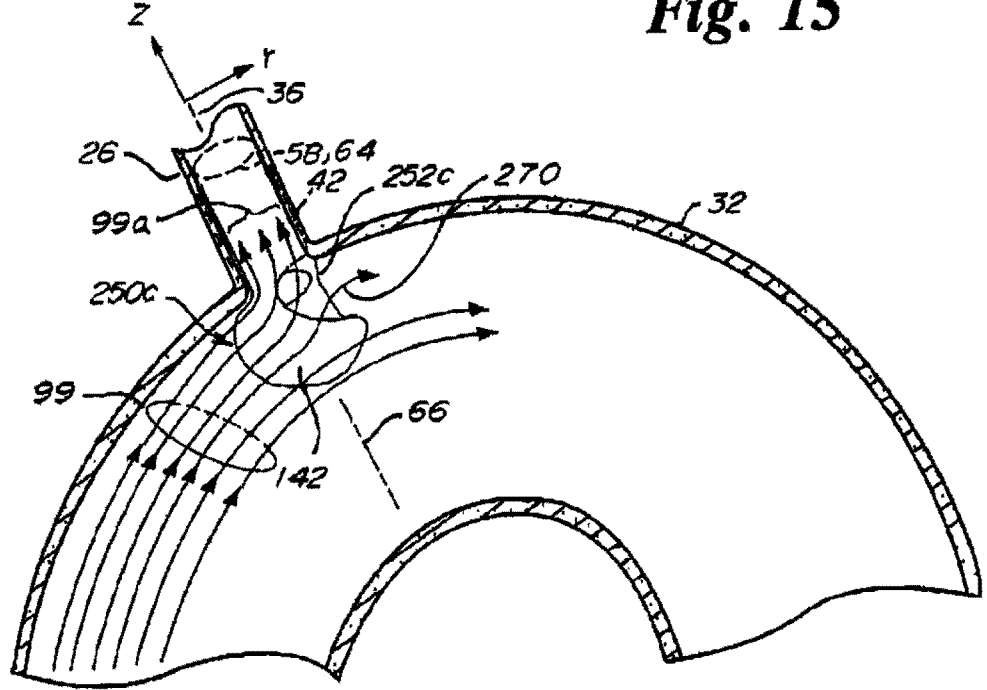
Figure 26:
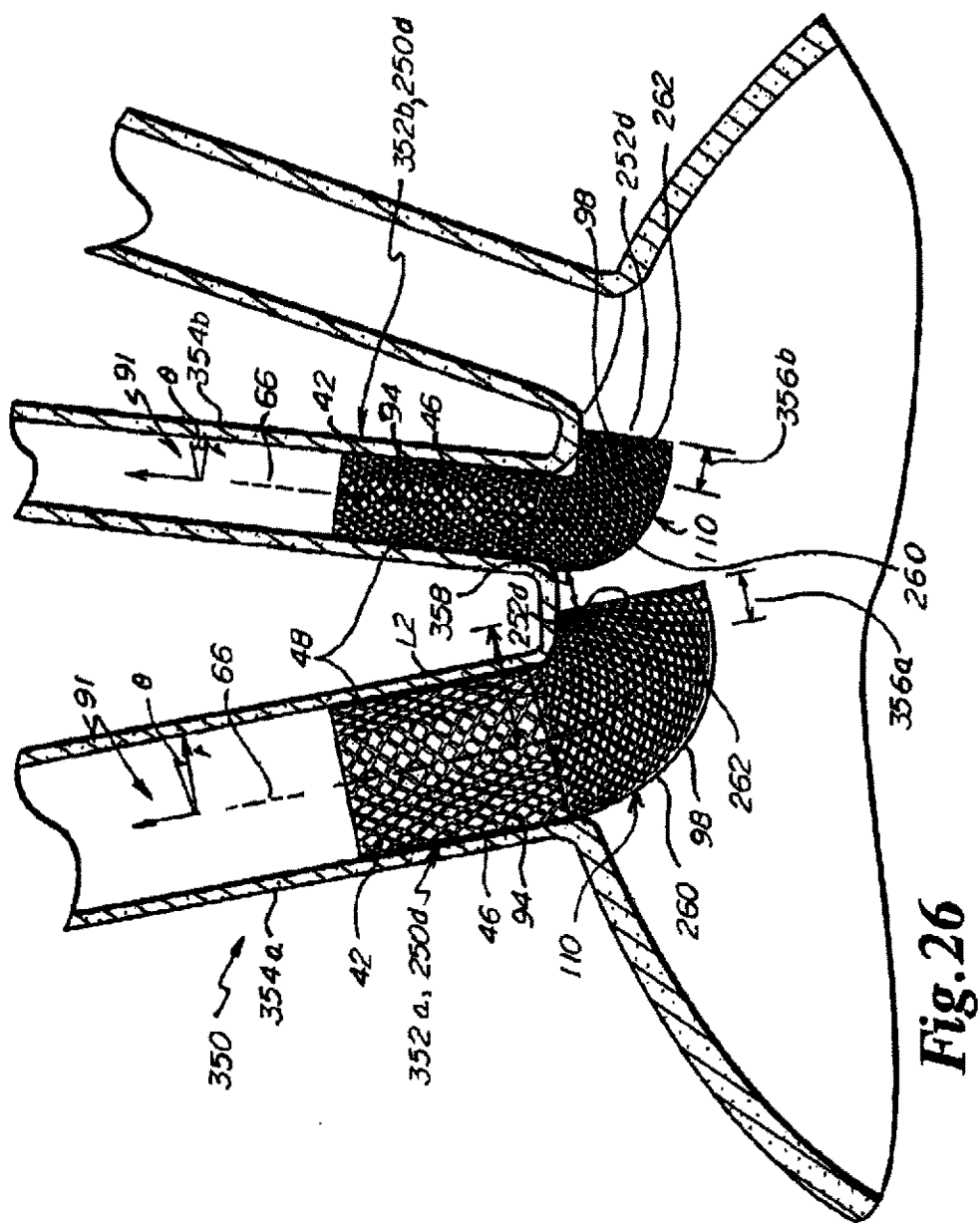

Referring to FIG. 26, a double filter arrangement 350 is depicted in an embodiment of the disclosure. The double filter arrangement 350 includes two filter devices, a first or upstream filter device 352a, and a second or downstream filter device 352b. The filter device 352a is configured for implantation in an upstream artery 354a, and the filter device 352b is configured for implantation in a downstream artery 354b. For the depicted embodiment of the double filter arrangement 350, each of the filter devices 352a and 352b include the same components and attributes as the filter device 250d (FIG. 17), which are indicated with same-numbered numerical references FIG. 26 and/or in the following discussion thereof. Also for the depicted embodiment, the upstream and downstream arteries 354a and 354b are the innominate and left carotid arteries of FIG. 1.

For certain embodiments that utilize the filter device 250d in the upstream artery 354a, a length 356a of the extension portion 262 is dimensioned to provide a minimum radial separation 358 between the bypass aperture 252d of the upstream filter device 352a and the elbow portion 260 of the downstream filter device 352b. Herein, a "radial separation" is a dimension parallel the radial direction r of the cylindrical coordinate system 91 of the upstream filter device 352a.

In various embodiments, non-limiting dimensions for the minimum radial separation 358 are in the range of 2 mm to 5 mm inclusive. In various embodiments, to obtain the desired minimum radial separation 358, the bypass aperture 252d of the upstream filter device 352a is centered at a lateral dimension L2 in a range of 3 mm to 12 mm inclusive from a centerline of the anchor portion; in some embodiments, a range of 5 mm to 10 mm inclusive; in some embodiments, a range of 5 mm to 8 mm inclusive; in some embodiments, a range of 6 mm to 8 mm inclusive.

The configuration of the porous wall 48 of the body 46 of each of the filter devices 352a and 352b may be congruent with various embodiments disclosed herein. For the depicted embodiment of the double filter arrangement 350, each of the filter devices 352a and 352b include the first porosity 94 of anchor portion 42 extending circumferentially around the anchor portion 42, and the second porosity 98 of the filter portion 110 extending circumferentially around the filter portion 110. Alternatively, the anchor and filter portions 42 and 110 of the filter devices 352a and 352b can be configured with porosities 94, 98 that vary tangentially about the curved body axis 66, akin to the filter device 250f discussed attendant to FIG. 19A. Also, for arrangements such as depicted in FIG. 26, where the upstream artery 354a is proximate the downstream artery 354b, the upstream filter device 352a may be configured with a centering hook (not depicted) that bridges the ostia of the upstream and downstream arteries 354a and 354b, akin to the centering hook 276 discussed attendant to FIG. 18 or the detached centering hook 280 discussed attendant to FIG. 21.

As described above attendant to FIGS. 14 through 20, the bypass apertures 252d of the upstream and downstream filter devices 352a and 352b can be sized to define access ports dimensioned to permit surgical instruments to pass through the respective filter device 352a, 352b, for servicing of the respective artery 354a, 354b and without need for destroying or otherwise compromising the filter device 352a, 352b.

Functionally, the downstream-facing orientation of bypass apertures 252d enable transradial access to the arteries 354a and 354b. The minimum radial separation 358 enable surgical instrument access to the bypass aperture 252d of the upstream filter device 352a without substantially disturbing the downstream filter device 352b. That is, surgical instruments (e.g., a guide wire) utilizing a transradial approach can pass over the arcuate surface of the elbow portion 260 of the downstream filter device 352b for entry into the bypass aperture 252d of the upstream filter device 352a with little or mere incidental contact with the downstream filter device 352b.

Further functional aspects of the double filter arrangement 350 are as provided in similar embodiments described above. For example, the double filter arrangement 350 provides affirmative filtering of both arteries 354a and 354b (e.g., the innominate artery and the left carotid artery). The higher porosities 94 (e.g., larger pore sizes) of the anchoring portions 42 facilitate tissue ingrowth into the anchor portions 42, while the lower porosities 98 (e.g., small pore sizes) of the filter portion 110 facilitate thorough filtering of the blood entering the respective arteries 354a and 354b. The bypass apertures 252d, being oriented to face away from the blood flow, operate akin to the bypass apertures 252 described attendant to FIGS. 15 through 20. The bypass apertures 252d can also permit blood flow therethrough in the unlikely event that the respective filter device 352a, 352b becomes heavily occluded.

Alternative embodiments for double filter arrangements 350a through 350d are presented in FIGS. 26A through 26D in embodiments of the disclosure. For double filter arrangement 350a, the upstream filter device 352a does not include an extension portion that extends laterally from the elbow portion 260; rather, the bypass aperture 252d is defined on the elbow portion 260 (FIG. 26A). This effectively increases the minimum radial separation 358 relative to the double filter arrangement 350, thereby increasing accessibility of the upstream filter device 352a.

Figure 15:
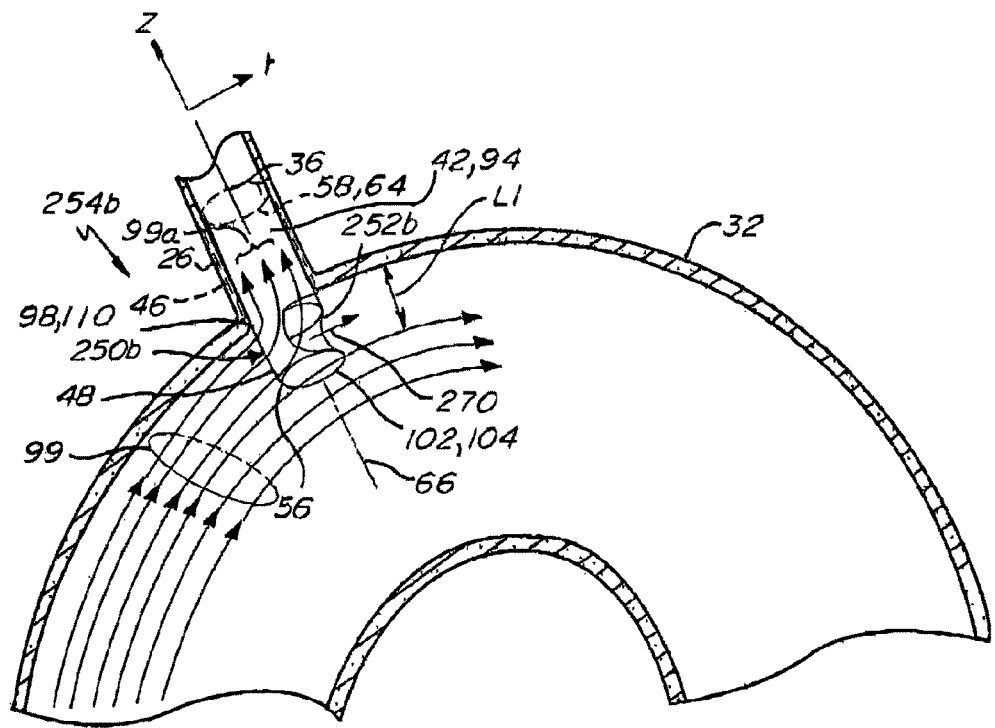
FIG. 15 is a cutaway perspective view of a filter device in an implanted configuration the filter device including a convex filter cap and having a lateral bypass aperture in an embodiment of the disclosure.

For the double filter arrangement 350b, the upstream filter device 352a is the filter device 250b, described attendant to FIG. 15 above. The bypass aperture 252b of filter device 250b is defined in on a lateral side of the body 46 (FIG. 26B), such that the lateral dimension L2 is limited to the radius of the filter portion 110. This also increases the minimum radial separation 358 relative to the double filter arrangement 350.

For the double filter arrangement 350c, the upstream filter device 352a is the filter device 250a, described attendant to FIG. 14 above. The bypass aperture 252a is oriented to face primarily in the inferior direction 31 and at the immersion depth L1 (FIG. 26C). As such, access to the upstream filter device 352a is unaffected by the presence of the downstream filter device 252b.

For the double filter arrangement 350d, the upstream filter device 352a is similar to the filter device 250d of FIGS. 17 and 26, except that the filter portion 110 includes an axial extension 368 that extends an axial length 366 from the ostium of the first artery 354a (FIG. 26D). The axial extension 368 extends the bypass aperture 252d in the inferior direction 31 relative to the bypass aperture 252d of the downstream filter device 352b. By this arrangement, access to the upstream filter device 252a is unfettered by the downstream filter device 252b.

For the depictions of FIGS. 26 and 26A-26D, the downstream filter device 352b is depicted and identified as filter device 250d. It is understood that the double filter arrangements 350, 350a-350d are not limited to the use of filter device 250d in the downstream artery 354b. Rather, the artisan will recognize that any of the filter devices utilized in the upstream artery 354a can also be utilized in the downstream artery 354b, as well as several of the other filter devices disclosed herein.

The context of the double filter arrangement 350 of the description above is for implantation in an innominate and a left carotid artery (FIG. 1). It is understood that the principles of the double filter arrangement 350 are not limited to these arteries, or to the use of only two filter devices. That is, in various embodiments, the principles described can be implemented with any of a variety of take-off arteries and in some cases with more than two arteries, as recognized by the skilled artisan.

While the embodiments depicted in FIGS. 2 through 26D include some form of variation of the porosity of the body 46, it is contemplated that any of the embodiments disclosed herein can be optionally configured with a substantially uniform porosity, such as depicted in FIGS. 1A through 1D.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant art will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

The following references, referred to herein above, are hereby incorporated by reference herein in their entirety except for patent claims and express definitions contained therein above: U.S. Pat. Nos. 6,712,834 and 6,866,680 to Yassour, et al.; U.S. Pat. No. 7,670,356 to Mazzocchi et al.; U.S. Pat. No. 6,258,120 to McKenzie et al.; U.S. Pat. No. 8,430,804 to Belson; U.S. Pat. No. 8,062,324 to Shimon et al.; U.S. Pat. No. 8,460,335 to Carpenter; U.S. Pat. No. 7,862,602 to Licata et al.; and U.S. Patent Application Publication No. 2009/0254172 to Grewe.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

References to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A method for implanting a blood filter that includes a filter portion and an anchor portion, said filter portion including an elbow portion and an extension portion, said elbow portion depending from said anchor portion, said extension portion having a proximal end that defines a bypass aperture, said extension portion including a superior face that defines a first porosity and an inferior face opposite said superior face that defines a second porosity, said first porosity being greater than said second porosity, the method comprising:

disposing said anchor portion in a first artery of an aortic arch;

orienting said filter portion so that said bypass aperture is in a downstream direction of a blood flow in said aortic arch; and positioning said blood filter so that said superior face of said extension portion of said filter portion is in contact with a wall of said aortic arch.

2. The method of claim 1, comprising orienting said extension portion of said filter portion so that said superior face at least partially covers an ostium of a second artery of said aortic arch, said second artery being adjacent said first artery.

3. The method of claim 2, wherein said first artery is an innominate artery and said second artery is a left carotid artery.

* * * * *

UNITED STATES PATENT AND TRADEMARK OFFICE
CERTIFICATE OF CORRECTION

PATENT NO. : 10,213,287 B2
APPLICATION NO. : 15/311398
DATED : February 26, 2019
INVENTOR(S) : Verin et al.

Page 1 of 40

It is certified that error appears in the above-identified patent and that said Letters Patent is hereby corrected as shown below:

Please delete Patent No. 10,213,287 B2 in its entirety and insert Patent No. 10,213,287 B2 in its entirety as shown on the attached pages.

Signed and Sealed this
Twenty-third Day of July, 2019

Andrei Iancu
*Director of the United States Patent and Trademark Office*

(12) United States Patent
Verin et al.

(10) Patent No.: US 10,213,287 B2
(45) Date of Patent: Feb. 26, 2019

(54) IMPLANTABLE SELF-CLEANING BLOOD FILTERS

(71) Applicant: VeoSource SA, Lausanne (CH)

(72) Inventors: Vitali Verin, Geneva (CH); Olivier Coquoz, Geneva (CH)

(73) Assignee: VeoSource SA, Lausanne (CH)

( * ) Notice: Subject to any disclaimer, the term of this patent is extended or adjusted under 35 U.S.C. 154(b) by 151 days.

(21) Appl. No.: 15/311,398

(22) PCT Filed: May 14, 2015

(86) PCT No.: PCT/IB2015/001206
§ 371 (c)(1),
(2) Date: Nov. 15, 2016

(87) PCT Pub. No.: WO2015/173646
PCT Pub. Date: Nov. 19, 2015

(65) Prior Publication Data
US 2017/0086959 A1    Mar. 30, 2017

Related U.S. Application Data

(60) Provisional application No. 61/994,276, filed on May 16, 2014, provisional application No. 62/029,044, filed on Jul. 25, 2014.

(51) Int. Cl.
*A61F 2/01*    (2006.01)
*A61F 2/06*    (2013.01)

(52) U.S. Cl.
CPC .......... *A61F 2/01* (2013.01); *A61F 2002/018* (2013.01); *A61F 2002/068* (2013.01);
(Continued)

(58) Field of Classification Search
CPC ............... A61F 2/01; A61F 2230/0043; A61F 2002/018; A61F 2250/0023;
(Continued)

(56) References Cited

U.S. PATENT DOCUMENTS 5,662,671 A    9/1997    Barbut et al.
5,849,037 A    12/1998    Frid
(Continued)

FOREIGN PATENT DOCUMENTS

JP    2010094141    4/2010
WO    WO0053119    9/2000
(Continued)

*Primary Examiner* — Julian W Woo
(74) *Attorney, Agent, or Firm* — Christensen, Fonder, Dardi & Herbert PLLC

(57) ABSTRACT

A blood filter device having occlusion-resistant characteristics. The occlusion-resistant characteristics decrease the likelihood of the filter being blocked by thrombi. The filter device (252a, 252b) includes at least one anchor portion (42) for anchoring the filter device within one or more arteries (354a, 354b), and a filter portion (98) for filtering thrombi from the blood entering the artery. In some embodiments, an anchor portion is capped with a filter cap. In various embodiments, the filter cap is protrudes into the aorta to promote occlusion resistance. In one embodiment, the device can be modified in situ to re-establish normal blood flow through the artery in the unlikely case of thrombotic or other blockage of the filter. In some embodiments, a bypass opening or open channel defining an access port is provided to accommodate passage of surgical instruments into the artery and to enable blood flow to bypass the filter should the filter become heavily occluded.

3 Claims, 22 Drawing Sheets

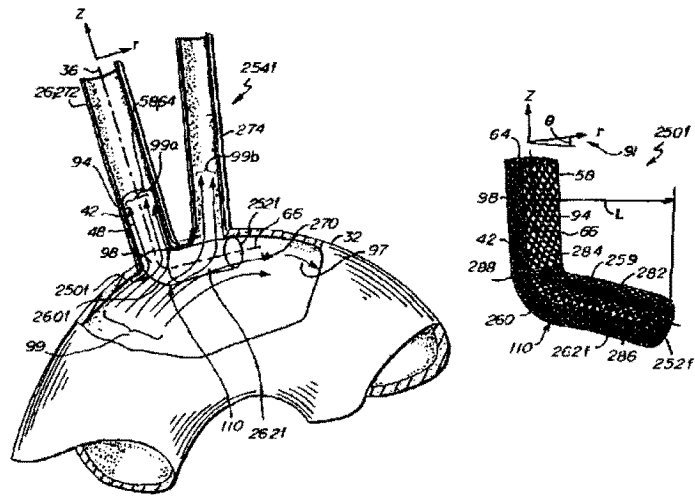

(52) U.S. Cl.
CPC .............. *A61F 2230/0043* (2013.01); *A61F 2230/0069* (2013.01); *A61F 2230/0093* (2013.01); *A61F 2250/0023* (2013.01)

(58) Field of Classification Search
CPC ......... A61F 2230/0069; A61F 2002/068; A61F 2230/0093
USPC .......................................................... 623/1.36
See application file for complete search history.

(56) References Cited

U.S. PATENT DOCUMENTS

| | | |
|---|---|---|
| 5,855,600 A | 1/1999 | Alt |
| 5,938,697 A | 8/1999 | Killion et al. |
| 6,136,022 A | 10/2000 | Nunez et al. |
| 6,241,746 B1 | 6/2001 | Bosma et al. |
| 6,258,115 B1 | 7/2001 | Dubrul |
| 6,258,120 B1 | 7/2001 | McKenzie et al. |
| 6,273,910 B1 | 8/2001 | Limon |
| 6,312,463 B1 | 11/2001 | Rourke et al. |
| 6,348,063 B1 | 2/2002 | Yassour et al. |
| 6,635,070 B2 | 10/2003 | Leeflang et al. |
| 6,652,554 B1 | 11/2003 | Wholey et al. |
| 6,673,089 B1 | 1/2004 | Yassour et al. |
| 6,695,858 B1 | 2/2004 | Dubrul et al. |
| 6,712,834 B2 | 3/2004 | Yassour et al. |
| 6,740,112 B2 | 5/2004 | Yodfat et al. |
| 6,866,680 B2 | 3/2005 | Yassour et al. |
| 6,929,653 B2* | 8/2005 | Streeter ................ A61F 2/013 128/898 |
| 7,156,858 B2 | 1/2007 | Schuldt-Hempe et al. |
| 7,670,356 B2 | 3/2010 | Mazzocchi et al. |
| 7,763,011 B2 | 7/2010 | Ortiz et al. |
| 7,780,694 B2 | 8/2010 | Palmer et al. |
| 7,857,843 B2 | 12/2010 | Henderson |
| 7,927,346 B2 | 4/2011 | VanCamp et al. |
| 8,062,324 B2 | 11/2011 | Shimon et al. |
| 8,192,484 B2 | 6/2012 | Frid |
| 8,211,158 B2 | 7/2012 | Wolf |
| 8,221,446 B2 | 7/2012 | Pal et al. |
| 8,252,017 B2 | 8/2012 | Paul, Jr. et al. |
| 8,252,020 B2 | 8/2012 | Hauser et al. |
| 8,353,943 B2 | 1/2013 | Kuppurathanam et al. |
| 8,388,644 B2 | 3/2013 | Parker |
| 8,430,904 B2 | 4/2013 | Belson |
| 8,460,335 B2* | 6/2013 | Carpenter ................ A61F 2/013 606/200 |
| 8,506,619 B2 | 8/2013 | Ortiz et al. |
| 8,597,342 B2 | 12/2013 | McKinsey et al. |
| 8,679,149 B2* | 3/2014 | Belson ................ A61F 2/01 606/200 |
| 8,715,317 B1* | 5/2014 | Janardhan ................ A61F 2/01 606/200 |
| 8,728,152 B2 | 5/2014 | Goldmann et al. |
| 8,911,504 B2 | 12/2014 | Mathisen et al. |
| 8,940,040 B2* | 1/2015 | Shahriari ................ A61F 2/07 623/1.35 |
| 8,979,918 B2 | 3/2015 | Murayama |
| 9,039,754 B2 | 5/2015 | Nishigishi |
| 9,044,305 B2 | 6/2015 | Grewe |
| 9,204,953 B2 | 12/2015 | Mortarino |
| 9,326,840 B2 | 5/2016 | Mortarino |
| 9,427,494 B2 | 8/2016 | Persson et al. |
| 9,510,925 B2 | 12/2016 | Hotter et al. |
| 10,076,400 B2* | 9/2018 | Krahbichler ............ A61F 2/013 |
| 2003/0100940 A1 | 5/2003 | Yodfat |
| 2007/0021816 A1 | 1/2007 | Rudin |
| 2007/0198075 A1 | 8/2007 | Levy |
| 2009/0171451 A1 | 7/2009 | Kuppurathanam et al. |
| 2011/0040372 A1 | 2/2011 | Hansen et al. |
| 2012/0265289 A1 | 10/2012 | Macatangay |
| 2013/0150882 A1 | 6/2013 | Williams et al. |
| 2013/0211497 A1 | 8/2013 | Charlebois et al. |
| 2014/0114340 A1 | 4/2014 | Zhou et al. |

FOREIGN PATENT DOCUMENTS

| | | |
|---|---|---|
| WO | WO2005027751 | 3/2005 |
| WO | WO2006131930 | 12/2006 |
| WO | WO2008073964 | 6/2008 |

* cited by examiner

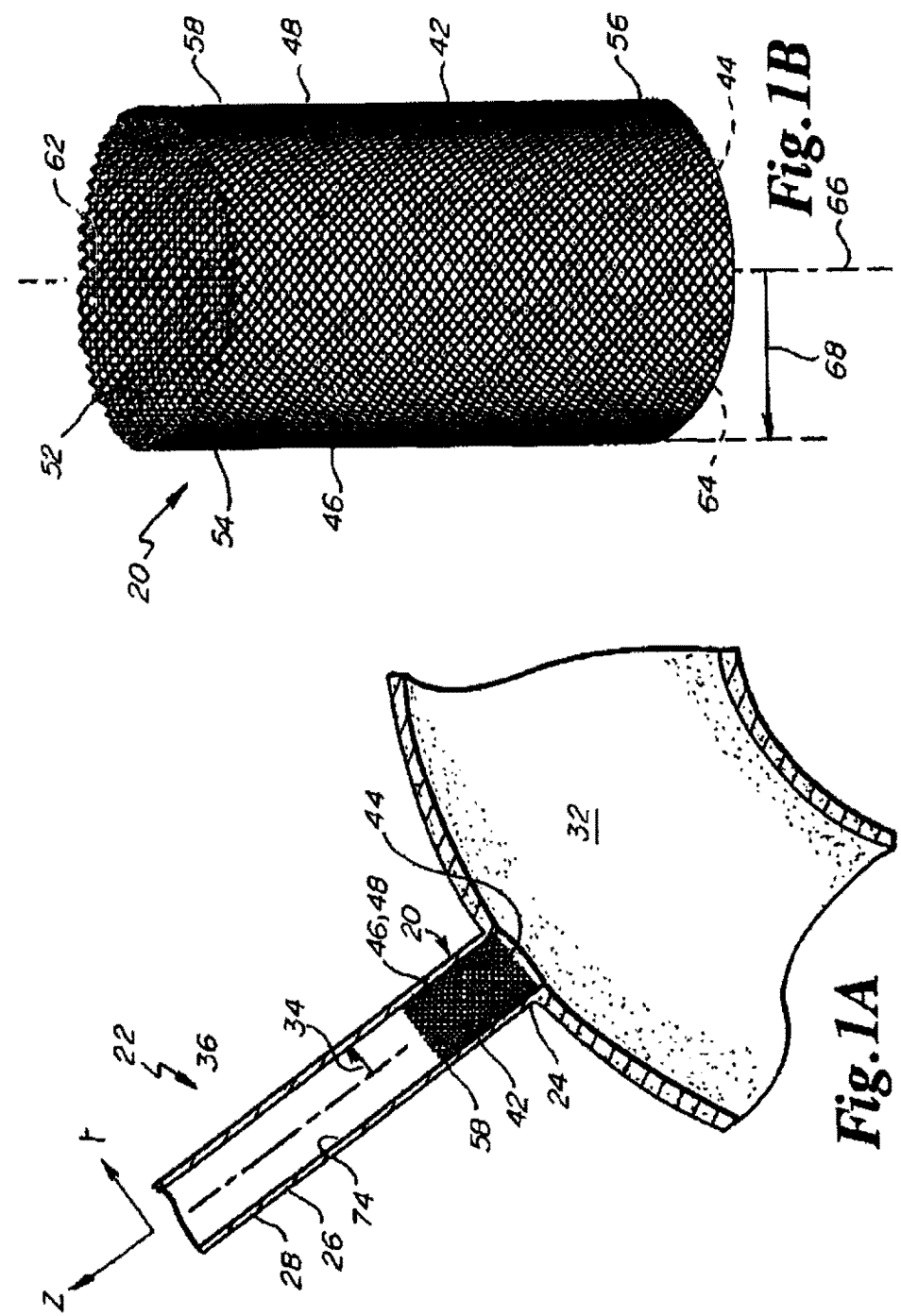

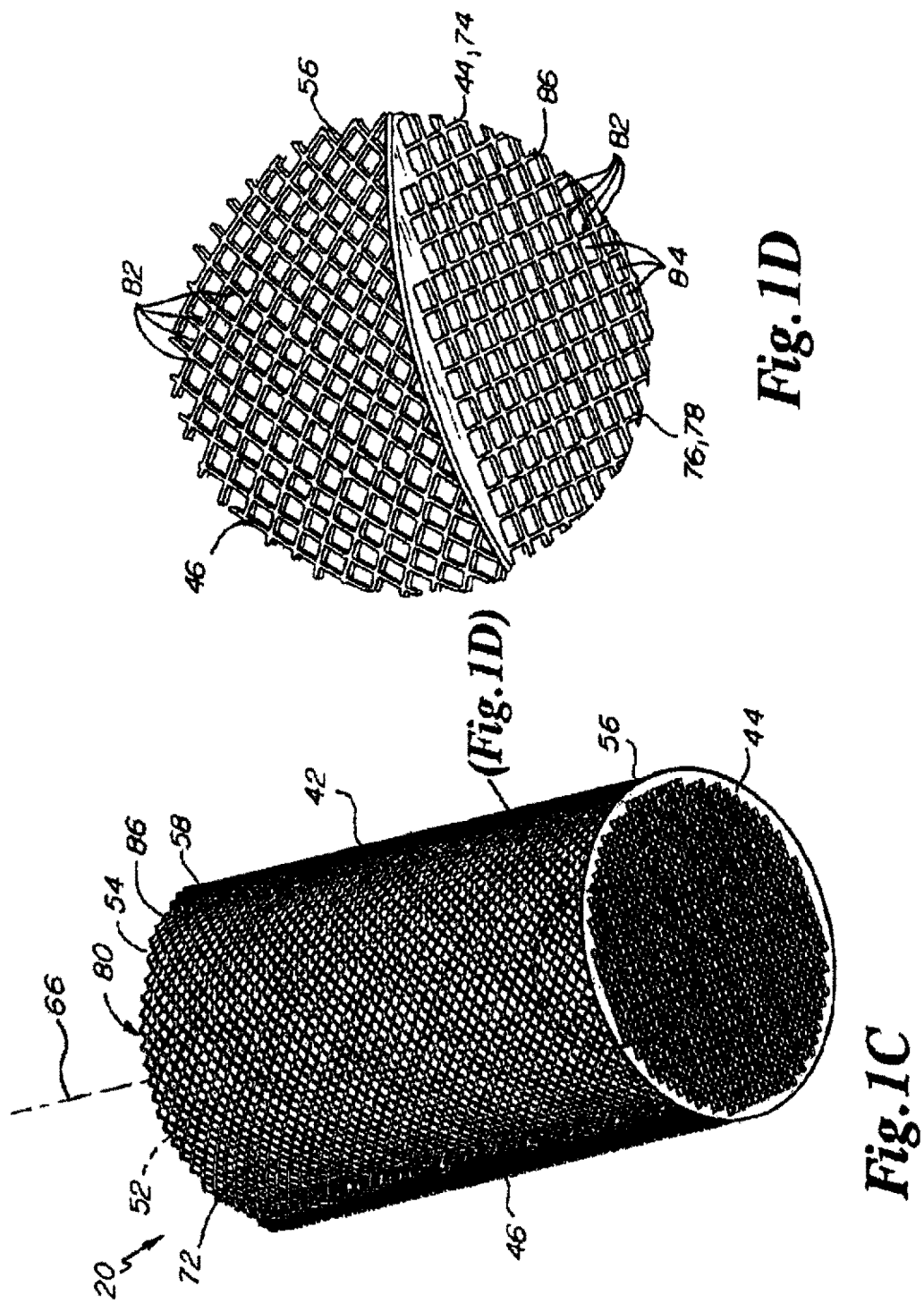

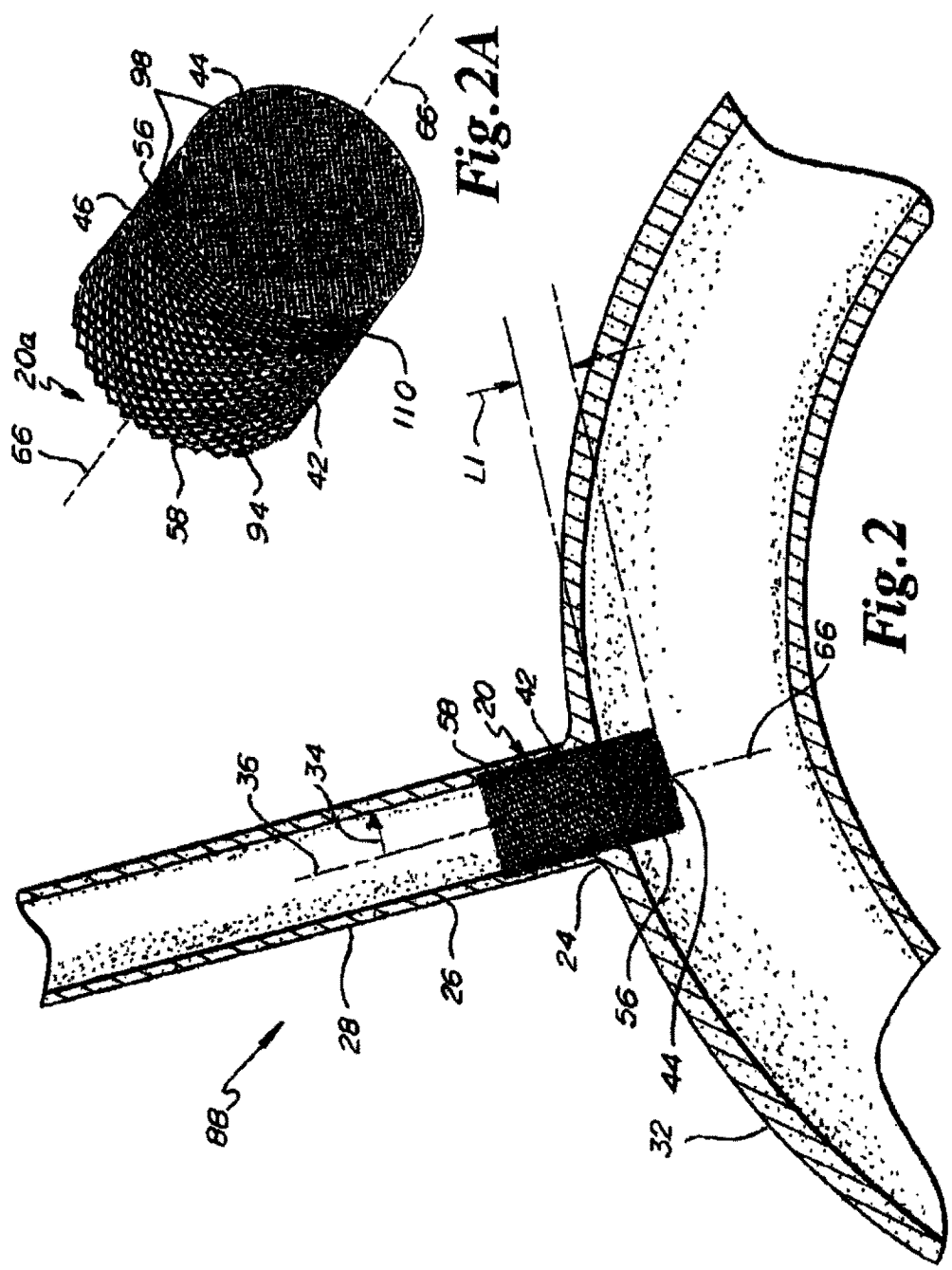

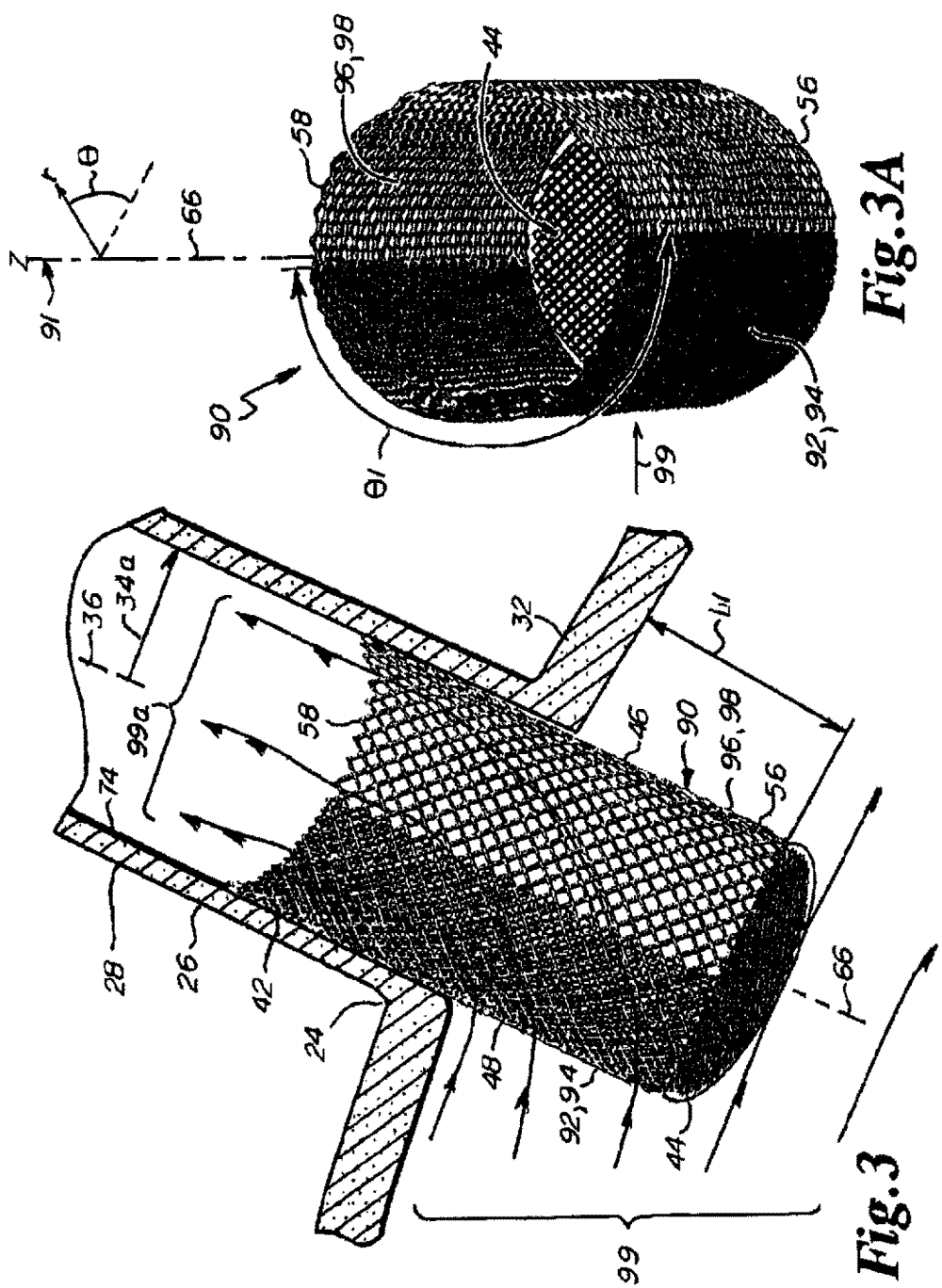

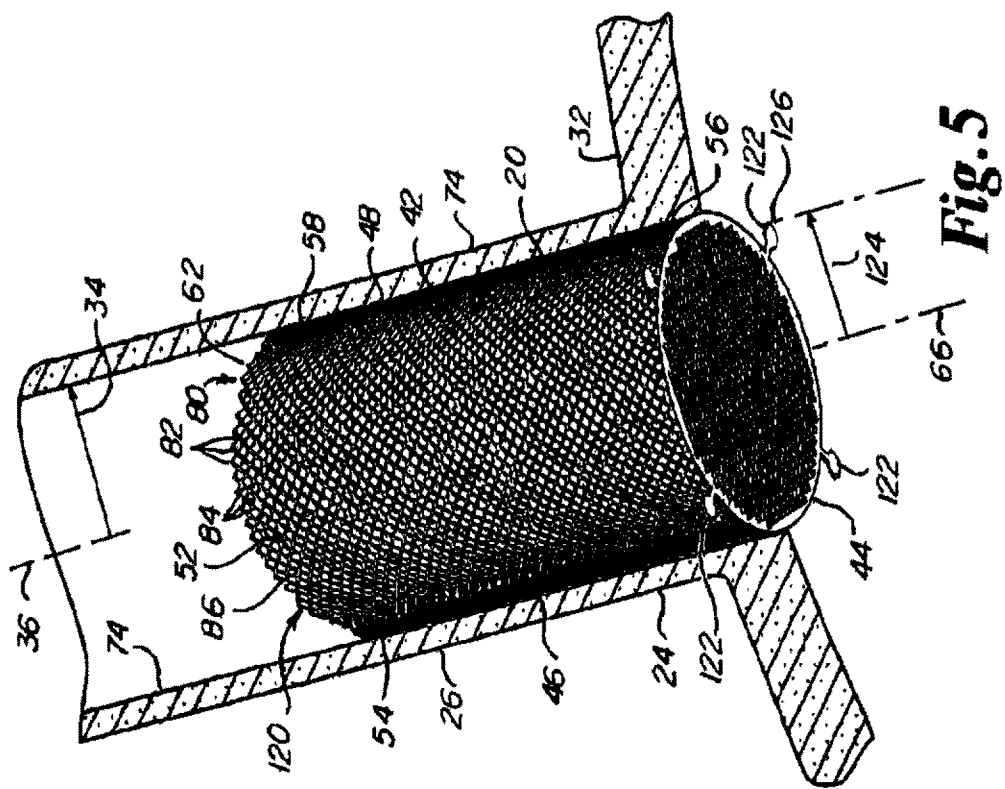
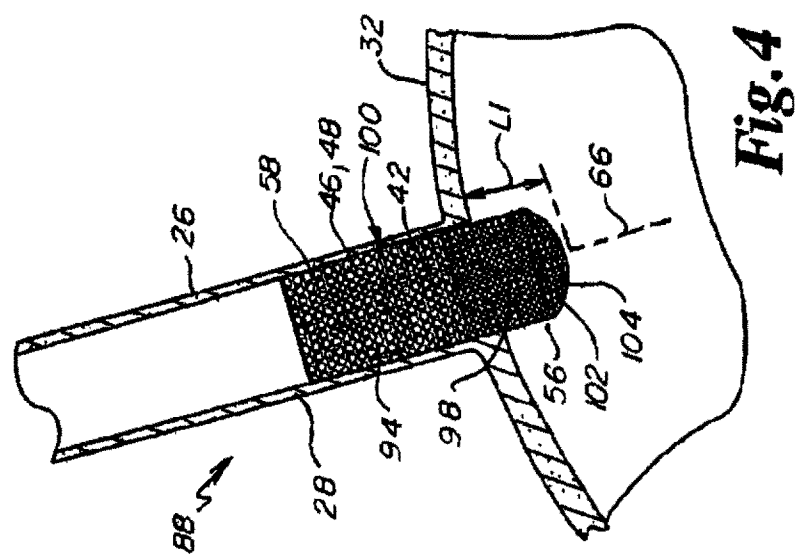

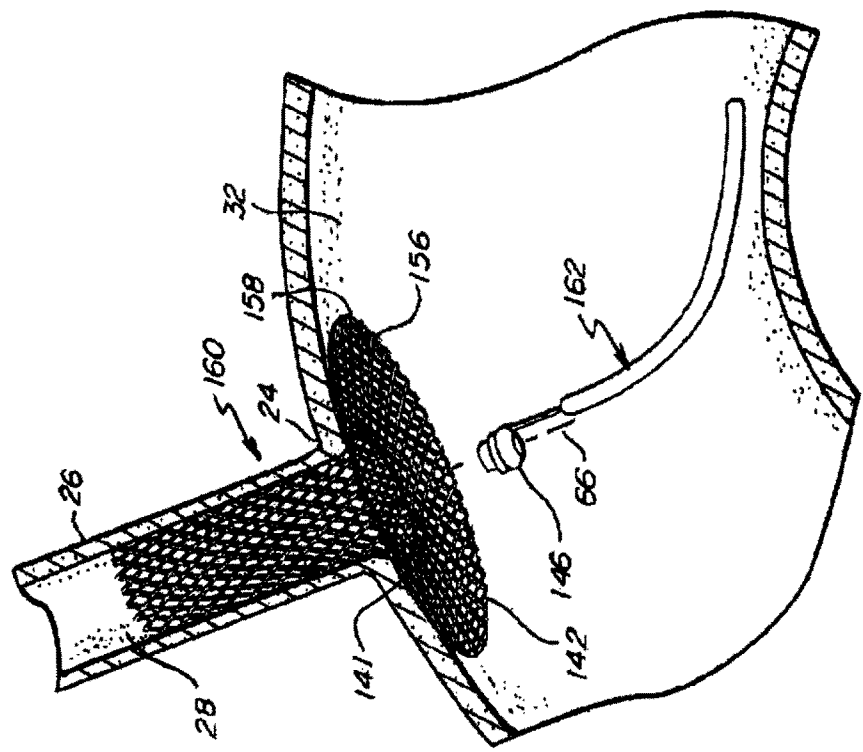
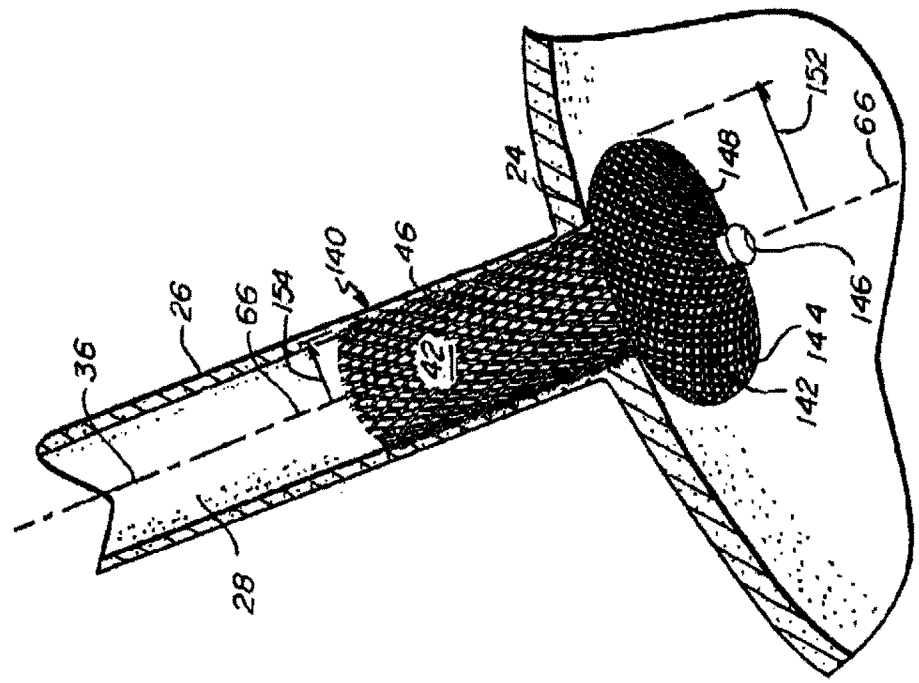

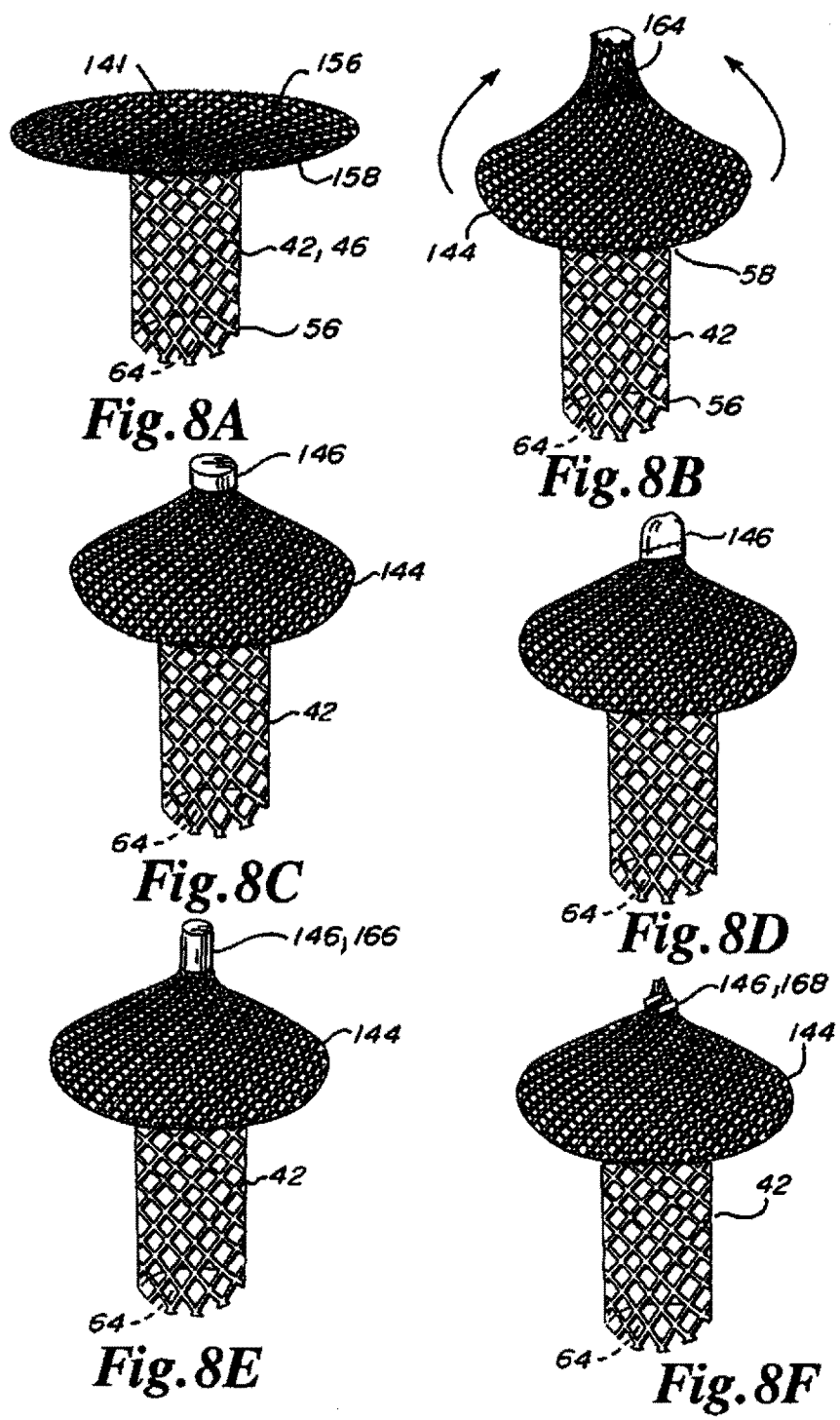

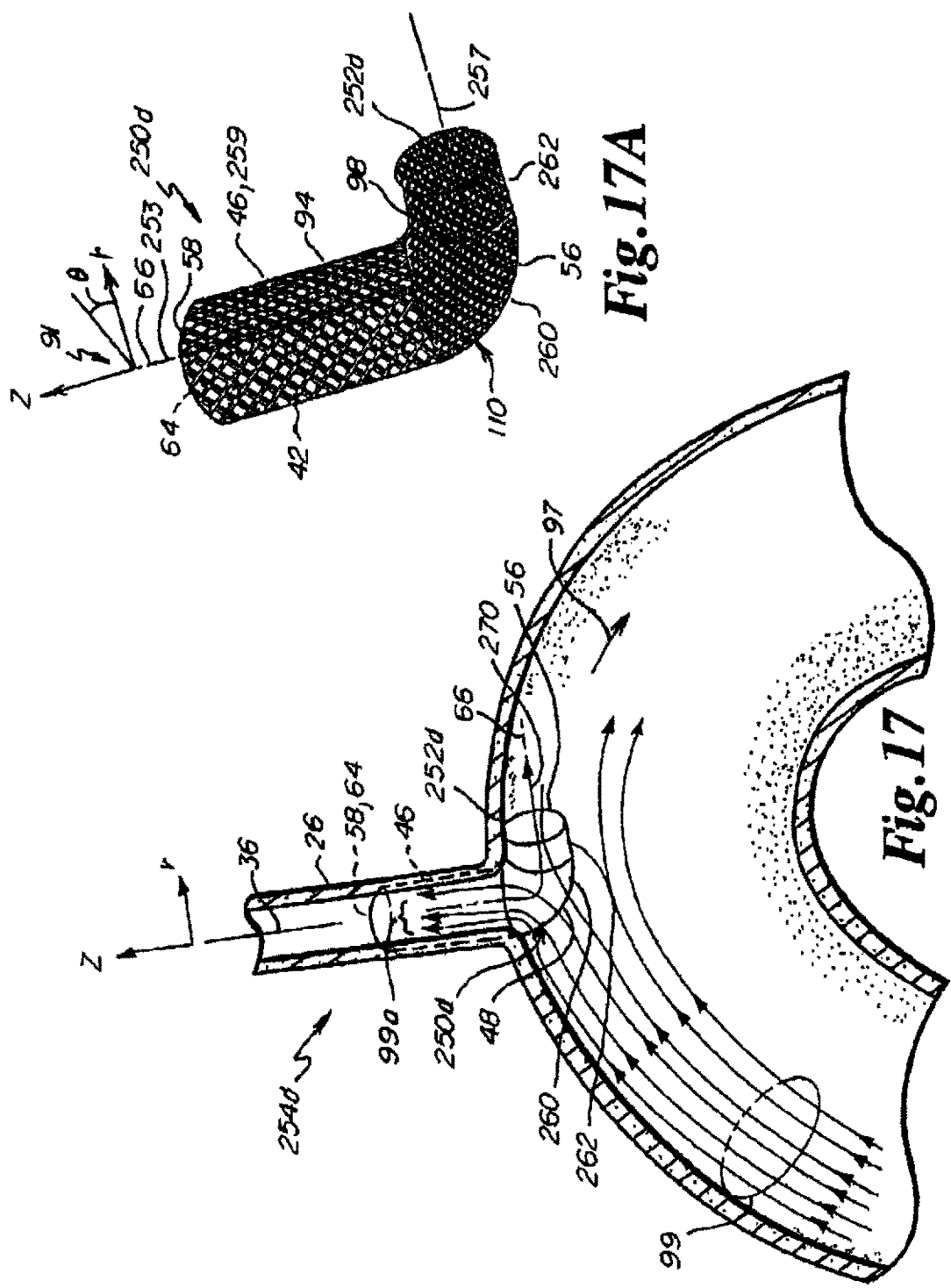

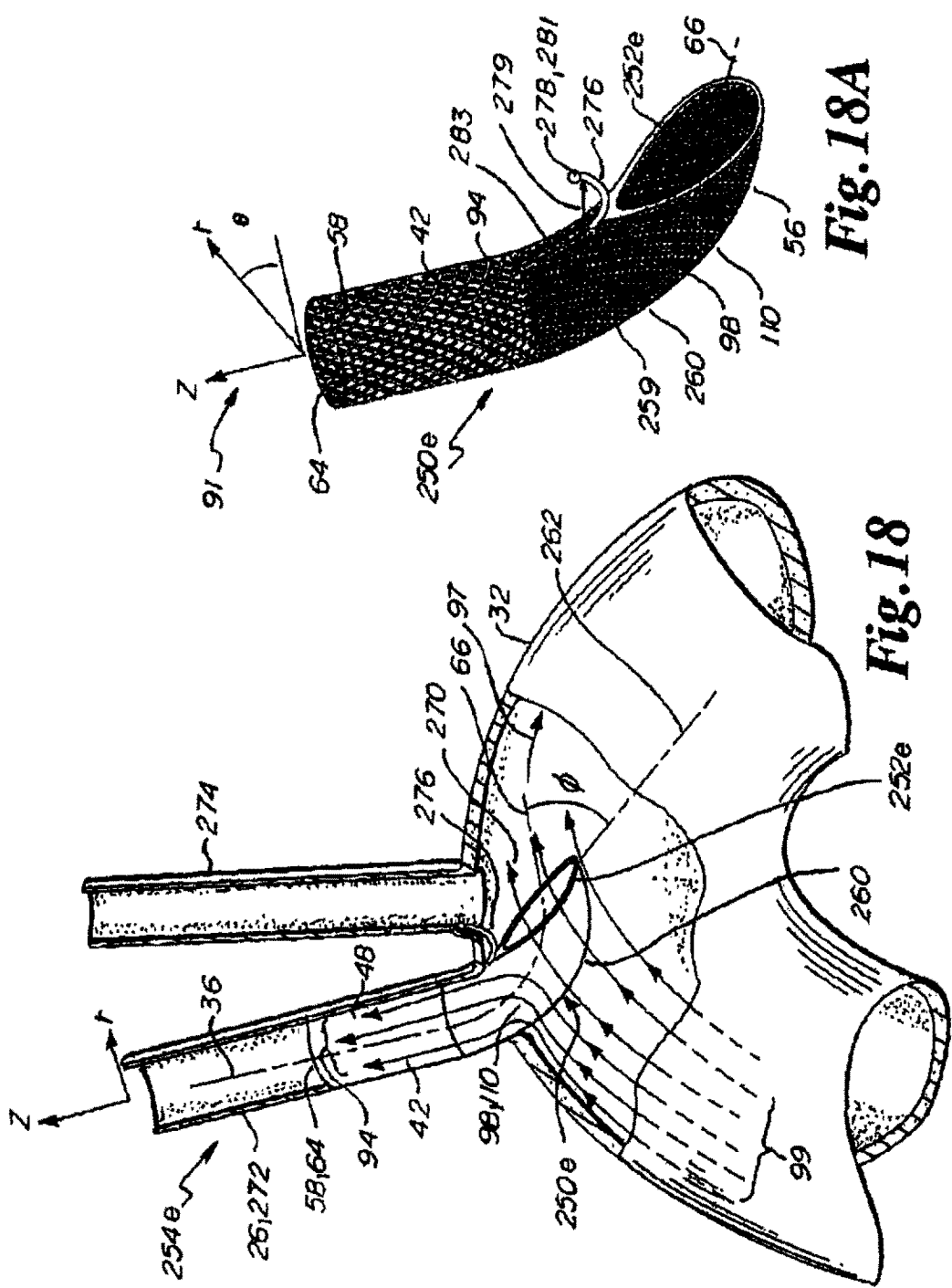

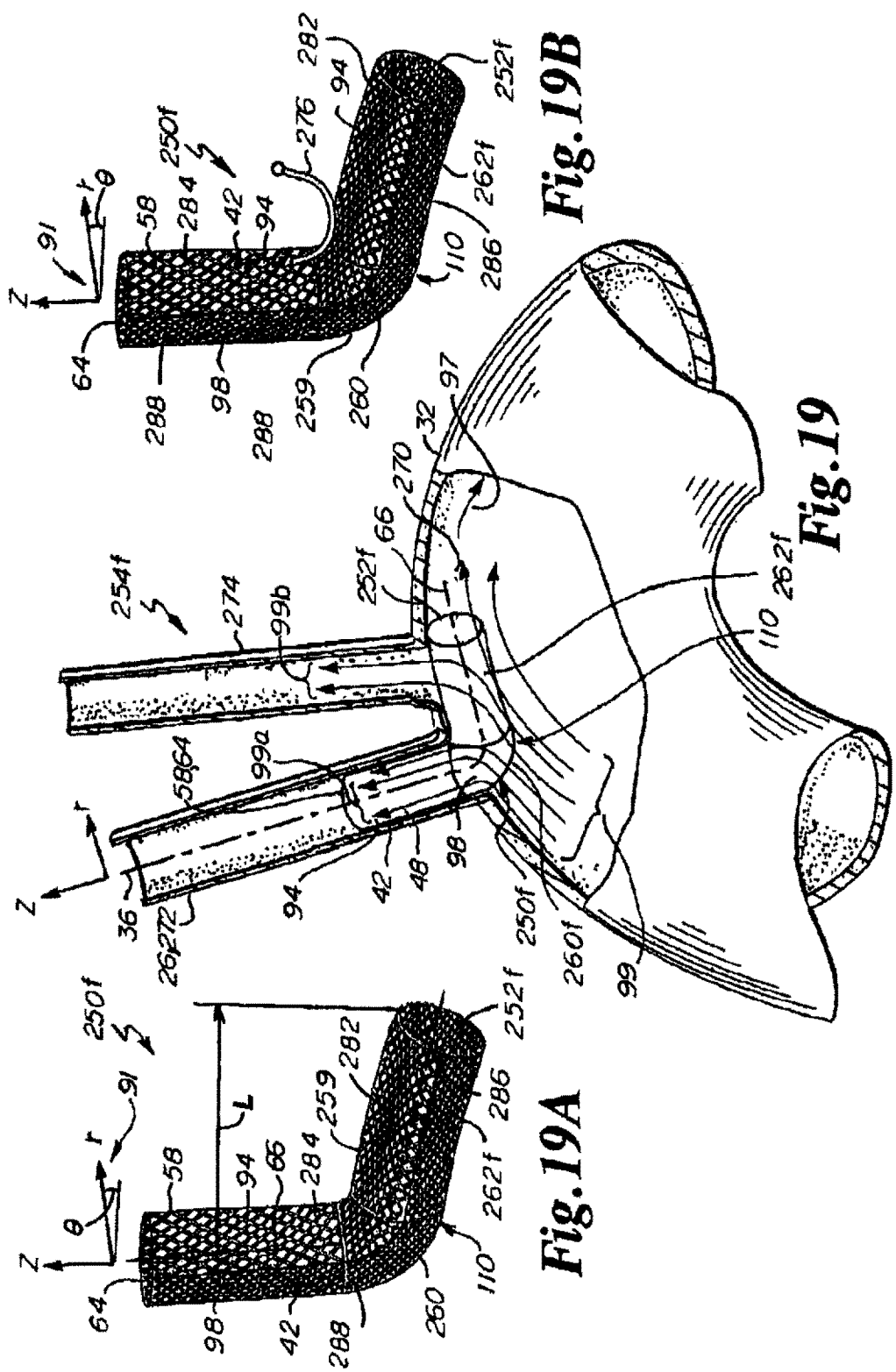

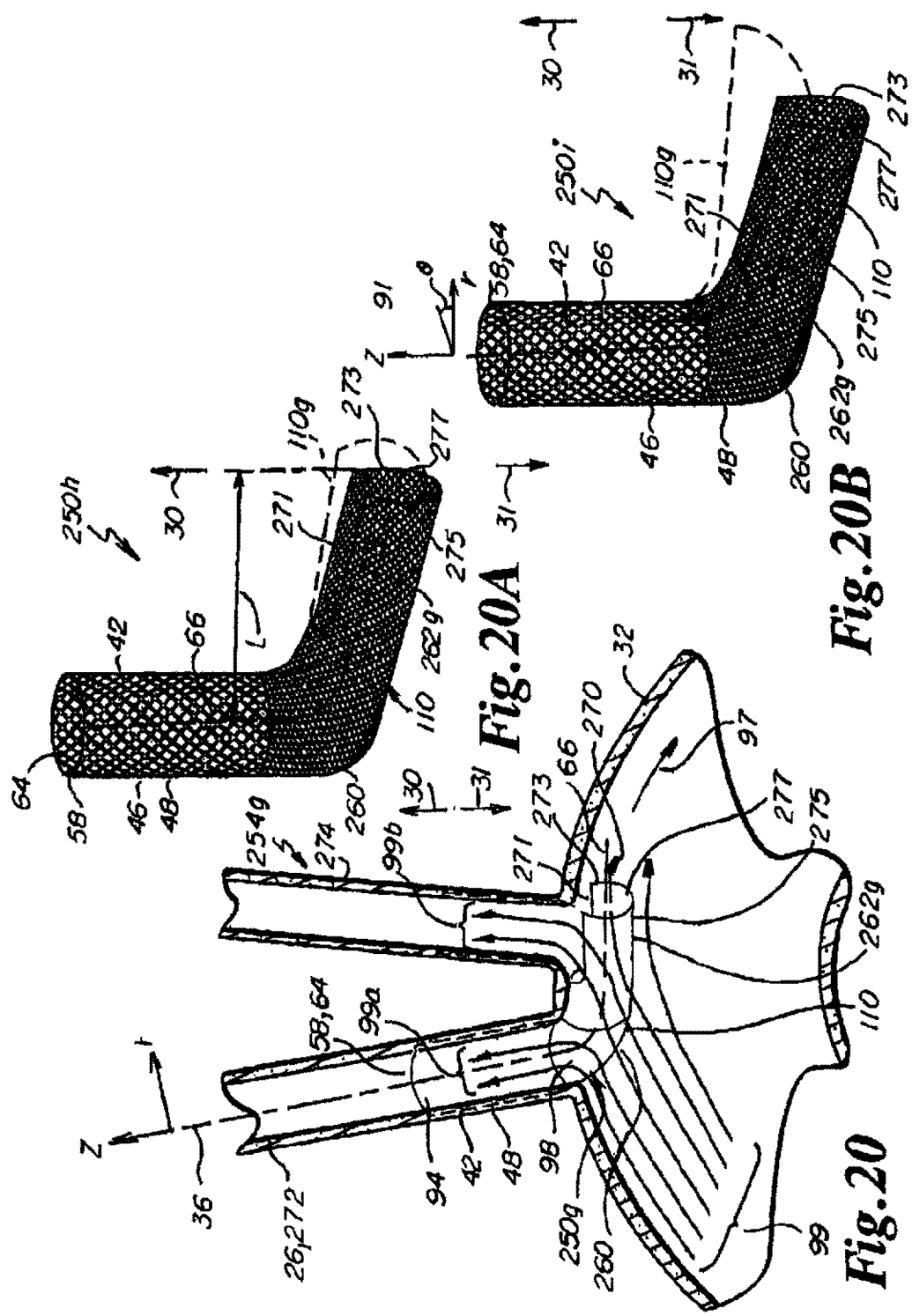

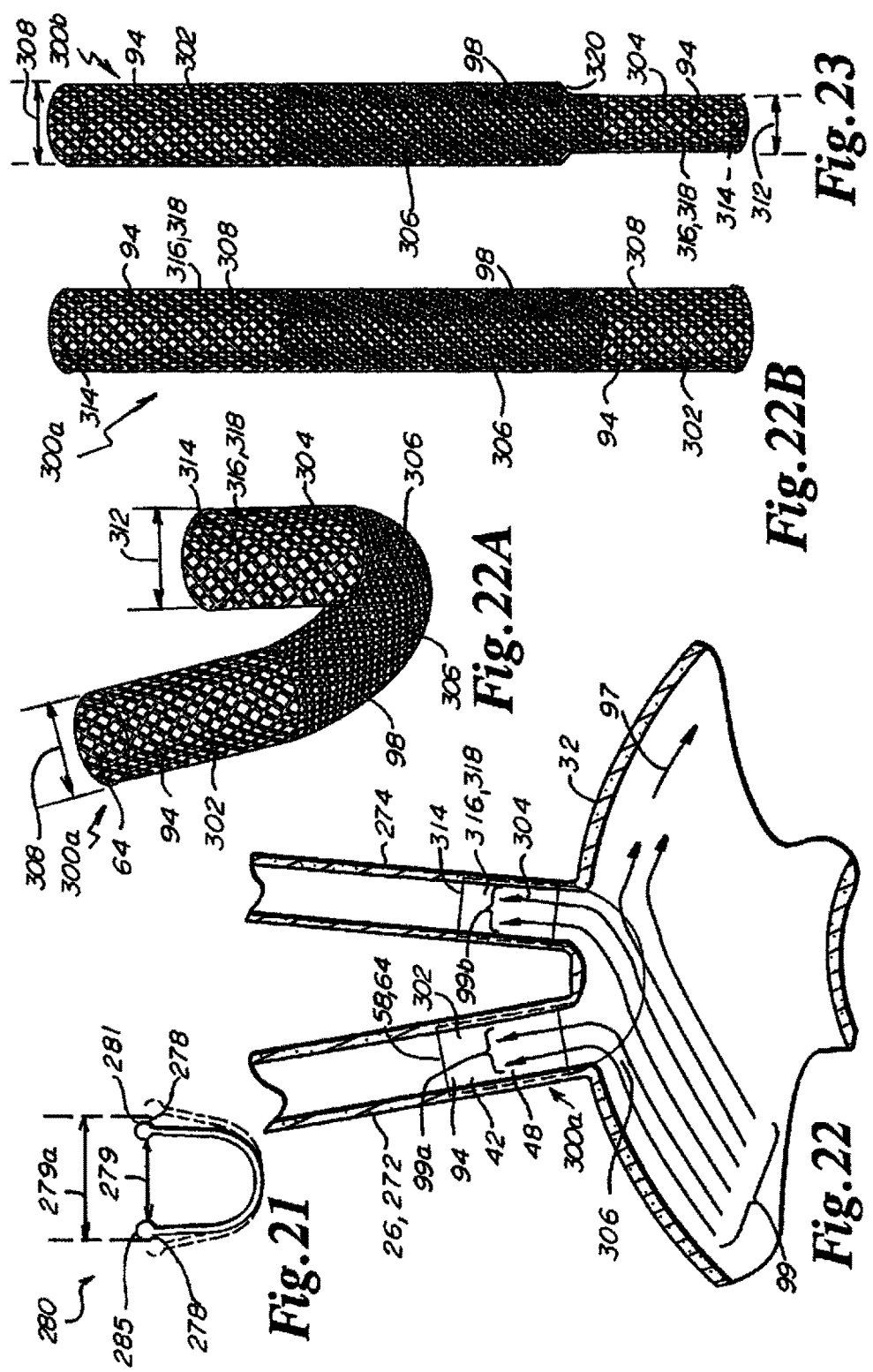

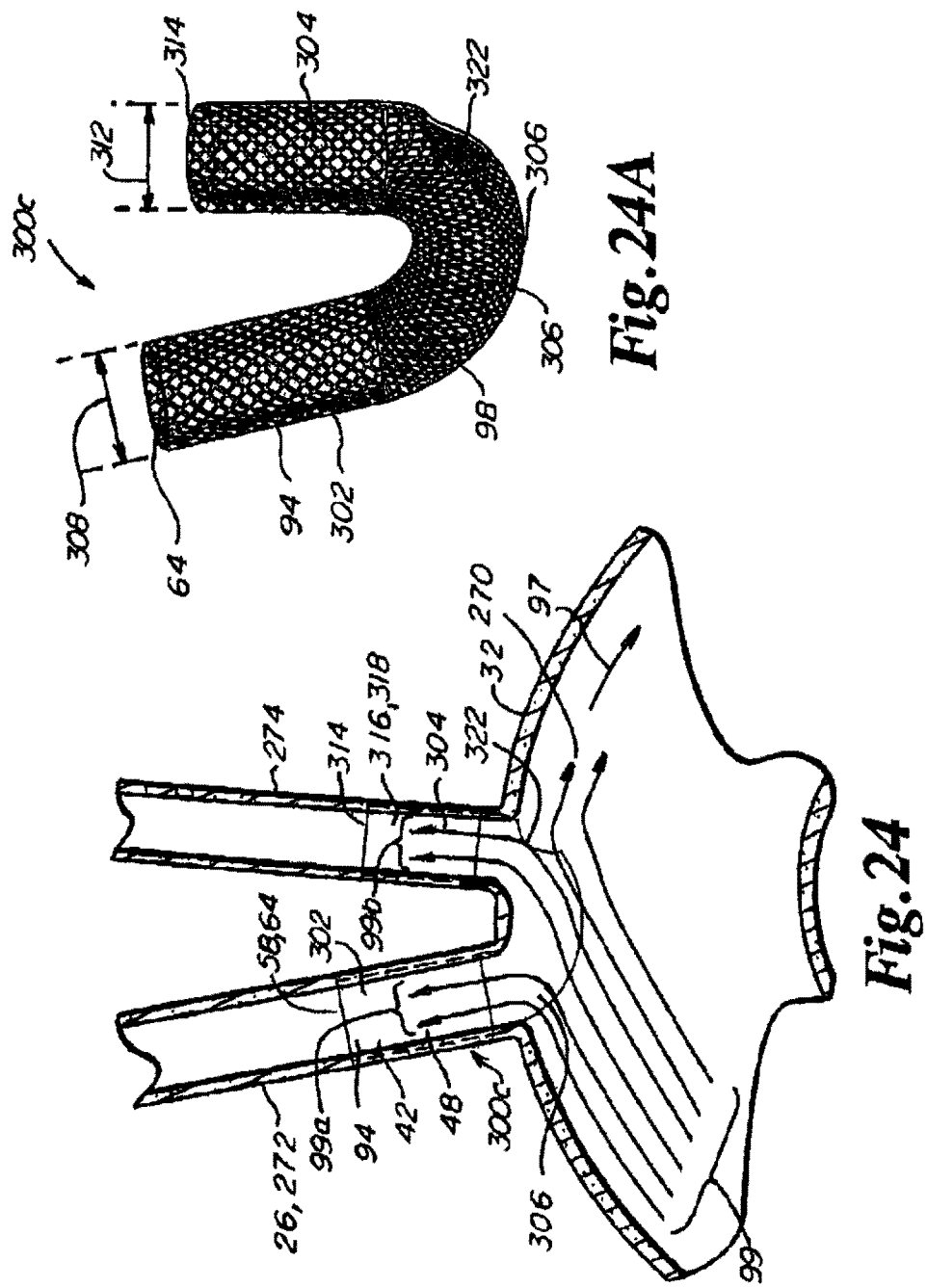

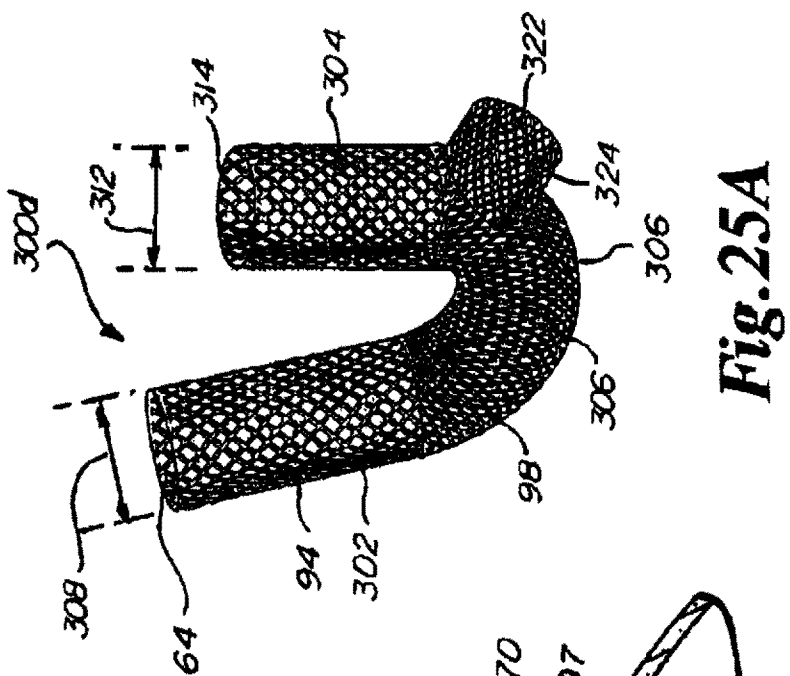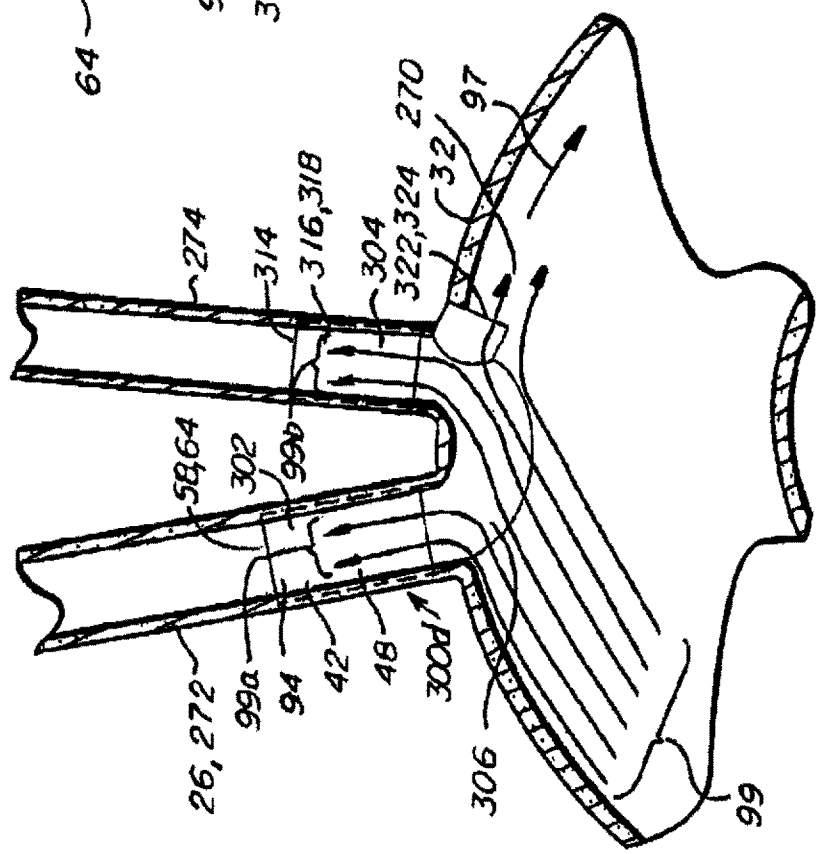

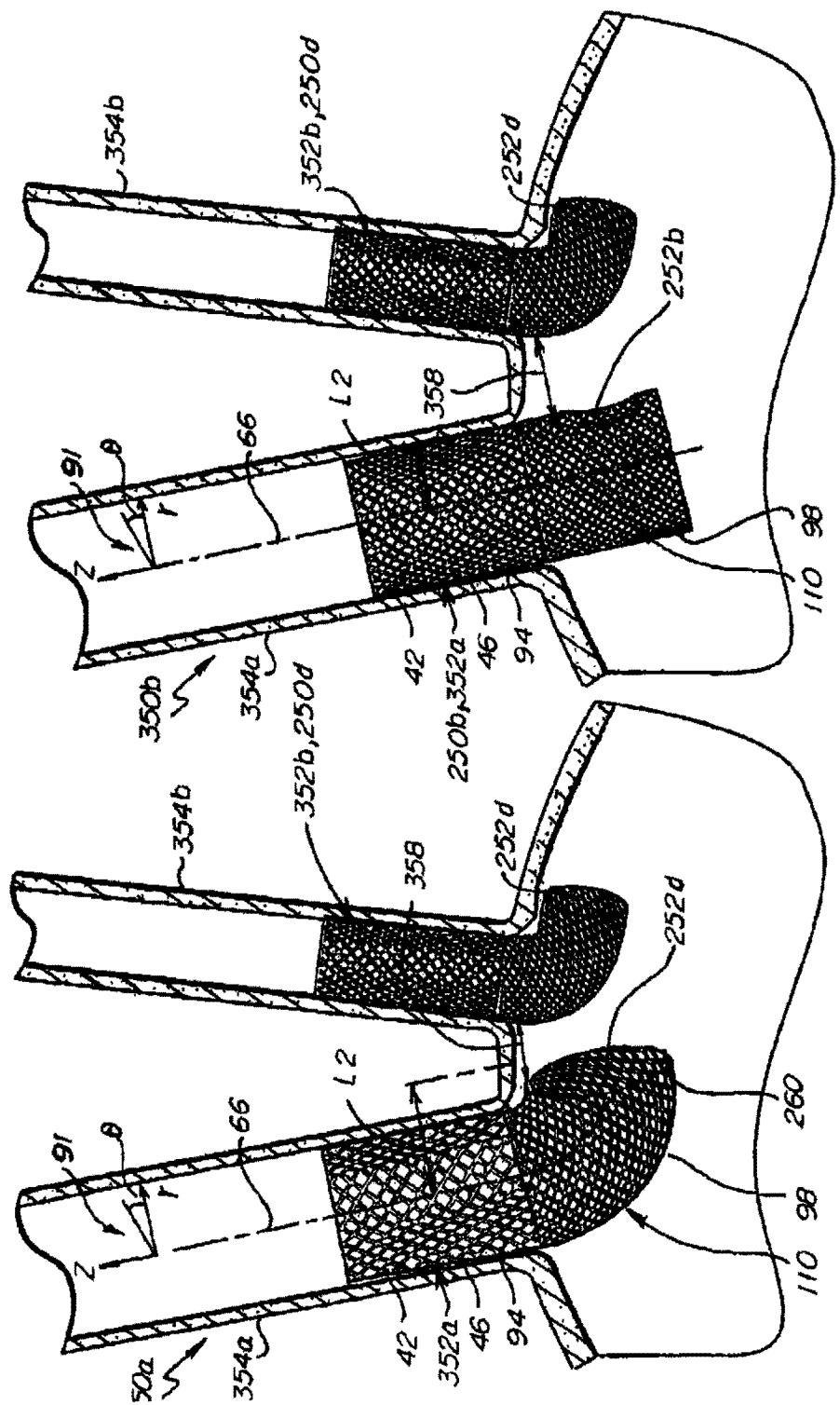

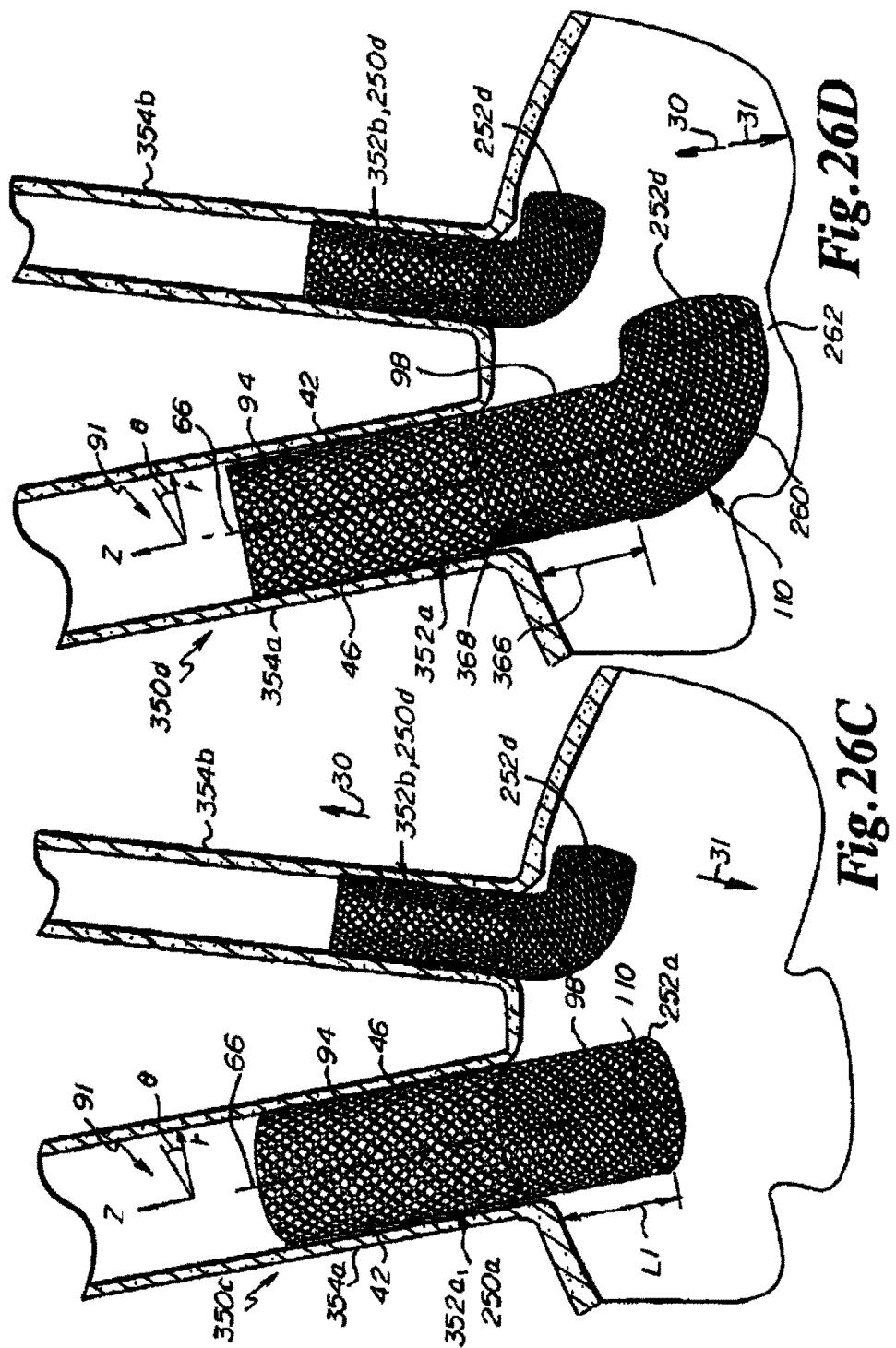

IMPLANTABLE SELF-CLEANING BLOOD FILTERS

RELATED APPLICATIONS

This patent application is a National Phase entry of PCT Application No. PCT/IB2015/001206, filed May 14, 2015, which claims the benefit of U.S. Provisional Patent Application No. 61/994,276, filed May 16, 2014, and of U.S. Provisional Patent Application No. 62/029,044, filed Jul. 25, 2014, the disclosures of which are hereby incorporated by reference in their entirety.

FIELD OF THE DISCLOSURE

The present disclosure is directed generally to implantable blood filter devices and more specifically to filter devices to protect the brain and other organs from emboli.

BACKGROUND OF THE DISCLOSURE

Various conventional devices exist to contain or control the flow of thrombic material and atheroma debris. Examples of such devices include U.S. Pat. Nos. 6,712,834 and 6,866,680 to Yassour, et al., and U.S. Pat. No. 7,670,356 to Mazzocchi et al., which disclose blood filter devices designed to capture the debris material. A concern with capture filters is that they can foul to the extent that blockage of blood flow develops, with obvious consequences. Accordingly, these devices are typically unsuitable for long term or permanent implantation.

In another approach, U.S. Pat. No. 6,258,120 to McKenzie et al., U.S. Pat. No. 8,430,904 to Belson, U.S. Pat. No. 8,062,324 to Shimon et al., and U.S. Patent Application Publication No. 2009/0254172 to Grewe are directed to aortic diverters that divert emboli away from arteries. Diverter-type devices are limited to certain artery junction structures where flow diversion is a suitable substitute for filtering, and, in many instances, do not provide a positive barrier to emboli, either by design or because of the way they are mounted within the aorta. Furthermore, these devices can foul with debris build up over time, leaving no recourse for remedying the fouling, and so are not suitable for long term or permanent implantation. Also, diverter devices that are based on anchoring in the aorta require large diameter catheters for delivery. Other diverter-type devices include U.S. Pat. No. 8,460,335 to Carpenter, are held in place by the attendant deployment means, and thus suitable only for temporary service.

A blood filter device that overcomes the aforementioned shortcomings of conventional blood filters and aortic diverters would be welcomed.

SUMMARY OF THE DISCLOSURE

In various embodiments, a blood filter device is disclosed that combines the advantages of a positive blood filter device with the diversionary advantages of aortic diverters to provide a blood filter device that is occlusion-resistant. In some embodiments, the blood filter device is suitable for either temporary filtering or permanent or long term filtering. In one embodiment, the blood filter device can be withdrawn from the artery using a percutaneous technique. In some embodiments, the device can be reconfigured or opened up in situ to re-establish normal blood flow through the artery in the unlikely case of thrombotic or other blockage of the filter.

In some embodiments, the disclosed blood filter is inserted into the ostium (take-off) of the major body artery, e.g., a branch of the aorta to filter the blood flowing into this artery from the aorta. In one embodiment, the device is designed in a way that, when inserted into the ostium of the branch of the aorta, a filter cap of the device is located in the same geometrical plane as the take-off (ostium) of the artery. In other embodiments, the filter cap protrudes into the lumen of the aorta. The projection of the filter cap into lumen of the aorta enables self-cleaning of the filter cap by the aorta blood flow that effectively purges the filtering surface of thrombi and atheroma debris and prevents the filter cap from being blocked by such emboli. This preserves the patency of the filter. In certain embodiments, the blood filter provides a physician with a capability of opening the filter in situ and with minimal invasiveness in the event that the filter cap becomes significantly blocked by thrombi and/or debris and/or other embolic material.

In various embodiments, the occlusion resistant aspects of the blood filter device is also augmented by the orientation of the filtering cap relative to the direction of the blood flow. The filter cap of the filter device is located upstream of the anchor portion, as compared with prior art devices where filter is located downstream of a stent. In addition, certain embodiments implement a convex surface that bows in the direction of the blood flow, whereas other prior art filters present a concave surface relative to blood flux.

In various embodiments, the filter device defines both a coarse porosity and a fine porosity. The coarse porosity can promote tissue ingrowth for anchoring of permanently implanted devices; the fine porosity is suitable for the filtering function.

In some embodiments, a filter device is configured to be inserted in one artery and oriented to cover an ostium of a second adjacent artery. Optionally, various embodiments are configured to be inserted into both ostia of the adjacent arteries, with a tubular filter portion being supported therebetween. Such filter devices provide filtering or diversionary protection from incursion of thrombi and atheroma debris to the adjacent arteries.

The blood filter device of various embodiments can be left in an aortic branch take-off for a short period of time (hours, days, or weeks) in case of acute interventional procedure such as percutaneous aortic valve replacement (TAVI), heart or aortic surgery, AF ablation procedure, and treatment of infectious endocarditis. For short-term uses, the device could be withdrawn using percutaneous technique at a physician's discretion after implantation. Optionally, some embodiments can be utilized as a permanent implant in patients posing a chronic risk of embolic complications such as atrial fibrillation, degenerative and autoimmune valvular disease, atheromatous disease of aorta, patent foramen ovale or recurrent stroke of unknown origin.

Various embodiments of the disclosed filter device can be put into any branch of the aorta, including brachiocephalic arteries, as well as renal, and mesenteric arteries.

Structurally, various embodiments of a blood filter for filtering blood entering an artery are disclosed, comprising a body that includes an anchor portion defining a flow outlet port at a first end of the body and including a porous wall that defines a first porosity, and a filter portion that extends from the anchor portion and includes a porous wall that defines a second porosity, the second porosity being less than the first porosity. In one embodiment, the filter portion defines a second end of the body, the second end defining a bypass aperture.

In some embodiments, the body defines a straight cylinder. Optionally, the blood filter comprises one of a flange and a plurality of protrusions extending laterally outward from the body. In some embodiments, the one of the flange and the plurality of protrusions are disposed proximate a junction between the anchor portion and the filter portion.

In other embodiments, the body defines a curved cylinder about a curved body axis. Optionally, a first tangential portion of the filter portion defines the second porosity, and a second tangential portion of the filter portion defines the first porosity. In one embodiment, the bypass aperture lies substantially on a plane, and the curved body axis intersects the plane at an acute angle. Various embodiments optionally include a centering hook structure coupled to the anchor portion that projects laterally outward from the anchor portion.

In various embodiments of the disclosure, a filter cap is coupled to the filter portion. A maximum lateral dimension of the filter cap can be less than or equal to a diameter of the body, with the filter cap being planar. For some embodiments, the filter portion defines a lateral bypass aperture. Optionally, the blood filter further comprises a shroud surrounding the lateral bypass aperture.

In various embodiments, the filter cap is bulbous. Optionally, the filter cap also includes a hub that is removable for defining an open configuration of the blood filter, the open configuration enabling blood to flow through the anchor portion unfiltered. Optionally, the filter cap defines a bypass aperture. In one embodiment, the anchor portion is concentric about a central axis, and the bypass aperture defines a normal vector having a lateral component relative to the central axis. In one embodiment, the filter cap includes a cover that covers the bypass aperture, the cover being removable for selective access to the blood filter through the bypass aperture. Optionally, the cover includes a hub. In various embodiments, the filter cap and the body are unitary. In some embodiments, the body includes a flange portion, the bulbous portion being configured to register against the flange portion. Optionally, the flange portion and the body are unitary. In certain embodiments, a stem portion extends from the bulbous portion, the stem portion being dimensioned for removable insertion into the body. Optionally, the stem portion and the bulbous portion are unitary.

In various embodiments of the disclosure, a dual anchor configuration is disclosed, wherein the body further comprises a second anchor portion defining a second flow outlet port and including a porous wall that defines a third porosity. The third porosity can be configured to be substantially the same as the first porosity. In one embodiment, the anchor portion is dimensioned for anchoring to an innominate artery and the second anchor portion is dimensioned for anchoring to a left carotid artery. Optionally, the anchor portion defines a first diameter, the second anchor portion defines a second diameter, the second diameter being less than the first diameter.

The filter portion of the dual anchor embodiments can also define a lateral bypass aperture. Optionally, the filter comprises a shroud surrounding the lateral bypass aperture. In various embodiments, the second anchor portion extends from a second end of the filter portion, the second end of the filter portion being opposed to the first end of the filter portion. In some embodiments, the filter portion is configured to define a U-shape in an implanted configuration wherein the filter portion is inferior to both the anchor portion and the second anchor portion in the implanted configuration. Optionally, all of the U-shape has the second porosity.

For various embodiments, the filter portion is dimensioned to extend from an ostium of an innominate artery to cover an ostium of a left carotid artery. The anchor portion can be concentric about a central axis, with the filter portion including an elbow-shaped portion and extending lateral to the anchor portion to define a lateral dimension referenced from the central axis, the lateral dimension being in a range of 20 mm to 60 mm inclusive; in some embodiments, in a range from 20 mm to 40 mm inclusive; in some embodiments, in a range from 20 mm to 35 mm inclusive. (Herein, a range that is said to be "inclusive" includes the endpoint values of the stated range.) In some embodiments, the filter portion defines a diameter in a range of 6 mm to 20 mm inclusive; in some embodiments, in a range from 8 mm to 18 mm inclusive; in some embodiments, in a range from 10 mm to 15 mm inclusive.

In various embodiments, the body portion comprises one of a bio-absorbable alloy and a bio-absorbable polymer. Optionally, the body portion comprises a material selected from the group consisting of stainless steel, platinum, platinum-iridium alloys, nickel-cobalt alloys, nickel-titanium alloys, magnesium based alloys, polyethylene terephthalate, polyurethane, and polylactic acid based polymers.

In some embodiments, the porous wall of the filter portion defines a porosity in the range of 50% to 98% inclusive; in some embodiments, in a range from 60% and 95% inclusive; in some embodiments, in a range from 70% and 95% inclusive; in some embodiments, in a range from 75% and 90% inclusive. In some embodiments, the porous wall of the anchor portion defines a porosity in the range of 60% to 98% inclusive; in some embodiments, in a range from 70% and 95% inclusive; in some embodiments, in a range from 75% and 95% inclusive; in some embodiments, in a range from 80% and 95% inclusive. Optionally, the porous wall of the body is a meshed structure. The porous wall of the filter portion can also be configured as a meshed structure. Optionally, the filter portion defines pore sizes in a range from 40 μm to 1000 μm inclusive; in some embodiments, in a range from 300 μm to 1000 μm inclusive; in some embodiments, in a range from 400 μm to 800 μm inclusive; in some embodiments, in a range from 400 μm to 600 μm inclusive; in some embodiments, in a range from 600 μm to 800 μm inclusive; in some embodiments, in a range from 500 μm to 700 μm inclusive.

Various embodiments of a filter device disclosed herein include a body comprising a porous wall and having a proximal end and a distal end and defining a body axis that passes through the proximal end and the distal end. A filter cap is operatively coupled to the proximal end of the body, the filter cap being either planar or convex relative to the body axis in a direction that extends away from the body. The body can optionally define a radial dimension that is larger than a nominal dimension of an artery designated for implantation. In one embodiment, the body includes an anchor portion that comprises a shape memory material.

In some embodiments, the proximal end of the porous wall is configured to filter blood passing therethrough. By configuring the proximal end as a filter, an increased margin of tolerance is realized for placement of the device. That is, absolute registration of the filter cap at all points on the circumference of the ostium is not required to achieve the full effect of filtering and/or diversion.

In various embodiments, the filter cap includes a bulbous portion and can also include a hub portion. In one embodiment, removal of the hub portion configures the filter device in an open configuration whereby the filter cap is open to enable blood flow through the body unfiltered. In another embodiment, the filter cap is detachable from the body to configure the filter device in an open configuration whereby the filter cap is open to enable blood flow through the body unfiltered. The hub portion can include a disc portion that is seated within the bulbous portion. In some embodiments, the bulbous portion is resilient. In one embodiment, the hub portion is replaceable.

In various embodiments of the disclosure, a blood filter is disclosed comprising a body that includes: an anchor portion including a first end that defines a flow outlet port, the flow outlet port being normal to a body axis, the anchor portion including a first porous wall; and a filter portion that extends from the anchor portion, the filter portion including a second porous wall and defining a lateral bypass aperture proximate a second end of the body. Optionally, the filter portion includes an elbow portion the second end of the body, the elbow portion defining the lateral bypass aperture. Optionally, the filter portion includes an extension portion that extends laterally from the elbow portion, the extension portion defining the lateral bypass aperture. Optionally, the first porous wall and second porous wall are of substantially equal porosity; alternatively, the first porous wall defines a first porosity, the second porous wall defines a second porosity, the first porosity being greater than the second porosity. In one embodiment, the first porosity defines a first average pore size, and the second porosity defines a second average pore size, the second average pore size being less than the first average pore size.

In various embodiments of the disclosure, a blood filtering system is disclosed, comprising a plurality of filter devices, each including a body. Each body includes an anchor portion defining a flow outlet port at a first end of the body, the outlet port being normal to a first axis, the anchor portion including a porous wall. A filter portion extends from the anchor portion, the filter portion including a porous wall and defining a bypass aperture at a second end of the body, the bypass aperture being normal to a second axis, the second axis defining a non-zero angle with respect to the first axis. In some embodiments, the non-zero angle of each of the plurality of filter devices is in a range from 60° and 120° inclusive. In certain embodiments, the non-zero angle of each of the plurality of filter devices is substantially 90°. Optionally, the filter portion of each of the plurality of filter devices includes an elbow-shaped portion that depends from the anchor portion, the elbow-shaped portion defining the bypass aperture. Optionally, each of the plurality of filter devices includes an elbow-shaped portion that depends from the anchor portion and an extension portion that extends from the elbow-shaped portion, the extension portion defining the bypass aperture. For various embodiments, the bypass aperture is centered on the second axis at a distance in a range of 20 mm to 60 mm inclusive from the first axis. For some embodiments, the bypass aperture is centered on the second axis at a distance in a range of 6 mm to 10 mm inclusive from the first axis. Optionally, the porous wall of the anchor portion of each of the plurality of filter devices defines a first average pore size, and the porous wall of the filter portion of each of the plurality of filter devices defines a second average pore size, the second average pore size being less than the first average pore size.

In various embodiments, a slot is defined on a superior face of the filter portion, the filter portion thereby defining a channel opening at a lateral end of the filter portion. The slot extends through the elbow-shaped portion and into the anchor portion.

In another embodiment of the disclosure, a method for filtering blood flowing into an artery is presented. The method can comprise one or more of the following:

providing a filter device having an body and a filter cap, the body comprising an anchor portion having a porous wall, a proximal end, and a distal end, the body defining a body axis that passes through the proximal end and the distal end, the filter cap being operatively coupled to the proximal end of the body, the filter cap being either planar or convex relative to the body axis in an upstream direction;

disposing the filter device in the artery so that the filter cap is upstream of the anchor portion;

positioning the filter cap in a geometrical plane defined by an ostium of an artery;

positioning the filter cap in an upstream direction from a geometrical plane defined by an ostium of an artery, such that a wall portion of the proximal end of the body filters blood passing therethrough;

removing the hub portion to open the filter cap, for example by unscrewing the hub from the filter cap;

The filter cap provided in the step of providing a filter device can comprise a meshed structure. In one embodiment, the meshed structure is a flat mesh.

BRIEF DESCRIPTION OF THE DRAWINGS

Figure 16:
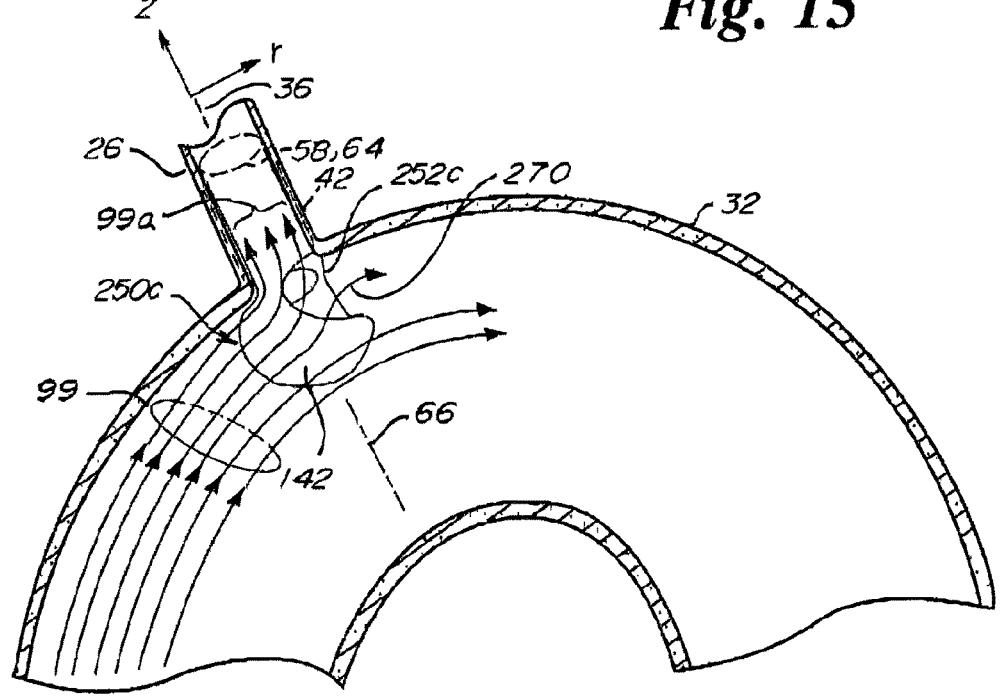
FIG. 16 is a cutaway perspective view of a filter device in an implanted configuration the filter device including a bulbous filter cap and having a lateral bypass aperture in an embodiment of the disclosure.

FIG. 1 is a frontal cutaway view of a human heart with a filter device implanted in an embodiment of the disclosure;

FIG. 1A is an enlarged, schematic view of the filter device of FIG. 1 in an implanted configuration in an embodiment of the disclosure;

FIG. 1B is a perspective, distal end view of the filter device of FIG. 1A in isolation;

FIG. 1C is a is a perspective, proximal end view of the filter device of FIG. 1A in isolation;

FIG. 1D is an enlarged, partial view of FIG. 1B in an embodiment of the disclosure;

FIG. 2 is a schematic view of a filter device in an implanted configuration in an embodiment of the disclosure;

FIG. 2A is a perspective view of a filter device having a porosity that varies axially in an embodiment of the disclosure;

FIG. 3 is a sectional view of a filter device in an implanted configuration, the filter device having a porosity that varies tangentially in an embodiment of the disclosure;

FIG. 3A is a perspective, distal end view of the filter device of FIG. 3 in isolation;

FIG. 4 is a schematic view of a filter device having a convex filter cap in an implanted configuration in an embodiment of the disclosure;

FIG. 5 is a perspective view of a filter device having lateral protrusions in an implanted configuration in an embodiment of the disclosure;

FIG. 6 is a perspective view of a filter device having a bulbous filter cap in an implanted configuration in an embodiment of the disclosure;

FIG. 7 is a perspective view of the filter of FIG. 6 in an open configuration;

FIGS. 8A through 8F are perspective views of a fabrication of filter devices having bulbous filter caps in embodiments of the disclosure;

FIG. 9 is a perspective view of a detachable bulbous filter cap in an embodiment of the disclosure;

FIG. 10 is a perspective, exploded view of a detachable, replaceable bulbous filter cap having a stem portion in an embodiment of the disclosure;

FIG. 11 is a perspective view of a bulbous filter device having a removable hub with a disc portion in an embodiment of the disclosure;

FIG. 12 is a sectional view of a bulbous filter device having a removable, replaceable hub having a disc portion in an embodiment of the disclosure;

FIG. 13 depicts the bulbous filter device of FIG. 12 in an implanted configuration with the removable, replaceable hub and disc removed;

FIG. 14 is a cutaway perspective view of a straight cylinder filter device in an implanted configuration with a bypass aperture at a proximal end in an embodiment of the disclosure;

FIG. 15 is a cutaway perspective view of a filter device in an implanted configuration the filter device including a convex filter cap and having a lateral bypass aperture in an embodiment of the disclosure;

FIG. 16 is a cutaway perspective view of a filter device in an implanted configuration the filter device including a bulbous filter cap and having a lateral bypass aperture in an embodiment of the disclosure;

FIG. 17 is a cutaway perspective view of a filter device in an implanted configuration the filter device defining a curved cylinder with a lateral bypass aperture in an embodiment of the disclosure;

FIG. 17A is a perspective view of the implanted filter device of FIG. 17 in isolation;

FIG. 18 is a cutaway perspective view of a filter device in an implanted configuration, the filter device defining a curved cylinder with a lateral bypass aperture in an embodiment of the disclosure;

FIG. 18A is a perspective view of the implanted filter device of FIG. 18 in isolation;

FIG. 19 is a cutaway perspective view of a filter device in an implanted configuration, the implanted filter device defining a curved cylinder that defines a lateral bypass aperture and having a porosity that varies tangentially in an embodiment of the disclosure;

FIG. 19A is a perspective view of the implanted filter device of FIG. 19 in isolation;

FIG. 19B is a perspective view of the filter device of FIG. 19 with optional centering hook in an embodiment of the disclosure;

FIG. 20 is a cutaway perspective view of a filter device in an implanted configuration, the filter device defining a curved cylinder with a slot and channel in an embodiment of the disclosure;

FIGS. 20A and 20B depict the filter device of FIG. 20 with differing slot lengths in embodiments of the disclosure;

FIG. 21 is a perspective view of a detached centering hook in an embodiment of the disclosure;

FIG. 22 is a sectional view of a dual anchor filter device in an implanted configuration in an embodiment of the disclosure;

FIG. 22A is a perspective view of the implanted dual anchor filter device of FIG. 22 in isolation;

FIG. 22B is a perspective view of the dual anchor filter device of FIG. 22A in a fully expanded configuration prior to implantation in an embodiment of the disclosure;

FIG. 23 is a perspective view of a fully expanded dual anchor filter device having anchor portions of different diameters in an embodiment of the disclosure;

FIG. 24 is a sectional view of a dual anchor filter device with a lateral bypass aperture in an implanted configuration in an embodiment of the disclosure;

FIG. 24A is a perspective view of the dual anchor filter device of FIG. 24 in the implanted configuration in isolation;

FIG. 25 is a sectional view of a dual anchor filter device with a shrouded bypass aperture in an implanted configuration in an embodiment of the disclosure;

FIG. 25A is a perspective view of the dual anchor filter device of FIG. 25 in the implanted configuration in isolation;

FIG. 26 is a sectional view of a double filter arrangement in an embodiment of the disclosure; and FIGS. 26A through 26D is a sectional view of alternative double filter arrangements in embodiments of the disclosure.

DETAILED DESCRIPTION OF THE DRAWINGS

Referring to FIGS. 1 through 1D, a filter device 20 is depicted in an implanted configuration 22 and in isolation in an embodiment of the disclosure. The filter device 20 is depicted as being implanted in the ostium 24 (take-off) of an artery 26, and more specifically into a branch 28 of an aortic arch 32 to filter the blood flowing into the artery 26 from the aortic arch 32. The artery 26 can be characterized as having an effective flow radius 34 relative to a central flow axis 36. The FIG. 1 depiction also presents, without limitation, various candidate arteries for implantation of the filter device 20, including the innominate artery (and attendant right carotid and right subclavian arteries), the left carotid artery, and the left subclavian artery. The FIG. 1 depiction also identifies a superior direction 30 and an inferior direction 31 of the anatomy.

The filter device 20 includes a body 46 and a filter cap or element 44. In one embodiment, the body 46 includes a porous wall 48 having an inner surface 52, an outer surface 54, a proximal end 56 and a distal end 58, the distal end 58 defining an opening 62 that serves as a flow outlet port 64. (Herein, "proximal" and "distal" are relative terms that refer generally to the direction of blood flows, with proximal being generally upstream from distal.) In various embodiments, the flow outlet port 64 is open, i.e., does not include a filtering medium that transverses the body axis 66. In one embodiment, the proximal end 56 of the body 46 is capped by the filter cap 44. The body 46 defines a body axis 66 that passes through the proximal and distal ends 56 and 58 of the body 46. The outer surface 54 defines a maximum outer radial dimension 68 relative to the body axis 66. In one embodiment, the body 46 is effectively a stent, comprising a meshed structure 72 that can be substantially cylindrical in shape, as depicted. In various embodiments, the body is dimensioned to provide an interference fit between an arterial wall 74 and the body 46 when in an expanded state to anchor the filter device 20 in the implanted position. Optionally, the body 46 can be balloon expandable or self-expanding.

The filter cap 44 can comprise a substantially planar disc 74 that covers the proximal end 56 of the body 46. In one embodiment, the filter cap 44 is unitary with the proximal 56 end of the body 46. Herein, a cap that is "unitary" with the body is integrally formed with the body, without need for a separate connection step to secure the cap to the body. Alternatively, the filter cap 44 can be formed as a separate component that is then joined to the body, for example using mechanical connections or with an adhesive or by a fusion or welding process. In various embodiments, the filter cap 44 comprises a meshed structure 76.

The meshed structures 72, 76 of the body 46 and the filter cap 44, when utilized, can be a flat mesh 78, as depicted in FIG. 1D. The flat mesh 78 can be comprised of a web 80 of cross-members 82 formed of a substantially sheet-like structure 86 and that define a plurality of openings 84 in a matrix arrangement. The flat sheet structure can be rolled into the cylindrical shape either before or after the formation of the openings 84. Alternatively, instead of a flat sheet, the openings 84 can be formed in a hollow cylinder to provide a uniform body thickness (i.e., no overlap). The plurality of openings 84 can be rectangular in shape, as depicted in FIG. 1D, each opening 84 being surrounded and defined by adjacent cross-members 82 of the web 80, and such that the cross-members 82 intersect at substantially right angles. Other geometries for the openings 84 and cross-members 82 are also contemplated, including but not limited to parallelograms (i.e., where cross-members intersect at non-right angles) or circular apertures formed in the sheet-like structures 86. The openings 84 of the flat mesh 78 can be formed by techniques available to the artisan, such as laser machining, electro-discharge machining (EDM), or mold injections techniques. Alternatively, the meshed structures 86 can comprise a woven mesh (not depicted), wherein the cross-members 82 comprise interwoven strands.

The meshed structures 86 can be characterized by mesh sizing parameters that can include the number of cross-members 82 per lineal length, a projected width of the cross-members (defined as the width of the cross-member as projected in a direction normal to the meshed structures), and/or an open fraction (defined as the open area of the meshed structure per unit area of meshed structure). A non-limiting example of the mesh sizing parameters suitable for the anchor portion 42 of some embodiments of the present disclosure include pore sizes in a range from 500 µm to 5000 µm inclusive; in some embodiments, in a range from 500 µm to 3000 µm inclusive; in some embodiments, in a range from 800 µm to 2000 µm inclusive; in some embodiments, in a range from 800 µm to 1500 µm inclusive; in some embodiments, in a range from 1000 µm to 1500 µm inclusive. A non-limiting example of the mesh sizing parameters suitable for the filtering portion 110 of some embodiments of the present disclosure include pore sizes in a range from 40 µm to 1000 µm inclusive; in some embodiments, in a range from 300 µm to 1000 µm inclusive; in some embodiments, in a range from 400 µm to 800 µm inclusive; in some embodiments, in a range from 400 µm to 600 µm inclusive; in some embodiments, in a range from 600 µm to 800 µm inclusive; in some embodiments, in a range from 500 µm to 700 µm inclusive. In some embodiments, the open fraction of the anchor portion 42 and/or the filter portion 110 is in a range from 50% and 95% inclusive; in some embodiments, in a range from 60% and 90% inclusive; in some embodiments, in a range from 70% and 90% inclusive; in some embodiments, in a range from 75% and 85% inclusive. In embodiments employing cross-members 82 of substantially uniform width, a non-limiting example of the projected width of the cross-members 82 is between 40 µm to 1000 µm inclusive; in some embodiments, in a range from 300 µm to 1000 µm inclusive; in some embodiments, in a range from 400 µm to 800 µm inclusive; in some embodiments, in a range from 400 µm to 600 µm inclusive; in some embodiments, in a range from 600 µm to 800 µm inclusive; in some embodiments, in a range from 500 µm to 700 µm inclusive. For embodiments implementing woven strand meshed structures, the projected width of the cross-members is taken as the diameter of the woven strands.

The porous wall 48 and/or filter cap 44 can be characterized as having a "porosity." Herein, "porosity" is defined as the ratio of the void volume to the total volume of a representative sample of the medium. For meshed structures 86, the total volume of a unit area of mesh is defined by the overall thickness of the unit area of the meshed structure 86 multiplied by that unit area. The void volume is the volume complementary to the volume of the cross-members 82 per unit area of meshed structure 86 (i.e., the volume not occupied by the cross-members 82 of the meshed structure 86 per unit area). In addition to mesh structures, "porosity" also describes open cell structures, which can also be utilized for the porous wall 48 and/or various filter caps.

The anchor portion 42 and/or filter cap 44 can include one or several of a number of materials available to the artisan, including metals (e.g., stainless steel, platinum, platinum-iridium alloys, nickel-cobalt alloys, nickel-titanium alloys (e.g., NITINOL), and bio-absorbable alloys such as magnesium based alloys) and various polymers (e.g., polyethylene terephthalate (PET), polyurethane, and bio-absorbable polymers such as polylactic acid based polymers).

In use, in various embodiments, the filter device 20 is inserted into the ostium 24 (take-off) of the artery 26, and more specifically into the branch 28 of the aortic arch 32 to filter the blood flowing into the artery 26 from the aortic arch 32, as depicted in FIG. 1A. In one embodiment, the filter device 20 is designed in a way that, when inserted into the ostium 24 of the branch 28 of the aortic arch 32, the filter cap 44 is located in the same geometrical plane as the take-off 24 of the artery 26.

In various embodiments, the body 46 includes an anchor portion 42. The anchor portion 42 is so-named because it is configured to anchor the body 46 to the artery 26. In some embodiments, the anchor portion 42 is the same length as the body 46; that is, the entire body 46 can be configured as an anchor portion 42. In various embodiments, the anchor portion 42 comprises an elastic material such as cobalt-chromium-nickel alloys (e.g., ELGILOY), platinum-iridium alloys or nickel-titanium alloys. In this case the device could be seated in the artery using the self-expanding force of the elastic material. In other embodiments, the anchor portion 42 can be comprised of a material such as stainless steel or cobalt-chromium alloys and can be deployed using the plastic deformation of those materials. In this case the device could be delivered into the artery using expansion balloon (like a balloon expandable stent). In some embodiments, the anchor portion 42 is comprised of a material that is pliable but having substantial "shape memory" (i.e., having a tendency to return to its original shape after deformation). Materials having these characteristics include certain alloys such as nickel-titanium. In other embodiments, the anchor portion 42 can be comprised of a material that is pliable but has little or no shape memory. Materials having these characteristics include polymers generally as well as malleable metals generally.

The body 46 can be tailored so that, in an implanted (expanded) configuration, the diameter of the body 46 (i.e., twice the outer radial dimension 68) is suited for implantation in a particular artery. For example: Anchor portions 42 tailored for innominate arteries may have diameters in one of the following ranges: 9 to 14 mm inclusive; 10 mm to 14 mm inclusive; 11 mm to 13 mm inclusive. Anchor portions 42 tailored for subclavian arteries may have diameters in one of the following ranges: 6 to 12 mm inclusive; 7 mm to 11 mm inclusive; 8 mm to 10 mm inclusive. Anchor portions 42 tailored for carotid arteries may have diameters in one of the following ranges: 5 mm to 10 mm inclusive; 5 mm to 9 mm inclusive; 6 mm to 8 mm inclusive.

Functionally, the method of implantation of the filter device 20 can depend on the mechanical properties of the materials of which the device is composed as well as the shape memory characteristics of the anchor portion 42. For anchor portions 42 that are self-expanding or having substantial shape memory characteristics, the filter device 20 can be folded or rolled to a configuration of reduced diameter adequate for routing to the implantation site. Once in position at the implantation site, the anchor portion 42 is released. Because of the substantial elasticity or shape memory, the anchor portion 42 returns substantially to the same dimensions. For embodiments where the anchor portion 42 is oversized relative to the effective radius 34 of the artery 26, the anchor portion 42 expands or unfolds to contact the arterial wall 74, creating an interference fit that fixes the filter device 20 in place. In this type of delivery, the filter device initially is situated in a compressed form inside a delivery catheter and liberated during implantation by a withdrawal movement of the catheter relative to device.

For anchor portions 42 having little or no shape memory, the anchor portion 42 can be initially formed as being undersized relative to the effective radius 34 of the artery 26 at the implantation site. Once in position, the anchor portion 42 can be expanded, for example by way of a balloon catheter. By initially and momentarily over-expanding the anchor portion 42 to exceed the nominal dimension 34 of the artery 26 with the balloon catheter, the porous wall 48 of the anchor portion 42 is placed in interference with the arterial wall 74, fixing the filter device 20 in place. In this type of filter device, the balloon-based delivery system passes through the filter device 20, e.g., through one of the pores of the filter cap 44.

For a period of time after implantation, the filter device 20 can be readily removed from the implantation site using standard minimal invasive interventional techniques. Accordingly, the filter device 20 is suitable for temporary use. However, over time, tissue ingrowth provides further fixation of the cross-members of the porous material or mesh to the arterial wall 74, further securing the filter device 20 at the implantation site. Thus, the filer device 20 is suitable for permanent implantation.

Referring to FIG. 2, an implanted configuration 88 of the filter device 20 is depicted in an embodiment of the disclosure. In this embodiment, the filter device 20 is inserted into the ostium 24 of the branch 28 of the aortic arch 32 with the proximal end 56 and the filter cap 44 extending into the lumen of the aortic arch 32 at an immersion length L1 measured parallel to the body axis 66.

Referring to FIG. 2A, an alternative filter device 20a wherein the body 46 includes pore sizes and/or porosity that varies over the length of the anchor portion 42 is depicted in an embodiment of the disclosure. That is, the body portion 46 is characterized as having the anchor portion 42 as well as a filter portion 110. In the depicted embodiment, filter device 20a defines a first porosity 94 having a first average pore size at the distal end 58 of the body 46, while a second porosity 98 having a second average pore size is defined at the proximal end 56 of the body 46. In one embodiment, the second porosity 98 can be the same or nearly the same as the porosity or average pore size of the filter cap 44, with the first average pore sizes and porosity 94 at the distal end 58 of the body 46 being substantially greater.

Functionally, the smaller pore sizes and lower porosity at the proximal end 56 provide filtering functionality, while the larger pore sizes and higher porosity at the distal end 58 can promote tissue ingrowth to provide better anchoring for permanent implantation. Conversely, the distal end 58 of the body 46 can be of a tightly woven mesh or of a non-porous construction to inhibit tissue ingrowth, which is more suitable for temporary implantation.

Referring to FIGS. 3 and 3A, a filter device 90 is depicted in the implanted configuration 88 and in isolation in an embodiment of the disclosure. The filter device 90 includes many of the same components and aspects as the filter device 20, which are indicated with same-numbered numerical references in FIGS. 3 and 3A and/or in the following discussion thereof. A difference between the filter devices 20 and 20a and filter device 90 is that, in a standard cylindrical (r-θ-z) coordinate system 91, the porosity of the porous wall 48 varies in a tangential dimension θ about the body axis 66. As depicted, and as with the filter devices 20 and 20a, the porous wall 48 can comprise the meshed structure 72, but with mesh characteristics that vary in the tangential dimension θ. In one embodiment, an upstream face of the body 46 that faces the blood flow defines smaller pores (i.e., lower porosity) than the surface facing away from the blood flow.

In one embodiment, a first tangential portion 92 of the porous wall 48 of the body 46 defines a first porosity 94, and a second tangential portion 96 of the porous wall 48 defines a second porosity 98 (FIG. 3A), the first tangential portion 92 defining an angle θ1 about the body axis 66 and the first porosity 94 being less than the second porosity 98. In various embodiments, a non-limiting example of the angle θ1 is in the range of 60° to 270° inclusive. In one embodiment, the angle θ1 is in the range of 180° to 270° inclusive.

In operation, the filter device 90 can be oriented in a blood flow 99 (depicted as streamlines in FIG. 3) so that the first tangential portion 92 is upstream of the second tangential portion 96. The blood flow 99 is depicted as a blood cross flow having a flow vector component that is normal to the body axis 66. In one embodiment, the first tangential portion 92 of the porous wall 48 is centered tangentially about the direction of the blood flow 99 as the blood flow 99 approaches the filter device 90. In one embodiment, the immersion length L1 is sufficiently long so that a portion 99a of the blood flow 99 that enters the artery 26 first passes through the porous wall 48 of the body 46.

Functionally, the first tangential portion 92 of the filter device 90 acts as the primary filter for filtering the blood flow 99 that enters the artery 26. Debris that does not pass through the first tangential portion 92 is deflected around the filter device 90 and carried away from the artery. If, over time, the first tangential portion 92 becomes occluded to the point that not enough blood flow 99 can enter the artery 26, blood can still flow into the artery via the second tangential portion 96; the first tangential portion 92 still functions to deflect debris away from the ostium 24. The second tangential portion 96 is of higher porosity 98 to mitigate against occlusion while still providing a sufficient barrier against debris entering the filter device 90.

While varying the porosity of the porous wall 48 in the tangential dimension 9 is depicted for a straight cylinder body in FIGS. 3 and 3A, the general concept of having an upstream face of a filter body possess smaller pore sizes and/or lower porosity than on a downstream face can be implemented with any of the embodiments disclosed herein.

Referring to FIG. 4, a filter device 100 is depicted in an embodiment of the disclosure and implanted in substantially the same orientation as the implanted configuration 88 of FIG. 2. The filter device 100 includes many of the same components and aspects as the filter device 20, which are indicated with same-numbered numerical references in FIG. 4 and/or in the following discussion thereof. A difference between the filter devices 20 and 20a and filter device 100 is that a filter cap 102 of the filter device 100 of FIG. 4 presents a convex surface 104 that bows away from the proximal end 56 of the body 42 and further into the aortic arch 32 along the body axis 66.

It is noted that, in FIG. 4, the second porosity 98 (smaller mesh) of the proximal end 56 extends a ways into the artery 26. That is, the portion of the body 46 that defines the second porosity 98 is actually greater than the immersion length L1. The purpose of this arrangement is to better assure that all of the blood entering the artery 26 passes through the (finer) second porosity 98, while still providing ample length of the anchoring portion 42 to provide the desired tissue ingrowth. This arrangement can be implement for any of the various embodiments disclosed herein that include axial variation of the porosity of the body 46.

For the FIGS. 2, 3, and 4 configurations, the proximal end 56 of the body 46 extends into the lumen of the aortic arch 32. Accordingly, in addition to the anchor portion 42, the body 46 can include a filter portion 110 configured to function as a filter, i.e., having the same filtering characteristics as the filter caps 44, 102, effectively increasing filtration area. The filter flow-through area is thereby increased relative to the implanted configuration 22 of FIG. 1A, which reduces the risk of filter occlusion with emboli. The extension into the lumen of the aortic arch 32 further enables a higher degree of cross flow across the filter cap 44, 102, enhancing the self-cleaning aspect of the filter device 20, 100. The extension of the body 46 into the lumen of the aortic arch 32 further provides an advantage of protecting the filter cap 44, 102 from tissue ingrowth. The convex surface 104 of the filter cap 102 of FIG. 4 further increases the flow-through area of the filter device 100 and further enhances the cross-flow aspect, thereby further enhancing the self-cleaning attribute of the filter device.

Referring to FIG. 5, a barbed filter device 120 is depicted in an embodiment of the disclosure. The barbed filter device 120 can include many of the same aspects and characteristics as the filter device 20, as indicated with same-numbered numerical references in FIG. 5 and/or in the following discussion thereof. The barbed filter device 120 is equipped with lateral protrusions or barbs 122 or similar structures that extend radially beyond the body 46. The lateral protrusions 122 can extend from the filter cap 44 (as depicted) or can extend from the body 46 at or near the proximal end 56. In one embodiment, a dimension 124 from the body axis 66 to a radial extremity 126 of the protrusions 122 is greater than the effective radius 34 of the arterial wall 74.

Functionally, the lateral protrusions 122 interfere with the arterial wall 74 or ostium 24 when implanted. In the embodiment of FIG. 5, the interference of the protrusions with the ostium 24 effectively registers the filter cap 44 in the geometrical plane of the ostium 24. In other embodiments, protrusions 122 are located distal to the filter cap 44 (i.e., extend laterally from the body 46) to interfere with the arterial wall 74 when the barbed filter device 120 is pressed into the artery 26. Thus, the barbed filter device 120 is secured by a mechanism other than (or in addition to) interference between the body 46 and the arterial wall 74, and can be positioned precisely in the ostium 24 before being implanted using techniques described earlier to provide expansion of the porous wall 48 of the body 46.

Referring to FIGS. 6 and 7, a bulbous filter device 140 is depicted in an embodiment of the disclosure. The bulbous filter device 140 includes many of the same components and aspects as the above disclosed filter devices 20 and 100, which are indicated with same-numbered numerical references in FIGS. 6 and 7 and/or in the following discussion thereof. In the depicted embodiment, the body 46 defines a flow inlet port 141 at the proximal end 56, best seen in FIG. 7. The bulbous filter device 140 includes a bulbous filter cap 142 that extends from the flow inlet port 141 of the proximal end 56 having a convex outer surface 144 that covers the flow inlet port 141 of the body 46. A hub 146 is positioned on a proximal face 148 of the bulbous filter cap 142. The bulbous filter cap 142 further defines an outer lateral dimension 152 (e.g., diameter having a radius) normal to the body axis 66. Herein, a characteristic of a "bulbous" filter element is that the lateral dimension 152 is greater than a maximum radial dimension 154 of the body 46. The bulbous filter device 140 combines therefore advantages of the barbed filter device 120 with the filter devices 20 and 100 by extending into the lumen of aortic arch 32.

In one embodiment, the bulbous filter cap 142 is formed from a flared portion 156 that extends radially outward from the body axis to define an outer perimeter 158. Without the hub 146, the bulbous filter cap 142 defines an open configuration 160, as can be seen in FIG. 7, enabling unfiltered flow through the flow inlet and flow outlet ports 141 and 64 of the body 46. In one embodiment, the flared portion 156 is made of an elastic material or a material having shape memory that is formed or set in the open configuration, (for example by a thermosetting process) such that, absent the hub 146, the bulbous filter cap 142 will open up and be substantially restored to the flared configuration 160 of FIG. 7.

Functionally, the bulbous filter cap 142 also provides increased flow-through area relative to the filter devices 20, 100 and 120, further enhancing the self-cleaning capability of the bulbous filter device 140. The hub 146 can be utilized to percutaneously grab and maneuver the bulbous filter device 140, for example with a purpose built snare 162. Also, the hub 146 can be used for removal of the bulbous filter device 140 from the artery 26. Such removal could be done at operator discretion several days or weeks after implantation in case of short term need for embolic protection. The operator in this case can catch the hub 146 with the purpose built snare 162 and remove the bulbous filter device 140 from the artery by traction. It is also contemplated to implement a hub or similar structure in any of the filter devices (e.g., 20, 100, 120), whether bulbous or not, to facilitate removal.

In cases where the bulbous filter device 140 is left for a long period of time in the ostium 24 of the artery 26 and is affixed thereto by ingrown tissue, the removal of the entire device 140 can be impossible using minimally invasive surgical techniques. For such long term or permanent installations, and as a precautionary measure, the hub 146 can be removed in certain embodiments to open up the bulbous filter cap 142 into the open configuration 160 should the bulbous filter cap 142 somehow become obstructed. Restoration to the original open configuration 160 is provided by the elastic forces or the shape memory material.

Referring to FIGS. 8A through 8F, assembly of bulbous filter device 140 is depicted in embodiments of the disclosure. In assembly, and prior to implantation, the outer perimeter 158 of the flared portion 156 (FIG. 8A) is gathered together at a bunched neck 164 (FIG. 8B) that can be tied together by the hub 146 to form the bulbous filter cap 142. Various ways to join the outer perimeter 158 at the hub 146 include: screwing the hub 146 onto the bunched neck 164 (FIG. 8C); crimping the hub 146 onto the bunched neck 164 (FIG. 8D); fusing the bunched neck together (a fused portion 166 forming the hub 146) (FIG. 8E); stapling the bunched neck 146 together (a staple 168 serving as the hub 146) (FIG. 8F). For these embodiments, removal of the hub 146 to restore unfiltered flow can be accomplished, for example, by: unscrewing the hub 146; cutting through the bunched neck proximate the hub 146; cutting through or otherwise removing the staple that serves as the hub 146.

Referring to FIG. 9, a bulbous filter device 180 having a detachable bulbous filter cap 182 is depicted in an embodiment of the disclosure. The bulbous filter device 180 is a variation of the bulbous filter device 140 of FIGS. 6 and 7, and includes many of the same components and aspects, which are indicated with same-numbered numerical references in FIG. 9 and/or in the following discussion thereof. In one embodiment, the detachable bulbous filter cap 182 is pre-formed in the bulbous geometry rather than being gathered in a bunched neck at the hub 146. The detachable bulbous cap 182 can be mounted to a flange 184 that extends radially outward from the proximal end 56 of the body 46. In this embodiment, the hub 146 can be an optional accessory, utilized to grab and maneuver the bulbous filter device with the purpose built snare 162 and to remove the detachable bulbous filter cap 182 from the flange 184. In some embodiments, the junction between the detachable bulbous cap 182 and the flange 184 can be deliberately weakened relative to the remaining structure of the bulbous filter device 180, so that the detachable bulbous cap 182 will separate or tear away from the flange 184 upon exertion of a sufficient pulling force on the hub 146 in the event that the detachable bulbous filter cap 182 becomes occluded.

Referring to FIG. 10, a detachable bulbous filter device 180a is depicted in an embodiment of the disclosure. The detachable bulbous filter device 180a is a variation of the bulbous filter device 180, and as such includes many of the same aspects and components as the detachable bulbous filter device 180, which are indicated with same-numbered numerical references in FIG. 10 and/or in the following discussion thereof. The detachable bulbous filter device 180a includes a stem portion 192 that extends distal to the bulbous filter cap 182. The stem portion 192 has an outer wall 194 dimensioned to fit within the anchor portion 42 (e.g., to have a smaller outer diameter 196 than an inner diameter 198 of the inlet port 141 of the body 46). The stem portion 192 can also comprise a meshed structure. In some embodiments, the stem portion 192 comprises a self-expanding material.

Functionally, the outer diameter 196 of the stem portion 192 contacts the inner surface 52 of the anchor portion 42. The contact provides sufficient interlocking resistance to hold the bulbous filter cap 182 within the anchor portion 42, while enabling the detachable bulbous filter cap 182 to be removed from the anchor portion 42 for replacement. For embodiments implementing the self-expanding material for the stem portion 192, the interlock between the stem portion 192 and the anchor portion 42 can be further enhanced. It is noted, however, that in operation, blood flow through the assembly (bottom to top in FIG. 10) will tend secure the stem portion 192 within the anchor portion 42; accordingly, the interlock between the stem portion 192 and the anchor portion 42 can be light for easier removal.

While the meshed structure of the stem portion 192, when utilized, may experience some ingrowth of tissue over time, the stem portion 192 is separated from the arterial wall 74 by the body 46 of the anchor portion 42, which can substantially reduce the amount of ingrowth, to the point that the stem portion 192 can be removed from the anchor portion 42 even in a permanent installation.

In replacement, the stem portion 192 of the detachable bulbous filter cap 182 can be readily slid into the body 46 of the anchor portion 42. In some embodiments, the stem portion 192 comprises a self-expanding material so that the stem portion 192, initially undersized, grows into seating contact with the inner surface 52 of the body 46 being inserted in the body 46.

Referring to FIG. 11, another bulbous filter device 200 is depicted in an embodiment of the disclosure. The bulbous filter device 200 is a variation of the bulbous filter device 140 of FIG. 6, and includes many of the same components and aspects, which are indicated with same-numbered numerical references in FIG. 11 and/or in the following discussion thereof. In this embodiment, a bulbous filter cap 202 defines a proximal opening 204 on a proximal face thereof. A peripheral portion 208 of the bulbous filter cap 202 is adjacent the proximal opening 204. The hub 146 includes a disc portion 212 that is disposed over or within the proximal opening 204 of the bulbous filter cap 202, the disc portion 212 being in overlapping contact with and being joined to the peripheral portion 208.

In this embodiment, the bulbous filter cap 202 can comprise an elastic or a shape memory material that assumes a flared shape akin to FIG. 7, such that the bulbous geometry of the bulbous filter cap 202 is maintained by the joinder of the disc portion 212 and the flared portion 156 (FIG. 7). In some embodiments, the junction between the bulbous filter cap 202 and the disc portion 212 of the hub 146 are deliberately weakened relative to the remaining structure of the bulbous filter device 200, so that the disc portion 212 will separate or tear away from the bulbous filter cap 202 upon exertion of a sufficient pulling force on the hub 146 in the event that the bulbous filter cap 202 becomes occluded.

In various embodiments, upon removal of the hub 146 and disc portion 122, the bulbous filter cap 140 assumes an open configuration akin to the open configuration 160 of FIG. 7. Joinder of the disc portion 212 to the bulbous filter cap 202 for the open configuration alternative can be accomplished in several ways, including but not limited to: adhesive disposed between the disc portion 212 and the peripheral portion 208 of the bulbous filter cap 202; fusion or welding.

The tear away aspect of the bulbous filters 182, 202 can be accomplished in several ways, including but not limited to: appropriate amounts and selection of adhesive at the junctions; appropriate levels of fusion or welding, provided, for example, by discrete point tack welding; frangible structure at or adjacent the junctions; and electrolytic erosion. An example of electrolytic erosion is presented, for example, at U.S. Pat. No. 7,862,602 to Licata et al.

Referring to FIG. 12, a sectional view a bulbous filter device 220 having a resilient bulbous filter cap 222 and a replaceable disk 226 with hub 224 is depicted in an embodiment of the disclosure. The bulbous filter device 220 includes many of the same aspects and characteristics as the bulbous filter device 200, as indicated with same-numbered numerical references in FIG. 12 and/or in the following discussion thereof. The bulbous filter device 220 takes on the same general appearance as the bulbous filter device 200 of FIG. 11. However, unlike the disc portion 212 of the bulbous filter device 200, the disk 226 does not function to maintain the bulbous geometry of the bulbous filter cap 222 by joinder to an otherwise flared portion; rather, the bulbous filter cap 222, is pre-formed to be resilient in the bulbous geometry, so as to maintain the bulbous geometry sans the disc portion 226.

The disc portion 226 includes an outer perimeter 228 that seats on an inner surface 232 of the bulbous filter cap 222. In one embodiment, the disc portion 226 defines a convex profile 234 that is bowed towards the proximal opening 204. The diameter of the disc portion 226 can be dimensioned to provide a close fit between the outer perimeter 228 and the inner surface 232, at or near a lateral extremity 236 of the inner surface 232 of the bulbous filter cap 222.

In operation, all blood that flows through proximal opening 204 or the peripheral portion 208 of the bulbous filter cap 222 then flows through the filtering structure of the disc portion 226 by virtue of the close fit between the outer perimeter 228 and the inner surface 232 at or near the lateral extremity 236. The dynamic response of the disc portion 226 to the blood flow therethrough can also slightly flatten the convex profile 234, causing the outer perimeter 228 to extend slightly radially outward, thereby further enhancing the seating between the disc portion 226 and the inner surface 232 of the bulbous filter cap 222. In various embodiments, the disc portion 226 comprises a self-expanding material, further augmenting the seating between the disc portion 226 and the inner surface 232 due to the elastic expansion force of the self-expanding material.

Referring to FIG. 13, the bulbous filter device 220 is depicted with the replaceable disk 226 removed from the bulbous filter cap 22 with the purpose built snare 162. The resilient property of the bulbous filter cap 224 facilitates replacement of the disc portion 226, should the disc portion 226 become occluded. To remove the disc portion 226, the hub 224 is snared and a pulling force exerted in a direction parallel to the body axis 66, as depicted in FIG. 13. The pulling force causes the disk 226 to contract and/or the proximal opening 204 to expand as the disc portion 226 is pulled through the proximal opening 204. The resiliency of the bulbous filter cap 222 causes the proximal opening 204 to return substantially to the pre-stressed dimension.

In replacement, a new disc portion 226 is folded to a dimension that clears the proximal opening 204 and fed through the proximal opening 204 and left to unfold within the bulbous filter cap 222. The hub 224 can be used for gripping, orienting, and maneuvering the filter disc portion 226.

For the various bulbous filter devices 140, 180, 180a, 200, and 220, the respective bulbous cap 144, 182, 202, and 222 is of larger radial dimension than the body of the anchor portion 42. Accordingly, the respective bulbous filter device can act to register the bulbous filter device at the mouth of the ostium 24 (e.g., as presented for bulbous filter device 140 at FIG. 6). In other embodiments, the body 46 protrudes into the aortic arch 32 (e.g., as depicted for bulbous filter device 180 at FIG. 9), so that the proximal portion 56 of the body 46 acts as a filter, as discussed attendant to FIGS. 2, 3, and 4 above.

Referring to FIGS. 14 through 20, filter devices 250 that include bypass apertures 252 are depicted in implanted configurations 254 in embodiments of the disclosure. The filter devices 250, bypass apertures 252, and implanted configurations 254 are herein referred to collectively or generically by the numerical references 250, 252, and 254 respectively, and individually with a letter suffix (e.g., filter device 250a, bypass aperture 252a, and implanted configuration 254a). The implanted device depictions of FIGS. 14 through 20 showing flow through the aortic arch 32 portray only the outline of the filter devices 250 (i.e., without depicting meshed walls) for illustrative clarity; representative and non-limiting porous wall structures are illustrated in the various isolated device depictions related to FIGS. 14 through 20.

In one embodiment, as illustrated in FIG. 14, a filter device 250a can include many of the same components and aspects as the filter devices 20, 20a, and 90, which are indicated with same-numbered numerical references in FIG. 14 and/or in the following discussion thereof. A difference between the filter devices 20, 20a, and 90 and the filter device 250a is that filter device 250a does not include a filter cap at the proximal portion 56; rather, the filter portion 110 at the proximal portion 56 of the body 46 defines an opening 255 that is left open to define the bypass aperture 252a. The filter portion 110 extends over the immersion length L1 of the filter device 250a. As disclosed above, the pores of the anchor portion 42 and the filter portion 110 can define first and second porosities 94 and 98, respectively, the second porosity 98 including pores of smaller size and/or defining a lower porosity than the first porosity 94 of anchor portion 42. In one embodiment, the first porosity 94 of anchor portion 42 extends circumferentially around the anchor portion 42, and the second porosity 98 of the filter portion 110 extends circumferentially around the filter portion 110. Alternatively, the porosities of the porous wall 48 can vary tangentially as depicted and discussed attendant to filter device 90 (FIG. 3), with the coarser first porosity 94 being oriented to face in the downstream direction 97 of the aortic arch 32. In one embodiment, the filter device 250a is cylindrical, defining an inner diameter D1, and the immersion length L1 into to the aortic arch 32 is at least as long as the diameter D1.

In implantation and operation, the immersion length L1 for the implanted configuration 254a is of sufficient length so that the portion 99a of the blood flow 99 that enters the artery 26 first passes through the porous wall 48 of the body 46. In the implanted configuration, an upstream portion 258 of the porous wall 48 that faces upstream into the blood flow 99 performs the majority of the filtering. In the event that the upstream portion 258 becomes occluded, the blood flow 99 courses around the occlusions and enters the filter device 250a closer to the lateral sides of the filter device 250a. Because none of the streamlines of the blood flow 99 enter the bypass aperture 252a, none of the blood entering the filter device 250a is unfiltered. This is true even when the filter device 250a becomes partially occluded.

In another embodiment, as illustrated in an implanted configuration 254b in FIG. 15, a filter device 250b can include many of the same components and aspects as the filter device 100 of FIG. 4, which are indicated with same-numbered numerical references in FIG. 15 and/or in the following discussion thereof. As disclosed above, the pores of the anchor portion 42 and the filter portion 110 can define first and second porosities 94 and 98, respectively, the second porosity 98 including pores of smaller size and/or defining a lower porosity than the first porosity 94 of anchor portion 42. In one embodiment, the first porosity 94 of anchor portion 42 extends circumferentially around the anchor portion 42, and the second porosity 98 of the filter portion 110 extends circumferentially around the filter portion 110. A difference between the filter device 100 and the filter device 250b is that filter device 250b includes a bypass aperture 252b formed on the porous wall 48 near the proximal end 56. The bypass aperture 252b is typically oriented to face away from the blood flow 99, i.e., in a downstream direction 97.

Herein, "lateral" bypass apertures are so named because they face at least partially in a direction normal to an axis of the anchor portion. In some embodiments (e.g., FIG. 17, discussed infra), the lateral aperture is formed by curving the body 46 so that an open end of the body is so-oriented. In some embodiments, the lateral aperture is formed on the side of the body 46 (e.g., FIG. 15, discussed infra).

In an embodiment as illustrated in an implanted configuration 254c in FIG. 16, a filter device 250c can include many of the same components and aspects as the bulbous filter device 140 of FIG. 6, which are indicated with same-numbered numerical references in FIG. 16 and/or in the following discussion thereof. As disclosed above, the pores of the anchor portion 42 and the bulbous filter cap 142 can define first and second porosities 94 and 98, respectively, the second porosity 98 including pores of smaller size and/or defining a lower porosity than the first porosity 94 of anchor portion 42. In one embodiment, the first porosity 94 of anchor portion 42 extends circumferentially around the anchor portion 42, and the second porosity 98 of the filter portion 110 extends circumferentially around the filter portion 110. A difference between the bulbous filter device 140 and the filter device 250c is that filter device 250c includes a lateral bypass aperture 252c formed on the bulbous filter cap 142 near the proximal end 56. The lateral bypass aperture 252c is typically oriented to face away from the blood flow 99.

In the embodiment illustrated in implanted configuration 254d in FIG. 17 (depicted in isolation in FIG. 17A), a filter device 250d includes many of the same components and aspects as the filter device 20, which are indicated with same-numbered numerical references in FIG. 17 and/or in the following discussion thereof. In the depicted embodiment, the first porosity 94 of anchor portion 42 extends circumferentially around the anchor portion 42, and the second porosity 98 of the filter portion 110 extends circumferentially around the filter portion 110 (FIG. 17A). The body 46 of the filter device 250d defines a curved cylinder 259 about a curved body axis 66. The filter portion 110 of the curved cylinder 259 of the filter device 250d includes an elbow portion 260 defined near the proximal end 56, the elbow portion 260 defining a lateral bypass aperture 252d. In the depicted embodiment, the bypass aperture 252d intersects the body axis 66 at a substantially right angle. In one embodiment, the curved cylinder 259 includes an extension portion 262 that extends in the radial direction r of the cylindrical coordinate system 91. The bypass aperture 252d is typically oriented to face away from the blood flow 99.

A characteristic of the filter device 250d, and of embodiments generally that define a curved body axis 66, the flow outlet port 64 is normal to a first axis 253, and the lateral bypass aperture 252d is normal to a second axis 257, the axes 253 and 257 being concentric with the curved body axis 66. The first axis 253 is not parallel to the second axis 257; that is, the second axis defines a non-zero angle with respect to the first axis. The depiction of FIG. 17A presents the first and second axes 253 and 257 as being substantially normal to each other. For various embodiments, the filter device 250d defines an angle that is in a range of 60° to 120° inclusive; in some embodiments, in a range of 70° to 110° inclusive; in some embodiments, in a range of 80° to 100° inclusive.

In the embodiment illustrated in implanted configuration 254e in FIG. 18, a filter device 250e can include many of the same components and aspects as the filter device 20, which are indicated with same-numbered numerical references in FIG. 18 and/or in the following discussion thereof. The filter portion 110 of the filter device 250e defines a curved cylinder 259 that, at least in the implanted configuration, includes or expands into an arcuate or elbow-shaped portion 260 defined near the proximal end 56, with the body axis 66 being curved through the elbow-shaped portion 260. As disclosed above, the pores of the anchor portion 42 and the filter portion 110 can define first and second porosities 94 and 98, respectively, the second porosity 98 including pores of smaller size (finer porosity or mesh) and/or defining a lower porosity than the first porosity 94 of anchor portion 42. The elbow-shaped portion 260 defines a bypass aperture 252e. In the depicted embodiment, the bypass aperture 252e lies substantially on a plane 262 that intersects the curved body axis 66 at an acute angle $\phi$. The bypass aperture 252e is typically oriented to face away from the blood flow 99. By this arrangement, coverage of both the ostia of a first artery 272 and an adjacent artery 274 is provided.

For the embodiment illustrated in implanted configuration 254f in FIG. 19, filter device 250f includes many of the same components and aspects as the filter device 250d of FIGS. 17 and 17A, which are indicated with same-numbered numerical references in FIG. 19 and/or in the following discussion thereof. Like the filter device 250d, device 250f defines the curved cylinder 259 and the filter portion 110 includes the elbow-shaped portion 260 near the proximal end 56, and a bypass aperture 252f that intersects the body axis 66 at a substantially right angle. The bypass aperture 252f is typically oriented to face away from the blood flow 99.

For the filter device 250f, an elongated extension portion 262f of the filter portion 110 has sufficient lateral dimension L to extend laterally (i.e., in the radial direction r of the r-θ-z coordinate 91) from the elbow-shaped portion 260 over the ostium of an adjacent artery 274 (e.g., the ostium of the left carotid artery and, in some embodiments, also the left subclavian artery of FIG. 1) when the filter device 250f is implanted in a first artery 272 (e.g., the innominate artery of FIG. 1). In one embodiment, the elongated extension portion 262f is dimensioned to have a larger diameter than the anchor portion 42 to augment full coverage of the ostium of the adjacent artery, thereby compensating for directional alignment uncertainty. In some embodiments, the elongated extension portion 262f can be resilient and pre-formed to define an elliptical cross-section (not depicted) with the major axis of the ellipse being oversized to augment full coverage of the ostium of the adjacent artery. In some embodiments, the extension portion 262f can be resilient and define a circular cross-section, but, under the stresses imposed on the elongated extension portion 262f in the implanted configuration 254f, assumes an elliptical cross-section.

Referring to FIGS. 19A and 19B, the filter device 250f is depicted in embodiments of the disclosure. The depicted embodiments of FIGS. 19A and 19B are the same, except the FIG. 19B embodiment includes a centering hook 276. In these embodiments, the porosities of the porous wall 48 are configured to vary tangentially, akin to filter device 90 depicted and discussed attendant to FIG. 3. The filter device 250f is configured so that a superior face 282 and a downstream-oriented face 284 of the body 46 defines the (coarser) first porosity 94, the downstream-oriented face 284 being axially adjacent to the superior face 282 along the curved body axis 66. The filter device 250f is further configured so that an inferior face 286 and an upstream-oriented face 288 of the body 46 includes the (finer) second porosity 98, the upstream-oriented face 288 being axially adjacent to the inferior face 286 along the curved body axis 66.

Functionally, having the finer second porosity 98 on the inferior and upstream-oriented faces 286 and 288 provides filtration of the blood flow 99a entering the implanted first artery 272 (e.g., the innominate artery), as well as a blood flow 99b entering the adjacent artery 274 (e.g., the left carotid artery). The coarser first porosity 94 on the superior and downstream-oriented faces 282 and 284 enhances tissue ingrowth into the filter device 250f over time for better anchoring. Also, having the coarser first porosity 94 cover ostium of the adjacent artery 274 partially mitigates the double filtering of the entering blood stream and attendant restriction in blood flow.

By orienting the bypass apertures 252b-252f to face away from the blood flow 99, an outflux 270 of blood through the bypass apertures 252b-252f is maintained under normal operating conditions. That is, blood flow 99 that enters the filter devices 250b-250f (i.e., through the porous wall 48, the bulbous filter cap 142, or the elbow-shaped portion 260) that is not drawn into the artery 26 will pass through the bypass apertures 252b-252f of filter devices 250b-250f. Accordingly, any debris that is deflected by the filter devices 250b-250f will bypass the bypass apertures 252b-252f and not be drawn into the filter devices 250b-250f. The outflux 270 can be maintained (albeit at less intensity) even if the filter device 250b-250f becomes partially occluded. Thus, despite the presence of unfiltered bypass apertures 252, blood flow 99a entering the artery 26, blood flow 99a entering the artery 26 still passes through a filter medium in normal operation, and even when the filter device 250 is in a partially occluded state.

In the unlikely event that the filter device 250b-250f becomes so heavily occluded as to interrupt normal operation, blood can still flow into resident artery. In such a scenario, some of the blood flowing past the heavily occluded filter portion 110 would be drawn into the bypass apertures 252b-252f to enter the artery.

In various embodiments, the bypass apertures 252 are sized to define access ports dimensioned to permit surgical instruments to pass through the filter device 250 for servicing of the artery 26, without need for destroying or otherwise compromising the filter device 250. The bypass apertures 252 can also allow transradial access to thoracic aorta when the filter device is implanted, for example, in the ostium of innominate artery or left subclavian artery. The bypass aperture 252 can also permit blood flow therethrough in the unlikely event that the filter device 250 becomes heavily occluded.

For the embodiment illustrated in implanted configuration 254g in FIG. 20, filter device 250g includes many of the same components and aspects as the filter device 250f of FIGS. 19, 19A, and 19B, which are indicated with same-numbered numerical references in FIG. 20 and/or in the following discussion thereof. Like the filter device 250f, device 250g defines the curved cylinder 259, and the filter portion 110 includes the elbow-shaped portion 260 near the proximal end 56, with an elongated extension portion 262g of the filter portion 110 having sufficient lateral dimension L to extend laterally from the elbow-shaped portion 260 over the ostium of the adjacent artery 274 when the filter device 250g is implanted in a first artery 272.

The filter device 250g defines a slot 271 that extends along the elongated extension portion 262g and faces in the superior direction 30. As such, in the depicted embodiment, a downstream or lateral end 273 of the elongated extension portion 262g does not define a tube and aperture, but rather a channel 275 and channel opening 277. The channel opening 277 is typically oriented to face away from the blood flow 99. Depending on the length of the slot 271, the filter device 250g can also incorporate the optional centering hook 276 of the filtering device 250f.

In the implanted configuration 254g, the channel 275 passes over the ostium of the adjacent artery 274. In one embodiment, the channel 275 contacts the wall of the aortic arch 32, and the slot 271 and channel 275 provide an opening on the elongated extension portion 262g that aligns over the ostium of the adjacent artery 274. Also, akin to the elongated extension portion 262f, the elongated extension portion 262g can be resilient and pre-formed to outline a generally elliptical cross-section, or can assume the elliptical cross-section under the stresses of the implanted configuration 254g.

Functionally, for filter devices 250f and 250g, the dimensioning the elongated extension portion 262, 262g to cover the ostium of the adjacent artery 274 provides an additional degree of filtration and protection of the adjacent artery 274. In some embodiments, the lateral dimension L is long enough to cover more than one adjacent artery 274. For example, the lateral dimension L can be sized so that the filter device 250f, 250g, when mounted in the innominate artery, extends to cover both the left carotid artery and the left subclavian artery of FIG. 1. Blood can still flow through the porous walls of the elongated extension portion 262 to enter the adjacent artery 274, while emboli that could otherwise swirl into the adjacent artery 274 would be generally blocked by the porous walls of the elongated extension portion 262, 262g. Furthermore, the slot 271 and channel 275 of the filter device 250g entirely eliminates any double filtering of the blood flow 99b entering the adjacent artery 274. "Double filtering" occurs when a blood flow must pass through the filter portion 110 twice, which imposes an unnecessary and generally undesirable restriction to blood flow. The slot 271 eliminates the porous wall 48 that would otherwise be immediately adjacent the ostium of the adjacent artery 274, so there is no double filtering of the blood flow 99b.

As discussed attendant to FIGS. 20A and 20B below, the slot 271 and channel 275 of filter device 250g further enable the elongated extension portion 262g to spread or flare out at the channel opening 277, effectively enlarging the width of the elongated extension portion 262g to augment full coverage of the ostium of the adjacent artery 274, thereby compensating for directional alignment uncertainty.

Referring to FIGS. 20A and 20B, filter devices 250h and 250i are depicted, respectively, in embodiments of the disclosure. The filter devices 250h, 250i are embodiments of the filter device 250g, and as such include all of the components and aspects as the filter device 250g, which are indicated with same-numbered numerical references in FIGS. 20A and 20B and/or in the following discussion thereof. Also, the filter devices 250h, 250i can include some components and attributes identified for the filter device 250f of FIGS. 19, 19A, and 19B, which are also identified with same-numbered numerical references in FIGS. 20A and 20B and/or in the following discussion thereof.

For filter device 250h, the slot 271 extends over a portion of the elongated extension portion 262g. For the filter device 250i, the slot 271 extends over the entire length of the elongated extension portion 262g, through the elbow-shaped portion 260, and into the anchor portion 42 of the body 46. Generally, for a given stiffness of the porous wall 48, the longer the slot 271, the wider the elongated extension portion 262g can be spread or fanned out at the channel opening 277, such that the filter portion 110 defines a fanned filter portion 110g. The fanned filter portion 110g is depicted in dashed lines in FIGS. 20A and 20B. In relative terms, the shorter slot of FIG. 20A provides a channel opening 277 having less fanning (narrower spread) with a larger opening dimension in the superior direction 30; the longer slot of FIG. 20B provides a channel opening with greater fanning (wider spread) with a smaller opening dimension in the superior direction 30.

Accordingly, for a given stiffness of the porous wall 48, the channel opening 277 can be tailored to a desired depth in the implanted configuration 254g by dimensioning of the slot 271. In one embodiment, the fanning of the filter portion 110 can eliminate or nearly eliminate any definition of an open channel 277, such as depicted in FIG. 20B. In such an embodiment, the fanned filter portion 110g is akin to a flap that effectively lays over the ostium of the adjacent artery 274. For these embodiments, the porous wall 48 can be configured with sufficient flexibility to enable the fanned filter portion 110g to be lifted away for access to both the adjacent artery 274 and the first artery 272.

In various embodiments, the fanned filter portion 110g defines a maximum width dimension that is in a range of 6 mm to 20 mm inclusive; in some embodiments, a range of 6 mm to 15 mm inclusive; in some embodiments, a range of 7 mm to 12 mm inclusive; in some embodiments, a range of 7 mm to 10 mm inclusive.

As with the filter device 250f, discussed attendant to FIG. 19A, the porosities of the porous wall 48 of the filter devices 250h and 250i can be configured to vary tangentially. Alternatively, the porosities of the porous wall 48 can be configured to vary axially along the curved body axis 66, such as with filtering device 250d of FIG. 17A with the first porosity 94 of anchor portion 42 extends circumferentially around the anchor portion 42, and the second porosity 98 of the filter portion 110 extends circumferentially around the filter portion 110.

Referring to FIG. 18A and again to FIG. 18, the filter device 250e is presented with an optional centering hook 276 in an embodiment of the disclosure. The FIG. 18 depiction (as well as the FIGS. 19 and 20 depictions) presents the first artery 272 as an innominate artery, and also presents the adjacent artery 274 as the left carotid artery extending from the aortic arch 32. The filter device 250e can optionally include the centering hook 276 extending laterally outward (i.e., in a direction away from the curved body axis 66) from the outer surface 54 of the porous wall 48 of the filter device 250e (FIG. 18A).

The centering hook 276 can be dimensioned to bridge the ostia of the first artery 272 and the adjacent artery 274, and to extend into the first artery 272 and the adjacent artery 274, as depicted in FIG. 18. In various embodiments, the centering hook 276 is fabricated from a resilient material so that it is held in place in part by restorative elastic forces incurred during implantation. That is, the centering hook 276 can be dimensioned to define a span 279 that is undersized (FIG. 18A), so that inserting the centering hook 276 in place between the adjacent ostia of the arteries 272 and 274 causes the span 279 to expand after insertion. The span 279 is defined as the distance between a free end 281 and a shank portion 283 of the centering hook 276 in a direction perpendicular to the portion of the body axis 66 that passes through the anchor portion 42 of the filter device 250e. The expansion of the span 279 generates a restorative force that holds or pinches the filter device 250e between the centering hook 276 and the ostium. Optionally, or in addition, the centering hook 276 can be attached to the porous wall 48 by various means available to the artisan, including fusion to the porous wall 48, or by integral formation with the wall 48. In one embodiment, the centering hook 276 can be integrally formed as an extension of one of the cross-members of a meshed structure (e.g., one of the cross-members 82 of meshed structure 86 of FIG. 1D).

The centering hook 276 can also include a spherical or otherwise radiused barb 278. The radiused barb 276 presents dulled (i.e., not sharp) features, as opposed to traditional barbs that are designed to tenaciously set into a target. In comparison to traditional barbs, the radiused barb 278 is less prone to tearing the tissue both during the approach and at target. The radiused barb 278 is also less prone to tearing the filter device 250d during approach and implantation.

Functionally, the centering hook 276 can help maintain the angular orientation (θ orientation of the cylindrical coordinate system 91) of the filter device 250e, which further aids in aligning and maintaining alignment of the bypass aperture 252e in an orientation that faces away from the blood flow 99. The radiused barb 278 can also promote the permanency of the installation, as tissue grows over the radiused barb 278 over time; because the radiused barb is not sharp, such tissue growth can occur without the radiused barb 278 cutting through the growth tissue.

In some embodiments, the centering hook 276 further induces the curvature of the elbow-shaped portion 260 when the filter device 250e is in the implanted configuration 254e. That is, prior to implantation, the filter device 250e may assume a straight configuration, or at least a straighter (less arcuate or less pronounced elbow shape) configuration than in the implanted configuration 254e. The centering hook 276 can be joined to the filter device 250e such that, when hooked to the ostium of the adjacent artery 274, the elbow-shaped portion 260 becomes fully defined. In this manner, the filter device 250d can provide a lower profile during the approach. Alternatively, or in addition, the elbow portion 260 can be permanently formed by, for example, a thermo-setting process or by use of a shape-memory materials.

Referring to FIG. 21, a detached centering hook 280 is depicted in an embodiment of the disclosure. The detached centering hook 280 is not connected to the filter device 250e; instead the centering hook 280 is installed separately as a clip. In one embodiment, the centering hook 280 includes the radiused barbs 278 on both the free end 281 and an opposed free end 285. In this embodiment, the span 279 is taken as the distance between the free end 281 and the opposed free end 285. The FIG. 21 depiction also represents both the span 279 and an expanded span 279a in phantom that generates the restorative force that holds or pinches the wall 48 of the filter device 250e between the centering hook 280 and the ostium. In various embodiments, the detached centering hook 280 can be utilized as a retrofit to previously implanted filter devices 250. The detached centering hook 280 provides the same retention and alignment functionality as the centering hook 276, discussed above.

While the centering hooks 276, 280 are described in association with the filter devices 250e, it is understood that centering hooks 276, 280 can be implemented with a variety of the filter devices 250 of the present disclosure. For example, the centering hook 276 (or optionally detached centering hook 280) can be implemented with the filter device 250f to aid in aligning and maintaining alignment of the elongated extension portions 262f, 262g to cover the ostium of the adjacent artery 274. The centering hook 276, 280 further aids in maintaining the bypass aperture 252f or channel opening 277 oriented in the downstream direction 97.

Referring to FIGS. 22, 22A, and 22B, a dual anchor filter device 300a is depicted in an embodiment of the disclosure. A variety of dual anchor filter devices 300 are disclosed herein, referred to collectively or generically by the numerical reference 300 and individually with a letter suffix (e.g., filter device 300a). The dual anchor filter device 300a includes a first anchor portion 302 and a second anchor portion 304 disposed on opposing ends of a filter portion 306. The first anchor portion 302 defines a first outer diameter 308 and includes many of the same components and aspects as, for example, the filter devices 20, which are indicated with same-numbered numerical references in FIGS. 22, 22A, and 22B and/or in the following discussion thereof. The second anchor portion 304 is of similar construction to the first anchor portion 302, defining a second outer diameter 312, a second flow outlet port 314, and including a porous wall 316 that defines a porosity 318. In one embodiment, the porosity 318 is substantially the same as the first porosity 94 of the first anchor portion 302.

In some embodiments, the first anchor portion 302 is dimensioned for anchoring to the first artery 272 and the second anchor portion 304 is dimensioned for anchoring to the adjacent artery 274. It is noted that, while the adjacent artery 274 may be generally of a different diameter than the first artery 272, the first and second outer diameters 308 and 312 can be of the same dimension and still function to reliably anchor the respective anchor portions 302 and 304.

Referring to FIG. 23, a dual anchor filter device 300b is depicted in an embodiment of the disclosure. The dual anchor filter device 300b includes many of the same components and aspects as the dual anchor filter device 300a, which are indicated with same-numbered numerical references in FIG. 23 and/or in the following discussion thereof. The dual anchor filter device 300b is characterized as having first and second diameters 308 and 312 that are of different dimension, with the second diameter 312 being less than the first diameter 308.

In the depicted embodiment, a transition 320 between the first and second diameters 308 and 312 is defined on a part of the porous wall 48 having the second porosity 98. This enables the (finer) second porosity to extend partially into the ostium of the resident artery 274 for better assurance of filtering all of the blood that enters the artery 274.

In this embodiment, the first and second diameters 308 and 312 can be configured for a more tailored anchoring fit of the first artery 272 and the adjacent artery 274, respectively. Ranges of representative diameters for various arteries is discussed above attendant to FIGS. 1A through 1D. Accordingly, for various embodiments of the dual anchor filter devices 300 tailored for anchoring in the innominate and the left carotid arteries may define a ratio of the first diameter 308 to the second diameter 312 in one of the following non-limiting ranges: 1 to 3 inclusive; 1.4 to 2 inclusive; 1.6 to 1.8 inclusive. A dual anchor filter device for anchoring in the left carotid and left subclavian arteries may define a ratio of the first diameter 308 to the second diameter 312 in one of the following non-limiting ranges: 0.3 to 1 inclusive; 0.5 to 1; 0.9 to 0.7 inclusive. Note that the former range clusters have ratios greater than or equal to unity while the latter range clusters have ratios less than or equal to unity, reflecting the diameters of upstream and downstream arteries for the two configurations.

Referring to FIGS. 24 and 24A, a dual anchor filter device 300c is depicted in an embodiment of the disclosure. The dual anchor filter device 300c includes the same components and aspects as the dual anchor filter device 300a, which are indicated with same-numbered numerical references in FIGS. 24 and 24A and/or in the following discussion thereof. In addition, the dual anchor filter device 300c includes a lateral bypass aperture 322 formed in the filter portion 306. In one embodiment, the lateral bypass aperture 322 is disposed proximate the second anchor portion 304 and oriented to face in the downstream direction 97 within the aortic arch 32.

Referring to FIGS. 25 and 25A, a dual anchor filter device 300d is depicted in an embodiment of the disclosure. The dual anchor filter device 300d includes the same components and aspects as the dual anchor filter device 300c, which are indicated with same-numbered numerical references FIGS. 25 and 25A and/or in the following discussion thereof. In addition, the filter portion 302 of the dual anchor filter device 300d includes a shroud 324 formed on the filter portion 306 and protruding radially outward (i.e., in a direction away from the body axis 66), the shroud 324 surrounding the lateral bypass aperture 322.

Functionally, the dual anchor filter devices 300 provide full filtering of the two arteries 272 and 274 (e.g., the innominate artery and the left carotid artery). The dual anchors also fix the orientation of the filter devices 300. The higher porosities 94, 318 (e.g., larger pore sizes) of the anchoring portions 302, 304 facilitate tissue ingrowth into the anchor portions 302 and 304, while the lower porosity 98 (e.g., small pore sizes) of the filter portion 306 facilitate thorough filtering of the blood entering both arteries. The bypass aperture 322, being oriented to face away from the blood flow, operates akin to the bypass apertures 252 described attendant to FIGS. 16 through 20. The shroud 324 offers an added level of prevention against recirculating emboli entering the filter.

Referring to FIG. 26, a double filter arrangement 350 is depicted in an embodiment of the disclosure. The double filter arrangement 350 includes two filter devices, a first or upstream filter device 352a, and a second or downstream filter device 352b. The filter device 352a is configured for implantation in an upstream artery 354a, and the filter device 352b is configured for implantation in a downstream artery 354b. For the depicted embodiment of the double filter arrangement 350, each of the filter devices 352a and 352b include the same components and attributes as the filter device 250d (FIG. 17), which are indicated with same-numbered numerical references FIG. 26 and/or in the following discussion thereof. Also for the depicted embodiment, the upstream and downstream arteries 354a and 354b are the innominate and left carotid arteries of FIG. 1.

For certain embodiments that utilize the filter device 250d in the upstream artery 354a, a length 356a of the extension portion 262 is dimensioned to provide a minimum radial separation 358 between the bypass aperture 252d of the upstream filter device 352a and the elbow portion 260 of the downstream filter device 352b. Herein, a "radial separation" is a dimension parallel the radial direction r of the cylindrical coordinate system 91 of the upstream filter device 352a.

In various embodiments, non-limiting dimensions for the minimum radial separation 358 are in the range of 2 mm to 5 mm inclusive. In various embodiments, to obtain the desired minimum radial separation 358, the bypass aperture 252d of the upstream filter device 352a is centered at a lateral dimension L2 in a range of 3 mm to 12 mm inclusive from a centerline of the anchor portion; in some embodiments, a range of 5 mm to 10 mm inclusive; in some embodiments, a range of 5 mm to 8 mm inclusive; in some embodiments, a range of 6 mm to 8 mm inclusive.

The configuration of the porous wall 48 of the body 46 of each of the filter devices 352a and 352b may be congruent with various embodiments disclosed herein. For the depicted embodiment of the double filter arrangement 350, each of the filter devices 352a and 352b include the first porosity 94 of anchor portion 42 extending circumferentially around the anchor portion 42, and the second porosity 98 of the filter portion 110 extending circumferentially around the filter portion 110. Alternatively, the anchor and filter portions 42 and 110 of the filter devices 352a and 352b can be configured with porosities 94, 98 that vary tangentially about the curved body axis 66, akin to the filter device 250f discussed attendant to FIG. 19A. Also, for arrangements such as depicted in FIG. 26, where the upstream artery 354a is proximate the downstream artery 354b, the upstream filter device 352a may be configured with a centering hook (not depicted) that bridges the ostia of the upstream and downstream arteries 354a and 354b, akin to the centering hook 276 discussed attendant to FIG. 18 or the detached centering hook 280 discussed attendant to FIG. 21.

As described above attendant to FIGS. 14 through 20, the bypass apertures 252d of the upstream and downstream filter devices 352a and 352b can be sized to define access ports dimensioned to permit surgical instruments to pass through the respective filter device 352a, 352b, for servicing of the respective artery 354a, 354b and without need for destroying or otherwise compromising the filter device 352a, 352b.

Functionally, the downstream-facing orientation of bypass apertures 252d enable transradial access to the arteries 354a and 354b. The minimum radial separation 358 enable surgical instrument access to the bypass aperture 252d of the upstream filter device 352a without substantially disturbing the downstream filter device 352b. That is, surgical instruments (e.g., a guide wire) utilizing a transradial approach can pass over the arcuate surface of the elbow portion 260 of the downstream filter device 352b for entry into the bypass aperture 252d of the upstream filter device 352a with little or mere incidental contact with the downstream filter device 352b.

Further functional aspects of the double filter arrangement 350 are as provided in similar embodiments described above. For example, the double filter arrangement 350 provides affirmative filtering of both arteries 354a and 354b (e.g., the innominate artery and the left carotid artery). The higher porosities 94 (e.g., larger pore sizes) of the anchoring portions 42 facilitate tissue ingrowth into the anchor portions 42, while the lower porosities 98 (e.g., small pore sizes) of the filter portion 110 facilitate thorough filtering of the blood entering the respective arteries 354a and 354b. The bypass apertures 252d, being oriented to face away from the blood flow, operate akin to the bypass apertures 252 described attendant to FIGS. 15 through 20. The bypass apertures 252d can also permit blood flow therethrough in the unlikely event that the respective filter device 352a, 352b becomes heavily occluded.

Alternative embodiments for double filter arrangements 350a through 350d are presented in FIGS. 26A through 26D in embodiments of the disclosure. For double filter arrangement 350a, the upstream filter device 352a does not include an extension portion that extends laterally from the elbow portion 260; rather, the bypass aperture 252d is defined on the elbow portion 260 (FIG. 26A). This effectively increases the minimum radial separation 358 relative to the double filter arrangement 350, thereby increasing accessibility of the upstream filter device 352a.

For the double filter arrangement 350b, the upstream filter device 352a is the filter device 250b, described attendant to FIG. 15 above. The bypass aperture 252b of filter device 250b is defined in on a lateral side of the body 46 (FIG. 26B), such that the lateral dimension L2 is limited to the radius of the filter portion 110. This also increases the minimum radial separation 358 relative to the double filter arrangement 350.

For the double filter arrangement 350c, the upstream filter device 352a is the filter device 250a, described attendant to FIG. 14 above. The bypass aperture 252a is oriented to face primarily in the inferior direction 31 and at the immersion depth L1 (FIG. 26C). As such, access to the upstream filter device 352a is unaffected by the presence of the downstream filter device 252b.

For the double filter arrangement 350d, the upstream filter device 352a is similar to the filter device 250d of FIGS. 17 and 26, except that the filter portion 110 includes an axial extension 368 that extends an axial length 366 from the ostium of the first artery 354a (FIG. 26D). The axial extension 368 extends the bypass aperture 252d in the inferior direction 31 relative to the bypass aperture 252d of the downstream filter device 352b. By this arrangement, access to the upstream filter device 252a is unfettered by the downstream filter device 252b.

For the depictions of FIGS. 26 and 26A-26D, the downstream filter device 352b is depicted and identified as filter device 250d. It is understood that the double filter arrangements 350, 350a-350d are not limited to the use of filter device 250d in the downstream artery 354b. Rather, the artisan will recognize that any of the filter devices utilized in the upstream artery 354a can also be utilized in the downstream artery 354b, as well as several of the other filter devices disclosed herein.

The context of the double filter arrangement 350 of the description above is for implantation in an innominate and a left carotid artery (FIG. 1). It is understood that the principles of the double filter arrangement 350 are not limited to these arteries, or to the use of only two filter devices. That is, in various embodiments, the principles described can be implemented with any of a variety of take-off arteries and in some cases with more than two arteries, as recognized by the skilled artisan.

While the embodiments depicted in FIGS. 2 through 26D include some form of variation of the porosity of the body 46, it is contemplated that any of the embodiments disclosed herein can be optionally configured with a substantially uniform porosity, such as depicted in FIGS. 1A through 1D.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant art will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

The following references, referred to herein above, are hereby incorporated by reference herein in their entirety except for patent claims and express definitions contained therein above: U.S. Pat. Nos. 6,712,834 and 6,866,680 to Yassour, et al.; U.S. Pat. No. 7,670,356 to Mazzocchi et al.; U.S. Pat. No. 6,258,120 to McKenzie et al.; U.S. Pat. No. 8,430,804 to Belson; U.S. Pat. No. 8,062,324 to Shimon et al.; U.S. Pat. No. 8,460,335 to Carpenter; U.S. Pat. No. 7,862,602 to Licata et al.; and U.S. Patent Application Publication No. 2009/0254172 to Grewe.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

References to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A method for implanting a blood filter that includes a filter portion and an anchor portion, said filter portion including an elbow portion and an extension portion, said elbow portion depending from said anchor portion, said extension portion having a proximal end that defines a bypass aperture, said extension portion including a superior face that defines a first porosity and an inferior face opposite said superior face that defines a second porosity, said first porosity being greater than said second porosity, the method comprising:

disposing said anchor portion in a first artery of an aortic arch;

orienting said filter portion so that said bypass aperture is in a downstream direction of a blood flow in said aortic arch; and positioning said blood filter so that said superior face of said extension portion of said filter portion is in contact with a wall of said aortic arch.

2. The method of claim 1, comprising orienting said extension portion of said filter portion so that said superior face at least partially covers an ostium of a second artery of said aortic arch, said second artery being adjacent said first artery.

3. The method of claim 2, wherein said first artery is an innominate artery and said second artery is a left carotid artery.

* * * * *